(12) United States Patent
Tso et al.

(10) Patent No.: US 9,028,830 B2
(45) Date of Patent: May 12, 2015

(54) ANTIBODIES TO CD122

(75) Inventors: J. Yun Tso, Menlo Park, CA (US); Naoya Tsurushita, Palo Alto, CA (US); Nicholas F. Landolfi, Menlo Park, CA (US); Shankar Kumar, Pleasanton, CA (US)

(73) Assignee: JN Biosciences, LLC, Mountain View, CA (US)

( * ) Notice: Subject to any disclaimer, the term of this patent is extended or adjusted under 35 U.S.C. 154(b) by 700 days.

(21) Appl. No.: 13/082,352

(22) Filed: Apr. 7, 2011

(65) Prior Publication Data

US 2011/0250213 A1    Oct. 13, 2011

Related U.S. Application Data

(60) Provisional application No. 61/322,229, filed on Apr. 8, 2010, provisional application No. 61/360,405, filed on Jun. 30, 2010.

(51) Int. Cl.
| | |
|---|---|
| *A61K 39/395* | (2006.01) |
| *C07K 16/00* | (2006.01) |
| *C07K 16/28* | (2006.01) |
| *A61K 39/00* | (2006.01) |

(52) U.S. Cl.
CPC ........ *C07K 16/2866* (2013.01); *A61K 2039/505* (2013.01); *C07K 2317/24* (2013.01); *C07K 2317/73* (2013.01); *C07K 2317/76* (2013.01)

(58) Field of Classification Search
USPC .......................... 424/172.1; 530/387.3, 387.9
See application file for complete search history.

(56) References Cited

U.S. PATENT DOCUMENTS

2009/0175823 A1    7/2009    Martin et al.

FOREIGN PATENT DOCUMENTS

WO    WO 2005/021734 A2    3/2005

OTHER PUBLICATIONS

Ibragimova and Eade (Biophysical Journal, Oct. 1999, vol. 77, pp. 2191-2198).*
Abbvie Deutschland GMBH & Co. v Janssen Biotech, Inc., CAFC, (Jul. 1, 2014; 2013-1338,-1346).*
Goebel, J. et al, "Daclizumab (Zenapax®) inhibits early interleukin-2 receptor signal transduction events," *Transplant Immunology*, 8:153-159, (2000).
Hakimi, J. et al, "Humanized Mikβ1, a humanized antibody to the IL-2 receptor β-chain that acts synergistically with humanized anti-TAC," *Journal of Immunology*, 151(2)1075-1085, (1993).
PCT International Search Report and Written Opinion of the International Searching Authority for PCT/US2011/031640 mailed Feb. 20, 2011.
Pilson, et al, "Bispecific humanized anti-IL-2 receptor αβ antibodies inhibitory for both IL-2- and IL-15-mediated proliferation," *Journal of Immunology*, 159:1543-1556, (1997).
Tanaka et al, "A novel monoclonal antibody against murine IL-2 receptor β-chain,"*Journal of Immunology*, 147(7):2222-2228, (1991).
Waldmann, et al., "The use of antibodies against the IL-2 receptor in transplantation," *Current Opinion in Immunology*, 10:507-512, (1998).
EPO Application No. EP 11766761.8, Supplementary European Search Report, mailed Nov. 20, 2013.
PCT International Preliminary Report on Patentability (Chapter I) for application PCT/US2011/031640 mailed Oct. 12, 2012.
Tinubu et al., "Humanized Antibody Directed to the Il-2 Receptor Beta-Chain Prolongs Primate Cardiac Allograft Survival," The Journal of Immunology, 153:4330-4338, (1994).
Waldmann, "Targeting the interleukin-15/interleukin-15 receptor system in inflammatory autoimmune diseases," Arthritis Research & Therapy, 60):174-177, (2004).
Yang et al., "Development of a quantitative cell-based ELISA, for a humanized anti-IL-2/IL-15 receptor beta antibody (HuMikbeta1), and correlation with functional activity using an antigen-transfected murine cell line," Journal of Immunological Methods, 311(1-2):71-80, (2006).

\* cited by examiner

*Primary Examiner* — Lynn Bristol
(74) *Attorney, Agent, or Firm* — Alston & Bird LLP

(57) ABSTRACT

The invention provides monoclonal antibodies that specifically bind to CD122, which is one component of receptors for IL-2 and IL-15. The monoclonal antibodies have the capacity for substantial inhibition of both IL-2 and IL-15 mediated functions by inhibiting binding of these cytokines to their receptors. The monoclonal antibodies can be used for inhibiting undesired immune responses or treatment of cancer, among other applications.

13 Claims, 20 Drawing Sheets

```
ATGAAGTTGTGGTTAAACTGGGTTTTTCTTTTAACACTTTTACATGGTATCCAGTGTGAG
 M   K   L   W   L   N   W   V   F   L   L   T   L   L   H   G   I   Q   C   E

GTGAAGCTGGTGGAATCTGGAGGAGGCTTGGTACAGCCTGGGGGTTCTCTGAGACTCTCC
 V   K   L   V   E   S   G   G   G   L   V   Q   P   G   G   S   L   R   L   S

TGTGCAACTTCTGGGTTCACCTTCAGTGATTTCTACATGGAGTGGGTCCGCCAGCCTCCA
 C   A   T   S   G   F   T   F   S   D   F   Y   M   E   W   V   R   Q   P   P

GGGAAGAGACTGGAGTGGATTGCTGCAAGTAGAAACAAAGCTAATGATTATACAACAGAG
 G   K   R   L   E   W   I   A   A   S   R   N   K   A   N   D   Y   T   T   E

TACAGTGCATCTGTGAAGGGTCGGTTCATCGTCTCCAGAGACACTTCCCAAAGCATCCTC
 Y   S   A   S   V   K   G   R   F   I   V   S   R   D   T   S   Q   S   I   L

TACCTTCAGATGAATGCCCTGAGAGCTGAGGACACTGCCATTTATTACTGTGCAAGATCC
 Y   L   Q   M   N   A   L   R   A   E   D   T   A   I   Y   Y   C   A   R   S

TACTATAGGTACGACGGTATGGACTACTGGGGTCAAGGAACCTCAGTCACCGTCTCCTCA
 Y   Y   R   Y   D   G   M   D   Y   W   G   Q   G   T   S   V   T   V   S   S
```

Nucleotide sequence of mouse ABC2 VH cDNA (SEQ ID NO:1) along with the deduced amino acid sequence (SEQ ID NO:2).

Figure 3

```
ATGGATTTTCAAGTGCAGATTTTCAGCTTCCTGCTAATCAGTGCCTCAGTCATAGTGTCC
 M   D   F   Q   V   Q   I   F   S   F   L   L   I   S   A   S   V   I   V   S

AGAGGACAAGTTGTTCTCACCCAGTCTCCAGTAATCATGTCTGCATCTCCAGGGGAGAAG
 R   G   Q   V   V   L   T   Q   S   P   V   I   M   S   A   S   P   G   E   K

GTCACCATGACCTGCAGTGCCATCTCAAGTGTAAGTTACATGTACTGGTACCAGCAGAAG
 V   T   M   T   C   S   A   I   S   S   V   S   Y   M   Y   W   Y   Q   Q   K

CCAGGATCCTCCCCCAGACTCCTGATTTATGACACATCCAACCTGGTTTCTGGAGTCCCT
 P   G   S   S   P   R   L   L   I   Y   D   T   S   N   L   V   S   G   V   P

GTTCGCTTCAGTGGCAGTGGGTCTGGGACCTCTTACTCTCTCACAATCAGCCGAATGGAG
 V   R   F   S   G   S   G   S   G   T   S   Y   S   L   T   I   S   R   M   E

GCTGAAGATGCTGCCACTTATTACTGCCAGCAGTGGAATACTTACCCGTACACGTTCGGA
 A   E   D   A   A   T   Y   Y   C   Q   Q   W   N   T   Y   P   Y   T   F   G

GGGGGGACCAAGCTGGAAATAAAA
 G   G   T   K   L   E   I   K
```

Nucleotide sequence of mouse ABC2 VL cDNA (SEQ ID NO:3) along with the deduced amino acid sequence (SEQ ID NO:4).

Figure 4

```
ATGAGAGTGTTGATTCTTGTGTACCTGTTGACAGTCCTTCCTGGTATACTGTCTGATGTA
 M  R  V  L  I  L  V  Y  L  L  T  V  L  P  G  I  L  S  D  V

CAGCTTCAGGAGTCAGGACCTGGCCTGGTGAAGCCTTCTCAGACAGTGTCCCTCACCTGC
 Q  L  Q  E  S  G  P  G  L  V  K  P  S  Q  T  V  S  L  T  C

ACTGTCACTGGCTACTCTATCACTAATGATAATCACTGGTGGAACTGGATCCGGCAGGTT
 T  V  T  G  Y  S  I  T  N  D  N  H  W  W  N  W  I  R  Q  V

TCAGGAAGCAAACTGGAGTGGATGGGGTACATAGACTCCAGTGGTAGTTCTGACAACAAT
 S  G  S  K  L  E  W  M  G  Y  I  D  S  S  G  S  S  D  N  N

CCATCTCTCAAAAGTCAAATCTCCATCACTAGAGACACTTCCAAGAACCAGTTATTCCTG
 P  S  L  K  S  Q  I  S  I  T  R  D  T  S  K  N  Q  L  F  L

CAGTTGAACTCTGTGACTATTGAAGATATAGGCACATATTACTGTGCAAGAGGCGGTGGT
 Q  L  N  S  V  T  I  E  D  I  G  T  Y  Y  C  A  R  G  G  G

AGGGATTACTATGGCATGGACTACTGGGGTCAAGGAACCTCAGTCACCGTCTCCTCA
 R  D  Y  Y  G  M  D  Y  W  G  Q  G  T  S  V  T  V  S  S
```

Nucleotide sequence of mouse ABC101 VH cDNA (SEQ ID NO:5) along with the deduced amino acid sequence (SEQ ID NO:6).

Figure 5

```
ATGGAGACAGACACACTCCTGCTATGGGTGCTGCTGCTCTGGGTTCCAGGTTCCACTGGT
 M   E   T   D   T   L   L   W   V   L   L   W   V   P   G   S   T   G

GACATTGTGCTGACACAGTCTCCTGCTTCCTTAGCTGTATCTCTGGGGCAGAGGGCCACC
 D   I   V   L   T   Q   S   P   A   S   L   A   V   S   L   G   Q   R   A   T

ATCTCATGCAGGGCCAGCCAAAGTGTCAGTACATCTAGCTATAGTTATGTTCACTGGTAC
 I   S   C   R   A   S   Q   S   V   S   T   S   S   Y   S   Y   V   H   W   Y

CAACAGAAACCAGGACAGCCACCCAAACTCCTCATCAAGTATGCATCCAACCTAGAATCT
 Q   Q   K   P   G   Q   P   P   K   L   L   I   K   Y   A   S   N   L   E   S

GGGGTCCCTGCCAGGTTCAGTGGCAGTGGGTCTGGGACAGACTTCACCCTCAACATCCAT
 G   V   P   A   R   F   S   G   S   G   S   G   T   D   F   T   L   N   I   H

CCTGTGGAGGAGGAGGATACTGCAACATATTACTGTCAGCACAGTTGGGACATTCCGTTC
 P   V   E   E   E   D   T   A   T   Y   Y   C   Q   H   S   W   D   I   P   F

ACGTTCGGAGGGGGGACCAAGCTGGAAATAAAA
 T   F   G   G   G   T   K   L   E   I   K
```

Nucleotide sequence of mouse ABC101 VL cDNA (SEQ ID NO:7) along with the deduced amino acid sequence (SEQ ID NO:8).

Figure 6

```
                        1          2          3
            123456789 0123456789 0123456789 0123456789
ABC2 VH     EVKLVESGG GLVQPGGSLR LSCATSGFTF SDFYMEWVRQ
HuABC2 VH   EVQLVESGG GLVQPGGSLR LSCAASGFTF SDFYMEWVRQ
DA430129 VH EVQLVESGG GLVQPGGSLR LSCAASGFSF SDHYMDWVRQ 4          5             6          7
            0123456789 0122223456789 0123456789 0123456789
                       abc
ABC2 VH     PPGKRLEWIA ASRNKANDYTTEY SASVKGRFIV SRDTSQSILY
HuABC2 VH   APGKGLEWIA ASRNKANDYTTEY SASVKGRFIV SRDDSKNSLY
DA430129 VH APVKGLEWVG RTRDKANSYTTEY AASVKGRFTV SRDDSKNSLY 1              1
            8             9            0              1
            0122223456789 0123456789   00000000123456789 0123
            abc                        abcdefg
ABC2 VH     LQMNALRAEDTAI YYCARSYYRY   DGM-----DYWGQGTSV TVSS
HuABC2 VH   LQMNSLKTEDTAV YYCARSYYRY   DGM-----DYWGQGTTV TVSS
DA430129 VH LQMNSLKTEDTAV YYCVRGGAAM   ARGYQDGLDVWGQGTTV TVSS
```

Alignment of the amino acid sequences of the mature ABC2 VH (SEQ ID NO:25), humanized ABC2 VH (HuABC2 VH) (SEQ ID NO:41), and human acceptor DA430129 VH (SEQ ID NO:45) regions.

Figure 7

```
SpeI
ACTAGTACCACCATGAAGTTGTGGTTGAACTGGGTTTTTCTTTTGACACTTTTGCATGGA
              M  K  L  W  L  N  W  V  F  L  L  T  L  L  H  G

ATCCAGTGTGAAGTGCAGCTCGTGGAATCTGGAGGAGGCTTGGTTCAGCCTGGGGGATCT
 I  Q  C  E  V  Q  L  V  E  S  G  G  G  L  V  Q  P  G  G  S

CTGAGACTCTCCTGTGCAGCCTCTGGGTTCACCTTCAGTGATTTCTACATGGAGTGGGTC
 L  R  L  S  C  A  A  S  G  F  T  F  S  D  F  Y  M  E  W  V

CGCCAGGCTCCAGGGAAGGGGCTCGAGTGGATTGCTGCAAGTAGAAACAAAGCTAATGAT
 R  Q  A  P  G  K  G  L  E  W  I  A  A  S  R  N  K  A  N  D

TATACAACAGAGTACAGTGCATCTGTGAAGGGTCGGTTCATCGTCTCCAGAGACGATTCC
 Y  T  T  E  Y  S  A  S  V  K  G  R  F  I  V  S  R  D  D  S

AAGAACTCACTCTACCTTCAGATGAATAGCCTGAAAACCGAGGACACTGCCGTGTATTAC
 K  N  S  L  Y  L  Q  M  N  S  L  K  T  E  D  T  A  V  Y  Y

TGTGCAAGATCCTACTATAGGTACGACGGTATGGACTACTGGGGTCAAGGAACCACAGTC
 C  A  R  S  Y  Y  R  Y  D  G  M  D  Y  W  G  Q  G  T  T  V

HindIII
ACCGTCTCCTCAGGTAAGTTGGCTTTTTTAAGCTT
 T  V  S  S
```

Nucleotide sequence of the HuABC2 VH gene (SEQ ID NO:9) flanked by SpeI and HindIII sites (underlined) along with the deduced amino acid sequence (SEQ ID NO:10).

Figure 8

```
                        1          2          3
            123456789  0123456789 0123456789 0123456789
ABC2 VL     QVVLTQSPV  IMSASPGEKV TMTCSAIS-S VSYMYWYQQK
HuABC2 VL   EIVLTQSPA  TLSLSPGERA TLSCSAIS-S VSYMYWYQQK
M29469 VL   EIVLTQSPA  TLSLSPGERA TLSCRASQSV SSYLAWYQQK 4          5          6          7
            0123456789 0123456789 0123456789 0123456789
ABC2 VL     PGSSPRLLIY DTSNLVSGVP VRFSGSGSGT SYSLTISRME
HuABC2 VL   PGQAPRLLIY DTSNLVSGVP ARFSGSGSGT DYTLTISSLE
M29469 VL   PGQAPRLLIY DASNKATGVP ARFSGSGSGT DFTLTISSLE 1
            8          9          0
            0123456789 0123456789 01234567
ABC2 VL     AEDAATYYCQ QWNTYPYTFG GGTKLEIK
HuABC2 VL   PEDFAVYYCQ QWNTYPYTFG GGTKVEIK
M29469 VL   PEDFAVYYCQ QSSKWPLTFG GGTKVEIK
```

Alignment of the amino acid sequences of the mature ABC2 VL (SEQ ID NO:30), humanized ABC2 VL (HuABC2 VL) (SEQ ID NO:42), and human acceptor M29469 VL (SEQ ID NO:46) regions.

Figure 9

```
NheI
GCTAGCACCACCATGGATTTTCAAGTGCAGATTTTCAGCTTCCTGCTGATCAGTGCCTCA
          M  D  F  Q  V  Q  I  F  S  F  L  L  I  S  A  S

GTCATCGTGTCCAGAGGAGAAATTGTGCTCACCCAGTCTCCAGCCACCCTGTCTTTGTCT
 V  I  V  S  R  G  E  I  V  L  T  Q  S  P  A  T  L  S  L  S

CCAGGGGAGAGAGCCACCCTCTCCTGCAGTGCCATCTCAAGTGTGAGTTACATGTACTGG
 P  G  E  R  A  T  L  S  C  S  A  I  S  S  V  S  Y  M  Y  W

TACCAGCAGAAGCCAGGACAGGCTCCCAGACTCCTGATTTATGACACATCCAACCTGGTG
 Y  Q  Q  K  P  G  Q  A  P  R  L  L  I  Y  D  T  S  N  L  V

TCTGGAGTCCCTGCCCGCTTCAGTGGCAGTGGATCTGGGACCGACTACACTCTCACAATC
 S  G  V  P  A  R  F  S  G  S  G  S  G  T  D  Y  T  L  T  I

AGCAGCCTGGAGCCTGAAGATTTTGCCGTTTATTACTGCCAGCAGTGGAATACTTACCCC
 S  S  L  E  P  E  D  F  A  V  Y  Y  C  Q  Q  W  N  T  Y  P

EcoRI
TACACCTTCGGAGGGGGGACCAAAGTGGAAATCAAACGTAAGTAGAATCCAAGAATTC
 Y  T  F  G  G  G  T  K  V  E  I  K
```

Nucleotide sequence of the HuABC2 VL gene (SEQ ID NO:11) flanked by NheI and EcoRI sites (underlined) along with the deduced amino acid sequence (SEQ ID NO:12).

Figure 10

```
                        1          2          3
             123456789  0123456789 0123456789 012345556789
                                                       ab
ABC101   VH  DVQLQESGP  GLVKPSQTVS LTCTVTGYSI TNDNHWWNWIRQ
HuABC101 VH  QVQLQESGP  GLVKPSQTLS LTCTVSGYSI TNDNHWWNWIRQ
DA936142 VH  QVQLQESGP  GLVKPSQTLS LTCTVSGGSI DNTGFYWSWIRQ 4          5          6          7
             0123456789 0123456789 0123456789 0123456789

ABC101   VH  VSGSKLEWMG YIDSSGSSDN NPSLKSQISI TRDTSKNQLF
HuABC101 VH  HPGKGLEWMG YIDSSGSSDN NPSLKSQITI SRDTSKNQLS
DA936142 VH  HPGKGLEWIG NIYYSGSTYY NPSLKSRVTI SVDTSKNQLS 1           1
             8            9            0           1
             0122223456789 0123456789 00000123456789 0123
                abc                     abcd
ABC101   VH  LQLNSVTIEDIGT YYCARGGGRD YYGM-DYWGQGTSV TVSS
HuABC101 VH  LKLSSVTAADTAV YYCARGGGRD YYGM-DYWGQTTV  TVSS
DA936142 VH  LKLSSVTAADTAV YYCARDWGNS WDRGMDVWGQGTTV TVSS
```

Alignment of the amino acid sequences of the mature ABC101 VH (SEQ ID NO:35), humanized ABC101 VH (HuABC101 VH) (SEQ ID NO:43), and human acceptor DA936142 VH (SEQ ID NO:47) regions.

Figure 11

```
SpeI
ACTAGTACCACCATGAGAGTGTTGATTCTTGTGTACCTGTTGACAGTCCTTCCTGGTATT
         M  R  V  L  I  L  V  Y  L  L  T  V  L  P  G  I

CTGTCTCAGGTACAGCTTCAGGAGTCAGGACCTGGCCTGGTCAAGCCTTCTCAGACACTG
 L  S  Q  V  Q  L  Q  E  S  G  P  G  L  V  K  P  S  Q  T  L

TCCCTCACCTGCACTGTCTCTGGCTACTCTATCACTAATGATAATCACTGGTGGAACTGG
 S  L  T  C  T  V  S  G  Y  S  I  T  N  D  N  H  W  W  N  W

ATCCGGCAGCACCCAGGAAAGGGCCTGGAATGGATGGGGTACATCGACTCCAGTGGTTCC
 I  R  Q  H  P  G  K  G  L  E  W  M  G  Y  I  D  S  S  G  S

TCTGACAACAATCCATCTCTCAAAAGTCAAATCACCATCTCAAGAGACACTTCCAAGAAC
 S  D  N  N  P  S  L  K  S  Q  I  T  I  S  R  D  T  S  K  N

CAGCTCTCCCTGAAGTTGAGCTCTGTGACTGCCGCCGATACAGCCGTGTATTACTGTGCA
 Q  L  S  L  K  L  S  S  V  T  A  A  D  T  A  V  Y  Y  C  A

AGAGGCGGAGGCAGGGATTACTATGGCATGGACTACTGGGGTCAAGGAACCACCGTCACC
 R  G  G  G  R  D  Y  Y  G  M  D  Y  W  G  Q  G  T  T  V  T

HindIII
GTCTCCTCAGGTAAGAATGGCCTCTCAAGCTT
 V  S  S
```

Nucleotide sequence of the HuABC101 VH gene (SEQ ID NO:13) flanked by SpeI and HindIII sites (underlined) along with the deduced amino acid sequence (SEQ ID NO:14).

Figure 12

```
                       1           2               3
           123456789  0123456789  0123456777777789  0123456789
                                        abcdef
AB101 VL   DIVLTQSPA  SLAVSLGQRA  TISCRASQSVST--SS  YSYVHWYQQK
HuAB101 VL DIVMTQSPD  SLGVSLGERA  TINCRASQSVST--SS  YSYVHWYQQK
Z46622 VL  DIVMTQSPD  SLGVSLGERA  TINCKSSQSVLYSSNN  KNYLAWYQQK 4           5           6           7
           0123456789  0123456789  0123456789  0123456789
AB101 VL   PGQPPKLLIK  YASNLESGVP  ARFSGSGSGT  DFTLNIHPVE
HuAB101 VL PGQPPKLLIK  YASNLESGVP  DRFSGSGSGT  DFTLTISSLQ
Z46622 VL  PGQPPKLLIY  WASTRESGVP  DRFSGSGSGT  DFTLTISSLQ 1
           8           9           0
           0123456789  01234556789  01234567
                            a
AB101 VL   EEDTATYYCQ  HSWDIP-FTFG  GGTKLEIK
HuAB101 VL AEDVAVYYCQ  HSWDIP-FTFG  QGTKLEIK
Z46622 VL  AEDVAVYYCQ  QYYSTPSYTFG  QGTKLEIK
```

Alignment of the amino acid sequences of the mature ABC101 VL (SEQ ID NO:40), humanized ABC101 VL (HuABC101 VL) (SEQ ID NO:44), and human acceptor Z46622 VL (SEQ ID NO:48) regions.

Figure 13

```
NheI
GCTAGCACCACCATGGAGACAGACACACTCCTGCTATGGGTGCTGCTGCTCTGGGTTCCA
              M  E  T  D  T  L  L  W  V  L  L  L  W  V  P

GGTTCCACTGGTGACATTGTGATGACACAGTCTCCTGACTCCTTAGGCGTATCTCTGGGG
 G  S  T  G  D  I  V  M  T  Q  S  P  D  S  L  G  V  S  L  G

GAGAGGGCCACCATCAACTGCAGGGCCAGCCAAAGTGTCAGCACATCTAGCTATAGTTAT
 E  R  A  T  I  N  C  R  A  S  Q  S  V  S  T  S  S  Y  S  Y

GTTCACTGGTACCAACAGAAACCAGGACAGCCACCCAAACTCCTCATCAAGTATGCATCC
 V  H  W  Y  Q  Q  K  P  G  Q  P  P  K  L  L  I  K  Y  A  S

AACCTAGAATCTGGGGTCCCTGACAGGTTCAGCGGCTCTGGGTCTGGGACAGACTTCACC
 N  L  E  S  G  V  P  D  R  F  S  G  S  G  S  G  T  D  F  T

CTCACCATCAGCAGCCTGCAGGCTGAGGATGTGGCAGTCTATTACTGTCAGCACAGTTGG
 L  T  I  S  S  L  Q  A  E  D  V  A  V  Y  Y  C  Q  H  S  W

GACATTCCCTTCACATTCGGACAGGGGACCAAACTCGAAATCAAAC GTAAGTAGTCTTCT
 D  I  P  F  T  F  G  Q  G  T  K  L  E  I  K

EcoRI
CAGAATTC
```

Nucleotide sequence of the HuABC101 VL gene (SEQ ID NO:15) flanked by NheI and EcoRI sites (underlined) shown along with the deduced amino acid sequence (SEQ ID NO:16).

Figure 14

|  | D1 | D2 | Binding of ABC2 | ABC101 | ABC116 | Mik-β1 |
|---|---|---|---|---|---|---|
| HuD1/HuD2 | H | H | + | + | + | + |
| MoD1/MoD2 | M | M | - | - | - | - |
| HuD1/MoD2 | H | M | + | + | - | + |
| MoD1/HuD2 | M | H | - | - | + | - |
| HuD1 | H |  | + | - | - | + |
| HuD2 |  | H | - | - | + | - |

Figure 18

|  | Binding of | | |
| --- | --- | --- | --- |
| CD122 | ABC2 | ABC101 | Mik-β1 |
| Wild-type (SEQ ID NO:54) | + | + | + |
| W38K (SEQ ID NO:55) | + | + | + |
| P39S (SEQ ID NO:56) | + | + | +/- |
| D40A (SEQ ID NO:57) | + | + | + |
| R41A (SEQ ID NO:58) | + | + | - |
| R42A (SEQ ID NO:59) | - | + | + |
| R43A (SEQ ID NO:60) | - | + | + |
| W44A (SEQ ID NO:61) | + | + | + |
| L64A (SEQ ID NO:62) | + | + | + |
| G65A (SEQ ID NO:63) | + | + | + |
| G65T (SEQ ID NO:64) | - | - | + |
| A66S (SEQ ID NO:65) | + | + | + |
| S69A (SEQ ID NO:66) | + | + | + |
| Q70A (SEQ ID NO:67) | + | + | + |
| Q70K (SEQ ID NO:68) | + | - | + |
| K71A (SEQ ID NO:69) | + | + | + |
| S132A (SEQ ID NO:70) | + | + | + |
| H133A (SEQ ID NO:71) | + | - | + |
| Y134A (SEQ ID NO:72) | + | + | + |

Figure 19

Growth of TF-1 transfectants

| Transfected CD122 | In the presence of | | | |
|---|---|---|---|---|
| | No cytokine | IL-2 | IL-15/IL-15Rα complex | GM-CSF |
| None | - | - | - | + |
| Wild-type | - | + | + | + |
| R42A | - | - | - | + |
| R43A | - | + | + | + |
| G65T | - | - | - | + |
| H133A | - | - | - | + |

Figure 20

ANTIBODIES TO CD122

CROSS-REFERENCE TO RELATED APPLICATIONS

The present application is a nonprovisional and claims the benefit of 61/322,229 filed Apr. 8, 2010 and 61/360,405 filed Jun. 30, 2010, each incorporated by reference in its entirety for all purposes.

REFERENCE TO A SEQUENCE LISTING

The Sequence Listing written in file 57761431.txt is 105 kilobytes, and was created on Apr. 4, 2011 and is hereby incorporated by reference.

BACKGROUND

CD122 is a 525 amino acid-long type I membrane protein that is expressed on T cells, NK cells, monocytes and a subset of B cells (Zamai, et al, J. Biol. Regul. Homeost. Agents 15:95-97 (2001)). The CD122 molecule is an integral part of the receptor for interleukin 2 (IL-2) and interleukin 15 (IL-15), two type I cytokines. CD122, also referred to as the β chain of the IL-2 and IL-15 receptors, combines with other receptor subcomponents to generate receptors that exhibit precise cytokine specificity and affinity. Molecules that functionally associate with CD122 on the cell surface include CD25 (also known as the IL-2 receptor α chain or IL-2Rα), CD132 (also referred to as the common γ or $γ_c$ chain), and IL-15 receptor α chain (also referred to as IL-15Rα; not yet assigned a CD designation) (Waldmann, Nat. Rev. Immunol. 6:595-601 (2006)). CD122 in combination with CD132 forms a receptor that exhibits an intermediate level of affinity (intermediate affinity receptor) for both IL-2 (KD=~1 nM) and IL-15 (KD=~10 nM). CD122 associated with both CD25 and CD132 results in a receptor with high affinity (KD=~10 pM) specific for IL-2, while CD122 in combination with IL-15Rα and CD132 generates a high affinity receptor (KD=~10 pM) for IL-15 (Ma, A., et al., Annu. Rev. Immunol. 24: 657-679 (2006)).

IL-2 and IL-15 share the capacity to stimulate the proliferation of T lymphocytes, but each possesses unique activities in the maintenance of the immune system. IL-2 plays a role limiting T cell reactivity by priming activated T cells for apoptosis, whereas IL-15 is required for the development of NK cells and the development and maintenance of CD8+ memory T cells (Waldmann, Nat. Rev. Immunol. 6:595-601 (2006)). These two cytokines also exhibit a fundamental difference in the means by which they interact with their respective receptor components. IL-2 signaling occurs when the soluble cytokine interacts with either the intermediate or high affinity IL-2 receptor on the surface of a cell. This soluble cytokine delivery, in which a cytokine secreted by either the same or a distinct cell interacts with all receptor subcomponents on a single cell's surface, is the mechanism by which all type I cytokines, except IL-15, transmit their signals. In contrast, IL-15 signaling is carried out via presentation of IL-15 bound to IL-15Rα on the surface of one cell to another cell expressing the CD122 and CD132 molecules. This is referred to as trans-presentation. Trans-presentation is the mechanism by which IL-15 bound to the IL-15Rα receptor sub-component, or a fragment thereof, either soluble or bound to one cell, can be presented to a distinct cell expressing the remaining receptor subcomponents (CD122 and CD132) and resulting in IL-15 signaling. The affinity of isolated IL-15Rα, or fragments thereof, for IL-15 is high (KD=~10 pM) and it is believed that IL-15 and IL-15Rα associate in the endoplasmic reticulum and are transported to the cell surface as a complex for trans-presentation to other cells expressing CD122 and CD132 on the surface. Cis-presentation occurs when IL-15 interacts with CD122, CD132 and IL-15Rα that are expressed on the same cell. The vast majority of IL-15 signaling is mediated via trans-presentation, while cis-presentation plays a minor role, and little or no signaling occurs by the delivery of soluble IL-15 (Stonier and Schluns, Immunol. Lett. 127:85-92 (2010); Ma et al., Annu. Rev. Immunol. 24: 657-679 (2006); Dubois et al., Immunity 17:537-547 (2002)).

As well as sharing the basic structural similarities of the type I cytokines, some functional activities, and certain receptor subcomponents, IL-2 and IL-15 has each been associated with a variety of immune-mediated diseases. For instance, inhibition of IL-2 activity by targeting the α chain of the IL-2 receptor (CD25) with a monoclonal antibody is an effective immunomodulatory strategy that is currently approved for acute kidney transplant rejection (Vincenti et al., New Engl. J. Med. 338:161-5 (1998)). Additionally, therapeutic benefits of anti-CD25 approaches have also been reported in clinical trials that target asthma (Busse et al., Am. J. Respir. Crit. Care Med. 178:1002-1008 (2008)), uveitis (Yeh et al., J. Autoimmun. 31:91-97 (2008)) and multiple sclerosis (Rose et al., Neurology, 69:785-789 (2007)), implicating IL-2 involvement in these conditions. An IL-15-specific monoclonal antibody has been reported to have positive therapeutic effect in a clinical trial for rheumatoid arthritis (Baslund et al., Arthritis Rheum. 52:2686-2692 (2005)), and reported to have efficacy in animal models of psoriasis (Villadsen et al., J. Clin. Invest. 112:1571-1580 (2003)), celiac disease (Maiuri et al., Gastroenterology 119:996-1066 (2000)), and systemic lupus erythematosus (Bo et al., Scand. J. Immunol. 69:119-129 (2009)). Mouse monoclonal antibodies against human CD122 have been generated from mice immunized with human T cell lines and subsequently identified as being specific for the β chain of the IL-2 receptor by a variety of techniques (Tsudo et al., Proc. Natl. Acad. Sci. USA 86:1982-1986 (1989); Takeshita et al., J. Exp. Med. 169:1323-1332 (1989); Fung et al., J. Immunol. 147:1253-1260 (1991)). These anti-CD122 monoclonal antibodies inhibited IL-2-dependent proliferation on cells bearing the intermediate affinity IL-2 receptor, but they were not able to effectively inhibit IL-2-dependent proliferation on cells bearing the high affinity IL-2 receptor. Furthermore, no anti-CD122 monoclonal antibodies have been reported that effectively inhibit trans-presentation of IL-15.

One anti-CD122 antibody, Mik-β1 (Tsudo et al., Proc. Natl. Acad. Sci. USA 86:1982-1986 (1989)), has been tested as a therapy for T cell large granular lymphocyte leukemia (Morris et al., Proc. Nat. Acad. Sci. USA 103:401-406 (2006)). Mik-β1 has also been humanized, and this version, HuMik-β1 (Hakimi et al., J. Immunol. 151:1075-1085 (1993)) has been reported to prolong cardiac allografts in non-human primates (Tinubu et al., J. Immunol. 153: 4330-4338 (1994)).

SUMMARY OF THE CLAIMED INVENTION

The invention provides an isolated monoclonal antibody that specifically binds to CD122 and inhibits binding IL-2 and IL-15 to a receptor comprising CD122 and CD132. Some antibodies inhibit binding of IL-2 to a receptor comprising CD122, CD132 and CD25. Some antibodies inhibit binding of IL-15 presented in trans bound to an IL-15Rα to the receptor comprising CD122 and CD132. Some antibodies inhibit binding of IL-15 to a receptor comprising CD122, CD132 and IL-15Rα. Some antibodies inhibit binding in any or all of these situations by at least 30% when the antibody is present in no more than 100-fold molar excess with respect to the IL-2 or IL-15.

Some monoclonal antibodies' binding to CD122 is inhibited by substituting residue 42, 43, and/or 133 with alanine and/or residue 65 with threonine and/or residue 70 with lysine, residues being numbered as in SEQ ID NO:73. Some monoclonal antibodies' binding to CD122 is inhibited by substituting residue 42 and/or 43 with alanine and/or residue 65 with threonine residues being numbered as in SEQ ID NO:73. Some monoclonal antibodies' binding to CD122 is inhibited by substituting residues 65 with threonine and/or residue 70 with lysine and/or residue 133 with alanine residues being as numbered in SEQ ID NO:73 with alanine. Some monoclonal antibodies specifically bind to an epitope including residue 42 as numbered in SEQ ID NO:73. Some monoclonal antibodies specifically bind to an epitope including residue 65 as numbered in SEQ ID NO:73. Some monoclonal antibodies specifically bind to an epitope of CD122 including residue 133 of SEQ ID NO:73. Some monoclonal antibodies specifically bind to an epitope of CD122 including residue 42, 43, 65, 70 and/or 133 of SEQ ID NO:73. Some monoclonal antibodies specifically bind to an epitope of CD122 including residues 42, 43 and 65 of SEQ ID NO:73. Some monoclonal antibodies specifically bind to an epitope of CD122 including residues 65, 70 and 133 of SEQ NO:73. Some monoclonal antibodies specifically bind to an epitope of CD122 within fibronectin type III domain 1 of SEQ ID NO:73. Some monoclonal antibodies specifically bind to an epitope of CD122 within fibronectin type III domains 1 and 2 of SEQ ID NO:73. Some monoclonal antibodies' binding to CD122 is not detectably inhibited by substituting residue 39 or 41 numbered in SEQ ID NO:73 with alanine.

Some antibodies compete with antibody ABC2 characterized by a mature light chain variable region of SEQ ID NO:30 and a mature heavy chain variable region of SEQ ID NO:25, or ABC101, characterized by a mature light chain variable region of SEQ ID NO:40 and a mature heavy chain variable region of SEQ ID NO:35, for specific binding to CD122. Some antibodies bind to the same epitope on CD122 as ABC2 or ABC101. Some antibodies comprise three light chain CDRs and three heavy chain CDRs, wherein each CDR has at least 90% sequence identity to a corresponding CDR from ABC2 (SEQ ID NOS: 27-29 light chain and 22-24 heavy chain), or ABC101 (SEQ ID NOS. 37-39 light chain, 32-34 heavy chain). Some antibodies comprise three light chain CDRs and three heavy chain CDRs of ABC2 or ABC101.

Some antibodies are chimeric, humanized, veneered or human. Some antibodies have human IgG1 kappa isotype. An antibody can be an intact antibody or a single-chain antibody, Fab or F(ab')2 fragment.

The invention further provides humanized or chimeric ABC2 antibodies that specifically binds to CD122, wherein ABC2 is a mouse antibody characterized by a mature light chain variable region of SEQ ID NO:30 and mature heavy chain variable region of SEQ ID NO:25. Some such antibodies comprise a humanized light chain comprising three CDRs of the ABC2 light chain (SEQ ID NO:30) and a humanized heavy chain comprising three CDRs of the ABC2 heavy chain (SEQ ID NO:25).

Some antibodies comprise a humanized light chain at least 90% identical to SEQ ID NO:42 and a humanized heavy chain having an amino acid sequence at least 90% identical to SEQ ID NO:41. In some antibodies positions H28, H48, H49, H68, H93 and L71 by Kabat numbering are occupied by residues T, I, A, I, A and Y respectively. In some antibodies position H42 by Kabat numbering is occupied by G. In some antibodies, the light chain CDRs are SEQ ID NOS. 27-29 and the heavy chain CDRs are SEQ ID NOS:22-24.

The invention further provides humanized or chimeric ABC101 antibodies that specifically binds to CD122, wherein ABC101 is characterized by a mature light chain variable region of SEQ ID NO:40 and a mature heavy chain variable region of SEQ ID NO:35. Some such antibodies comprise a humanized light chain comprising three CDRs of SEQ ID NO:40 and a humanized heavy chain comprising three CDRs of SEQ ID NO:35. Some such antibodies comprise a humanized mature light chain variable region at least 90% identical to SEQ ID NO:44 and a humanized mature heavy chain variable region having an amino acid sequence at least 90% identical to SEQ ID NO.43. In some such antibodies positions H27, H30, H48, H66, H67, H71 and L49 by Kabat numbering are occupied by residues Y, T, M, Q, I, R and K respectively. In some such antibodies, the light chain CDRs are SEQ ID NOS. 37-39 and the heavy chain CDRs are SEQ ID NOS. 32-34.

The invention further provides a pharmaceutical composition comprising any of the above antibodies and a pharmaceutically acceptable carrier.

The invention further provides methods of suppressing an undesired immune response in a patient, comprising administering to a patient an effective regime of any of the above antibodies. In some methods, the patient has an autoimmune disease, such as, for example, sclerosis, rheumatoid arthritis, systemic lupus erythematosus, diabetes, psoriasis, celiac disease or uveitis. In some methods, the patient has asthma or allergy. In some methods, the patient has graft versus host disease. In some methods, the patient has host versus graft disease.

The invention further provides a method of treating a cancer in a patient, comprising administering to a patient an effective regime of any of the above antibodies. In some methods, the cancer expresses detectable CD122.

The invention further provides an isolated fragment of no more than 100 contiguous residues of SEQ ID NO:73 including one or more of residues 43, 65 and 133. Some isolated fragments include residues 43 and 65 of SEQ ID NO:73. Some isolated fragments include residues 65 and 133 of SEQ ID NO:73. Some isolated fragments include 10 or fewer contiguous residues of SEQ ID NO:73. Some such isolated fragments are linked to a carrier that helps elicit an antibody response to the fragment and/or as a component of a composition with an adjuvant that helps elicit an antibody response to the fragment.

BRIEF DESCRIPTION OF THE DRAWINGS

FIG. 3. The consensus cDNA sequence of ABC2 VH along with the deduced amino acid sequence.

FIG. 4. The consensus cDNA sequence ABC2 VL along with the deduced amino acid sequence.

FIG. 5. The consensus cDNA sequence of ABC101 VH along with the deduced amino acid sequence.

FIG. 6. The consensus cDNA sequence of ABC101 VL along with the deduced amino acid sequence.

FIG. 7. Alignment of the amino acid sequences of the mature ABC2 VH, humanized ABC2 VH (HuABC2 VH), and human acceptor DA430129 VH regions.

FIG. 8. The nucleotide and deduced amino acid sequences of the designed HuABC2 VH gene flanked by SpeI and HindIII sites.

FIG. 9. Alignment of the amino acid sequences of the mature ABC2 VL, humanized ABC2 VL (HuABC2 VL), and human acceptor M29469 VL regions.

FIG. 10. The nucleotide and deduced amino acid sequences of the designed HuABC2 VL gene flanked by NheI and EcoRI sites.

FIG. 11. Alignment of the amino acid sequences of the mature ABC101 VH, humanized ABC101 VH (HuABC101 VH), and human acceptor DA936142 VH regions.

FIG. 12. The nucleotide and deduced amino acid sequences of the designed HuABC101 VH gene flanked by SpeI and HindIII sites.

FIG. 13 Alignment of the amino acid sequences of the mature ABC101 VL, humanized ABC101 VL (HuABC101 VL), and human acceptor Z46622 VL regions.

FIG. 14. The nucleotide and deduced amino acid sequences of the designed HuABC101 VL gene flanked by NheI and EcoRI sites.

FIG. 18. Binding of ABC2, ABC101, ABC116 and Mik-β1 to various CD122 constructs.

FIG. 19. Binding of ABC2, ABC101 and Mik-β1 to various single amino acid substitution mutants of human CD122.

FIG. 20. Growth of TF-1 transfectants expressing the wild-type or mutant CD122 in the presence of GM-CSF, IL-2 or IL-15/IL-15Rα complex.

DEFINITIONS

Figure 1:
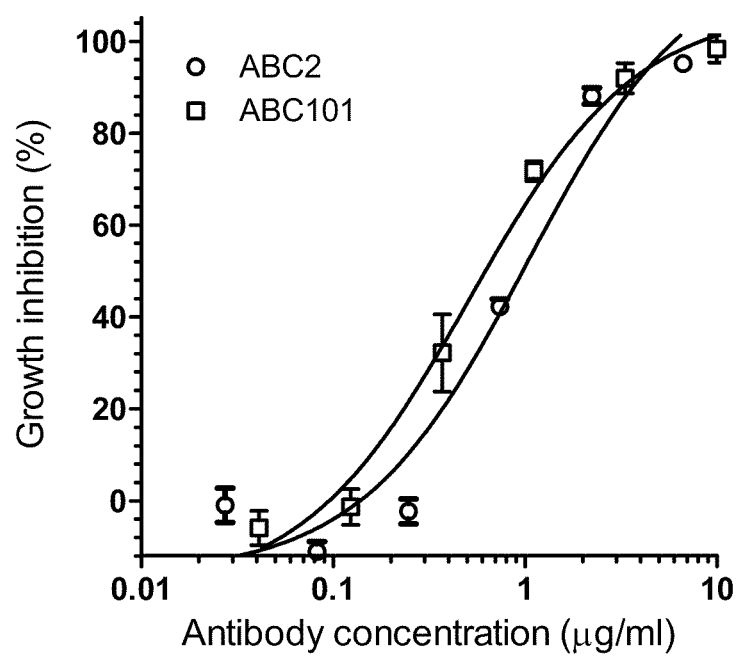
FIG. 1. Effects of ABC2 and ABC101 on trans-presentation of IL-15.

Monoclonal antibodies or other biological entities, such as a fragment of CD122) are typically provided in isolated form. This means that an antibody or other biologically entity is typically at least 50% w/w pure of interfering proteins and other contaminants arising from its production or purification but does not exclude the possibility that the monoclonal antibody is combined with an excess of pharmaceutical acceptable carrier(s) or other vehicle intended to facilitate its use. Sometimes monoclonal antibodies are at least 60, 70, 80, 90, 95 or 99% w/w pure of interfering proteins and contaminants from production or purification. Often an isolated monoclonal antibody or other biological entity is the predominant macromolecular species remaining after its purification.

Specific binding of a monoclonal antibody to its target antigen means an affinity of at least $10^6$, $10^7$, $10^8$, $10^9$, or $10^{10}$ $M^{-1}$. Specific binding is detectably higher in magnitude and distinguishable from non-specific binding occurring to at least one unrelated target. Specific binding can be the result of formation of bonds between particular functional groups or particular spatial fit (e.g., lock and key type) whereas nonspecific binding is usually the result of van der Waals forces. Specific binding does not however necessarily imply that a monoclonal antibody binds one and only one target.

When a mutation in CD122 inhibits specific binding of an antibody to CD122, the binding strength (whether assessed by composite signal, affinity constant, or other measure) is detectably lower (e.g., lowered beyond the standard error of the mean, SEM) to the mutated form than the wildtype form of CD122 (SEQ ID NO:73) and can be less than 50% or 10% of the binding to the wildtype form. The reduction in binding can also be assessed relative to the binding of a positive control antibody, such as the commercially available L5 anti-FLAG™ antibody used in the examples, which binds to a FLAG™ peptide linked to CD122. For example, a mutation inhibits binding of an anti-CD122 antibody if the antibody binds to mutated CD122 with less than 50% or preferably less than 10% the binding strength of the anti-FLAG antibody binding to the linked FLAG™ peptide.

The basic antibody structural unit is a tetramer of subunits. Each tetramer includes two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. This variable region is initially expressed linked to a cleavable signal peptide. The variable region without the signal peptide is sometimes referred to as a mature variable region. Thus, for example, a light chain mature variable region, means a light chain variable region without the light chain signal peptide. The carboxy-terminal portion of each chain defines a constant region primarily responsible for effector function.

Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 or more amino acids. (See generally, *Fundamental Immunology* (Paul, W., ed., 2nd ed. Raven Press, N.Y., 1989), Ch. 7) (incorporated by reference in its entirety for all purposes).

The mature variable regions of each light/heavy chain pair form the antibody binding site. Thus, an intact antibody has two binding sites. Except in bifunctional or bispecific antibodies, the two binding sites are the same. The chains all exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat, *Sequences of Proteins of Immunological Interest* (National Institutes of Health, Bethesda, Md., 1987 and 1991), or Chothia & Lesk, *J. Mol. Biol.* 196:901-917 (1987); Chothia et al., *Nature* 342:878-883 (1989). Kabat also provides a widely used numbering convention (Kabat numbering) in which corresponding residues between different heavy chains or between different light chains are assigned the same number.

The term "antibody" includes intact antibodies and binding fragments thereof. Typically, fragments compete with the intact antibody from which they were derived for specific binding to the target including separate heavy chains, light chains Fab, Fab', F(ab')$_2$, F(ab)c, Dabs, nanobodies, and Fv. Fragments can be produced by recombinant DNA techniques, or by enzymatic or chemical separation of intact immunoglobulins. The term "antibody" also includes a bispecific antibody. A bispecific or bifunctional antibody is an artificial hybrid antibody having two different heavy/light chain pairs and two different binding sites (see, e.g., Songsivilai and Lachmann, Clin. Exp. Immunol., 79:315-321 (1990); Kostelny et al., J. Immunol., 148:1547-53 (1992)).

The term "epitope" refers to a site on an antigen to which an antibody binds. An epitope can be formed from contiguous amino acids or noncontiguous amino acids juxtaposed by tertiary folding of one or more proteins. Epitopes formed from contiguous amino acids (also known as linear epitopes) are typically retained on exposure to denaturing solvents whereas epitopes formed by tertiary folding (also known as conformational epitopes) are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols, in Methods in Molecular Biology, Vol. 66, Glenn E. Morris, Ed. (1996).

Antibodies that recognize the same or overlapping epitopes can be identified in a simple immunoassay showing the ability of one antibody to compete with the binding of another antibody to a target antigen. The epitope of an antibody can also be defined X-ray crystallography of the antibody bound to its antigen to identify contact residues. Alternatively, two antibodies have the same epitope if all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Competition between antibodies is determined by an assay in which an antibody under test inhibits specific binding of a reference antibody to a common antigen (see, e.g., Junghans et al., Cancer Res. 50:1495, 1990). A test antibody competes with a reference antibody if an excess of a test antibody (e.g., at least 2×, 5×, 10×, 20× or 100×) inhibits binding of the reference antibody by at least 50% but preferably 75%, 90% or 99% as measured in a competitive binding assay. Antibodies identified by competition assay (competing antibodies) include antibodies binding to the same epitope as the reference antibody and antibodies binding to an adjacent epitope sufficiently proximal to the epitope bound by the reference antibody for steric hindrance to occur.

The term "patient" includes human and other mammalian subjects that receive either prophylactic or therapeutic treatment.

For purposes of classifying amino acids substitutions as conservative or nonconservative, amino acids are grouped as follows: Group I (hydrophobic side chains): met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): trp, tyr, phe. Conservative substitutions involve substitutions between amino acids in the same class. Non-conservative substitutions constitute exchanging a member of one of these classes for a member of another.

Percentage sequence identities are determined with antibody sequences maximally aligned by the Kabat numbering convention. After alignment, if a subject antibody region (e.g., the entire mature variable region of a heavy or light chain) is being compared with the same region of a reference antibody, the percentage sequence identity between the subject and reference antibody regions is the number of positions occupied by the same amino acid in both the subject and reference antibody region divided by the total number of aligned positions of the two regions, with gaps not counted, multiplied by 100 to convert to percentage.

Compositions or methods "comprising" one or more recited elements may include other elements not specifically recited. For example, a composition that comprises antibody may contain the antibody alone or in combination with other ingredients.

DETAILED DESCRIPTION

I. General

The invention provides monoclonal antibodies that specifically bind to CD122, which is one component of receptors for IL-2 and IL-15. The monoclonal antibodies have the capacity for substantial inhibition of both IL-2 and IL-15 mediated functions by inhibiting binding of these cytokines to their receptors. The monoclonal antibodies can be used for inhibiting undesired immune responses or treatment of cancer, among other applications.

II. Target Molecules

Unless otherwise indicated CD122 means human CD122. An exemplary human sequence is assigned Swiss Prot accession number P14784. Known natural allelic variants thereof include 10 L→V: dbSNP rs57770674, 83 S→F, dbSNP rs2228143 and 391 D→E: dbSNP rs228942. The complete human CD122 sequence has 551 amino acids of which amino acids 1-26 are a signal peptide. Approximately residues 27-240 constitute an extracellular domain. Approximately residues 241-265 constitute a transmembrane domain and approximately residues 266-551 constitute a cytoplasmic domain. Antibodies of the invention bind to epitopes within the extracellular domain of CD122.

Mutation residues are defined by reference to SEQ ID NO:73, the complete sequence, without signal sequence, of human CD122. If the actual form of CD122 used in a binding experiment is other than SEQ ID NO:73, (e.g., an N-terminal truncation of SEQ ID NO:73), mutants are the corresponding residues in whatever form of CD122 used when maximally aligned with SEQ ID NO:73.

CD122 forms receptors in combination with CD132, CD25 and/or IL-15Rα as discussed in the Background. In brief, the combination of a CD122 and CD132 constitutes a receptor with intermediate affinity for IL-2 and IL-15. The combination of CD122, CD132 and CD25 constitutes a receptor with high affinity for IL-2 and the combination of CD122, CD132 and IL-15Rα constitutes a receptor with high affinity for IL-15.

Unless otherwise indicated CD132, CD25 and/or IL-15Rα refer to the human forms of these proteins. An exemplary human sequence for human CD132 is designated Swiss Prot P31785, which is a protein of 369 amino acids of which approximately residues 1-22 are a signal peptide, 23-262 are an extracellular domain, 263-283 are a transmembrane domain and 284-369 are a cytoplasmic domain.

An exemplary human sequence for CD25 is designated Swiss Prot P01589, which is an amino acid sequence of 272 residues of which approximately residues 1-21 are a signal peptide, residues 22-240 are an extracellular domain, residues 241-259 are a transmembrane region and residues 260-272 are a cytoplasmic domain.

An exemplary human sequence for IL-15Rα is designated Swiss Prot Q13261, which is a protein of 267 residues of which approximately 1-30 are a signal peptide, 31-205 are an extracellular domain, 206-228 are a transmembrane region, and 229-267 are a cytoplasmic domain.

Unless otherwise apparent from the context, reference to one of the above receptors means at least the extracellular domain of the protein and usually the complete protein other than a cleavable signal peptide.

As discussed in the background, the above receptors bind to IL-2 and IL-15, the latter of which may be presented in cis or in trans. Unless otherwise apparent from the context, these molecules refer to the human forms of these proteins. An exemplary sequence for human IL-2 is designated Swiss Prot P60568, which is a protein sequence of 153 amino acids of which amino acids 1-20 are a signal peptide. An exemplary sequence for human IL-15 is designated Swiss Prot P40933, which is a protein of 162 amino acids of which amino acids 1-29 are a signal peptide. Unless other apparent from the context, reference to IL-2 or IL-15 means the mature protein from which the signal sequence has been removed.

III. Antibodies of the Invention

A. Binding Specificity and Functional Properties

The invention provides monoclonal antibodies binding to epitopes within the CD122 protein. Antibodies designated ABC2 and ABC101 are two such exemplary mouse antibodies. Both ABC2 and ABC101 specifically bind to human CD122. ABC2 and ABC101 and some other antibodies of the invention are further characterized by specific binding to cynomologus CD122 and lack of significant binding to mouse and dog CD122. Binding to CD122 can be demonstrated to CD122 alone and/or any of the receptors incorporating CD122 discussed above. The monoclonal antibodies of the invention are characterized in that a monoclonal antibody as a single agent has a capacity to substantially inhibit receptors incorporating the CD122 from binding to and signaling for cell proliferation in response to both IL-2 and IL-15.

Preferred antibodies inhibit binding of both low and high affinity receptors incorporating CD122 to both IL-2 and IL-15 and can inhibit IL-15 binding both in cis and in trans. Such antibodies are distinguished from previously reported antibodies to CD122 including Mik-β1 and its humanized form. As shown in Example 8, HuMik-β1 shows only weak ability to inhibit soluble IL-15-mediated proliferation of cells bearing CD122 and no detectable ability to inhibit IL-2-mediated proliferation of cells bearing the high affinity IL-2 receptor including CD122. Mik-β1, its humanized form and other known antibodies to CD122 also lack any or at least substantial ability to inhibit IL-15 presented in trans.

Inhibition may be demonstrated in a binding assay in which a receptor incorporating CD122 is expressed on cells and binds to IL-2 or IL-15 in the presence of an antibody being tested. Alternatively, or additionally, inhibition can be demonstrated by expressing a receptor incorporating CD122 on appropriate cells in the presence of IL-2 or IL-15 and assessing an effect of a monoclonal antibody on IL-2 or IL-15-mediated proliferation of the cells. Inhibition of IL-15 can be tested in cis or in trans in such formats. Exemplary assay formats for showing inhibition are provided in the examples. Optionally, inhibition of a test antibody can be demonstrated in comparison to an irrelevant control antibody not binding to CD122 or its receptor co-components or to IL-2 and IL-15, or to vehicle lacking any antibody.

Substantial inhibition means an inhibition of at least, 25, 30, 40, 50, or 75%, (e.g., 25-75% or 30-70%) of binding, cell proliferation and/or other functional activity mediated by IL-2 or IL-15. Inhibition is usually demonstrated when the antibody is at no more than 100-fold molar excess (e.g., 2-50 or 2-10 or 2-5 fold molar excess) with respect to the IL-2 or IL-15 ligand. For functional assays, IL-2 or IL-15 is typically present at the minimum level needed to stimulate full functional activity in the absence of antibody under test. Antibodies are usually present at a concentration between 50 nM and 5 µM. Preferred antibodies show inhibition of at least 40% of IL-2 interaction with low or high affinity receptors (or both), and at least 40% for IL-15 presented in cis and in trans. The extent of inhibition can also be quantified by the antibody concentration required for 50% inhibition of proliferation (IC50) mediated by trans-presentation of IL-15 to TF-1β cells as described in Examples 2 and 8. An antibody concentration less than 2 µg/ml and preferably less 1 µg/ml, for example about 0.1 to 1 or 0.5 to 1 µg/ml is preferred. Additionally, the antibody concentration required for 50% inhibition of IL-2-mediated TF-1αβ proliferation to cells bearing a high affinity IL-2 receptor as described in Example 8 is preferably less than 100 or 50 µg/ml, for example 10-50 µg/ml.

As is evident from these results the IC50 of an antibody of the invention depends on the nature of the interaction being inhibited. For cells that have the high affinity IL-2 receptor, it is much more difficult for an anti-CD122 to inhibit IL-2 (i.e., higher concentration of the same antibody needed) than to inhibit IL-15 trans-presentation. For cells that have only the intermediate affinity IL-2 receptor, it is harder to inhibit (i.e., higher concentration of the same antibody needed) IL-15 trans-presentation than to inhibit soluble IL-2 or IL-15.

Preferred antibodies also inhibit an immune disorder or cancer as shown in an animal model or clinical trial. An animal model of testing activity against graft versus host disease is discussed in the Examples. Some other examples of animal models are discussed in the Background section. One of such models is the SCID/psoriasis model described by Villadsen et al., supra. Anti-human CD122 antibodies that cross-react with monkey CD122 can be tested in organ transplantation in non-human primates (Tinubu et al, supra). Animal models of cancer in which human cancer cells are injected into an immunodeficient laboratory animal, such as a mouse or rat, are widely available.

Some antibodies of the invention bind to the same or overlapping epitope as an antibody designated ABC2 or ABC101. The sequences of the heavy and light chain mature variable regions of these antibodies are designated SEQ ID NOS. 25 and 30, and 35 and 40 respectively. Other antibodies having such a binding specificity can be produced by immunizing mice with CD122 or a portion thereof including the desired epitope, and screening resulting antibodies for binding to CD122, optionally in competition with ABC2 or ABC101. Antibodies identified by such assays can then be screened for ability to inhibit both IL-2 and IL-15 interactions as described in the examples, or otherwise. Antibodies can also be screened against mutagenized forms of the CD122 antigen to identify an antibody showing the same or similar binding profile to collection of mutational changes as ABC2 or ABC101. The mutations can be systematic replacement substitution with alanine (or serine if an alanine is present already) one residue at a time, or more broadly spaced intervals, throughout the extracellular domain of CD122 antibody or through a section thereof in which an epitope is known to reside.

Mutations at residues 42, 43 and 65 of SEQ ID NO:73 inhibit specific binding of ABC2 to CD122 (e.g., <10% binding of a positive control anti-FLAG antibody as described as the examples). Likewise mutations at residues 65, 70 and 133 of SEQ ID NO:73 inhibit specific binding of ABC101 to CD122. Because relatively few residues affect binding and the residues are spaced more broadly than a typical linear epitope (e.g., 3-20 contiguous amino acids), these results provide an indication that ABC101 and possibly ABC2 binds to a conformational epitope. Alternatively, one or more of the residues affecting binding may do so allosterically without direct contact with the antibody. The observation that mutagenesis of residue 65 with threonine but not alanine inhibits binding provides an indication that this residue may be affecting binding allosterically. Other antibodies binding to an epitope including one or more of residues 42, 43, 65, 70 and 133 of SEQ ID NO:73, and particularly to an epitope including one or more of residues 42, 65 and 133, are likely to share useful inhibitory properties with ABC2 and ABC101. Thus, antibodies whose specific binding is inhibited by mutagenesis of one or more residues 42, 43 and 65 and particularly residues 42 and 65 of SEQ ID NO:73 are likely to share similar properties to ABC2. Some such antibodies bind to an epitope that includes or consists of residue 42, 43 and/or 65 of SEQ ID NO:73. Some such antibodies bind to an epitope that includes or consists of residues 42 and 43 and in which residue 65 affects binding of the antibody allosterically. The epitope can be linear, such as an epitope (e.g., 2-5, 3-5, 3-10, 3-15, 3-20, 5-10, 5-15 or 5-20 contiguous amino acids) including or consisting of 1, 2, or all 3 of the specified amino acids (42, 43 and 65) or be conformational including or consisting of 1, 2, or all 3 of the specified amino acids. Antibodies whose specific binding is inhibited by mutagenesis at 1, 2 or all 3 of residues 65, 70 and 133 of SEQ ID NO:73 are likely to show similar inhibitory properties to ABC101. Some such antibodies bind to an epitope that includes or consists of residue 65 or 133 of SEQ ID NO:73 or both. Such an epitope can be linear such as an epitope (e.g., 2-5, 3-5, 3-10, 3-15, 3-20, 5-10, 5-15 or 5-20 contiguous amino acids) including or consisting of 1, 2 or all 3 of the specified amino acids (65, 70, and 133) or be conformational including or consisting of 1, 2 or all 3 of the specified amino acids. Some antibodies of the invention specifically bind to CD122 without such binding being substantially inhibited (e.g., binding at least 50% of a positive control antibody as described in the Examples) by substitution of residue 39 or 41 of SEQ ID NO:73 with alanine. (Mutation of residue 39 and 41 inhibits binding of the Mik-β1 antibody.) Any of the above described antibody types includes antibodies that specifically bind to an epitope not including residue 39 or 41 of SEQ ID NO:73 or, put another way, whose binding to CD122 is not detectably inhibited by substitution of these residues (binding above 50% of positive control anti-FLAG antibody as described in the examples).

Antibodies binding to an epitope that includes one or more specified residues can be generated by immunizing with a fragment of CD122 that includes these one or more residues. The fragment can for example have no more than 100, 50, 25, 10 or 5 contiguous amino acids from SEQ ID NO:73. Such fragments usually have at least 5, 6, 7, 8 or 9 contiguous residues of SEQ ID NO:73. The fragments can be linked to a carrier that helps elicit an antibody response to the fragment and/or be combined with an adjuvant that helps elicit such a response. Alternatively, antibodies binding to a desired residue can be obtained by immunizing with a full-length CD122 (other than signal sequence) or full length extracellular domain (other than signal sequence) of fibronectin III domain 1 and/or 2. Such antibodies can then be screened for differential binding to hybrids of human and mouse CD122 or differential binding to wildtype CD122 compared with mutants of specified residues. The screen against hybrids of human and mouse CD122 maps antibody binding to certain domains within CD122, such as fibronectin III domain 1 and/or 2. The screen against mutants more precisely defines the binding specificity to allow identification of antibodies whose binding is inhibited by mutagenesis of residues 43, 43, 65, 70 and/or 133 and which are likely to share inhibitor properties of the exemplified antibodies.

Antibodies having the binding specificity of a selected murine antibody (e.g., ABC2 or ABC101) can also be produced using a variant of the phage display method. See Winter, WO 92/20791. This method is particularly suitable for producing human antibodies. In this method, either the heavy or light chain variable region of the selected murine antibody is used as a starting material. If, for example, a light chain variable region is selected as the starting material, a phage library is constructed in which members display the same light chain variable region (i.e., the murine starting material) and a different heavy chain variable region. The heavy chain variable regions can for example be obtained from a library of rearranged human heavy chain variable regions. A phage showing strong specific binding for CD122 (e.g., at least $10^8$ and preferably at least $10^9$ $M^{-1}$) is selected. The heavy chain variable region from this phage then serves as a starting material for constructing a further phage library. In this library, each phage displays the same heavy chain variable region (i.e., the region identified from the first display library) and a different light chain variable region. The light chain variable regions can be obtained for example from a library of rearranged human variable light chain regions. Again, phage showing strong specific binding for CD122 are selected. The resulting antibodies usually have the same or similar epitope specificity as the murine starting material.

Other antibodies can be obtained by mutagenesis of cDNA encoding the heavy and light chains of an exemplary antibody, such as ABC2 or ABC101. Monoclonal antibodies that are at least 90%, 95% or 99% identical to ABC2 or ABC101 in amino acid sequence of the mature heavy and/or light chain variable regions and maintain its functional properties, and/or which differ from the respective antibody by a small number of functionally inconsequential amino acid substitutions (e.g., conservative substitutions), deletions, or insertions are also included in the invention. Monoclonal antibodies having at least one and preferably all six CDR(s) as defined by Kabat that are 90%, 95%, 99% or 100% identical to corresponding CDRs of ABC2 or ABC101 are also included.

B. Non-Human Antibodies

The production of other non-human monoclonal antibodies, e.g., murine, guinea pig, primate, rabbit or rat, against CD122 can be accomplished by, for example, immunizing the animal with CD122 or a fragment thereof, or cells bearing CD122, optionally co-expressed with its co-receptor proteins as discussed above. See Harlow & Lane, *Antibodies, A Laboratory Manual* (CSHP NY, 1988) (incorporated by reference for all purposes). Such an immunogen can be obtained from a natural source, by peptide synthesis or by recombinant expression. Optionally, the immunogen can be administered fused or otherwise complexed with a carrier protein. Optionally, the immunogen can be administered with an adjuvant. Several types of adjuvant can be used as described below. Complete Freund's adjuvant followed by incomplete adjuvant is preferred for immunization of laboratory animals. Rabbits or guinea pigs are typically used for making polyclonal antibodies. Mice are typically used for making monoclonal antibodies. Antibodies are screened for specific binding to CD122. Optionally, antibodies are further screened for binding to a specific region of CD122. Such screening can be accomplished by determining binding of an antibody to a collection of deletion mutants of CD122 and determining which deletion mutants bind to the antibody. Binding can be assessed, for example, by Western blot, FACS or ELISA.

C. Humanized Antibodies

A humanized antibody is a genetically engineered antibody in which the CDRs from a non-human "donor" antibody are grafted into human "acceptor" antibody sequences (see, e.g., Queen, U.S. Pat. Nos. 5,530,101 and 5,585,089; Winter, U.S. Pat. No. 5,225,539, Carter, U.S. Pat. No. 6,407,213, Adair, U.S. Pat. Nos. 5,859,205 6,881,557, Foote, U.S. Pat. No. 6,881,557). The acceptor antibody sequences can be, for example, a mature human antibody sequence, a composite of such sequences, a consensus sequence of human antibody sequences, or a germline region sequence. Thus, a humanized antibody is an antibody having some or all CDRs entirely or substantially from a donor antibody and variable region framework sequences and constant regions, if present, entirely or substantially from human antibody sequences. Similarly a humanized heavy chain has at least one, two and usually all three CDRs entirely or substantially from a donor antibody heavy chain, and a heavy chain variable region framework sequence and heavy chain constant region, if present, substantially from human heavy chain variable region framework and constant region sequences. Similarly a humanized light chain has at least one, two and usually all three CDRs entirely or substantially from a donor antibody light chain, and a light chain variable region framework sequence and light chain constant region, if present, substantially from human light chain variable region framework and constant region sequences. Other than nanobodies and dAbs, a humanized antibody comprises a humanized heavy chain and a humanized light chain. A CDR in a humanized antibody is substantially from a corresponding CDR in a non-human antibody when at least 85%, 90%, 95% or 100% of corresponding residues (as defined by Kabat) are identical between the respective CDRs. The variable region framework sequences of an antibody chain or the constant region of an antibody chain are substantially from a human variable region framework sequence or human constant region respectively when at least 85, 90, 95 or 100% of corresponding residues defined by Kabat are identical.

Although humanized antibodies often incorporate all six CDRs (preferably as defined by Kabat) from a mouse antibody, they can also be made with less than all CDRs (e.g., at least 3, 4, or 5) CDRs from a mouse antibody (e.g., Pascalis et al., J. Immunol. 169:3076, 2002; Vajdos et al., Journal of Molecular Biology, 320: 415-428, 2002; Iwahashi et al., Mol. Immunol. 36:1079-1091, 1999; Tamura et al, Journal of Immunology, 164:1432-1441, 2000).

In some antibodies only part of the CDRs, namely the subset of CDR residues required for binding, termed the SDRs, are needed to retain binding in a humanized antibody. CDR residues not contacting antigen and not in the SDRs can be identified based on previous studies (for example residues H60-H65 in CDR H2 are often not required), from regions of Kabat CDRs lying outside Chothia hypervariable loops (Chothia, J. Mol. Biol. 196:901, 1987), by molecular modeling and/or empirically, or as described in Gonzales et al., Mol. Immunol. 41: 863, 2004. In such humanized antibodies at positions in which one or more donor CDR residues is absent or in which an entire donor CR is omitted, the amino acid occupying the position can be an amino acid occupying the corresponding position (by Kabat numbering) in the acceptor antibody sequence. The number of such substitutions of acceptor for donor amino acids in the CDRs to include reflects a balance of competing considerations. Such substitutions are potentially advantageous in decreasing the number of mouse amino acids in a humanized antibody and consequently decreasing potential immunogenicity. However, substitutions can also cause changes of affinity, and significant reductions in affinity are preferably avoided. Positions for substitution within CDRs and amino acids to substitute can also be selected empirically.

The human acceptor antibody sequences can optionally be selected from among the many known human antibody sequences to provide a high degree of sequence identity (e.g., 65-85% identity) between a human acceptor sequence variable region frameworks and corresponding variable region frameworks of a donor antibody chain.

Certain amino acids from the human variable region framework residues can be selected for substitution based on their possible influence on CDR conformation and/or binding to antigen. Investigation of such possible influences is by modeling, examination of the characteristics of the amino acids at particular locations, or empirical observation of the effects of substitution or mutagenesis of particular amino acids.

For example, when an amino acid differs between a murine variable region framework residue and a selected human variable region framework residue, the human framework amino acid can be substituted by the equivalent framework amino acid from the mouse antibody when it is reasonably expected that the amino acid:

(1) noncovalently binds antigen directly,
(2) is adjacent to a CDR region,
(3) otherwise interacts with a CDR region (e.g. is within about 6 Å of a CDR region).

Other candidates for substitution are acceptor human framework amino acids that are unusual for a human immunoglobulin at that position. These amino acids can be substituted with amino acids from the equivalent position of the mouse donor antibody or from the equivalent positions of more typical human immunoglobulins. Other candidates for substitution are acceptor human framework amino acids that are unusual for a human immunoglobulin at that position.

An exemplary humanized antibody of the invention is a humanized form of ABC2, characterized by a mature light chain variable region of SEQ ID NO:42 and a mature heavy chain variable region of SEQ ID NO:41 and designated HuABC2. The invention also provides variants of HuABC2. Such variants typically differ from the sequences of HuABC2 by a small number (e.g., typically no more than 1, 2, 3, 5 or 10) of replacements, deletions or insertions. Such differences are usually in the framework but can also occur in the CDRs. For example, only a subset of substitutions at positions H28, H48, H49, H68, H93 and L71 can be made. Many of the framework residues not in contact with the CDRs in the humanized mAb can accommodate substitutions of amino acids from the corresponding positions of the donor mouse mAb or other mouse or human antibodies, and even many potential CDR-contact residues are also amenable to substitution or even amino acids within the CDRs may be altered. One example of a CDR substitution is to substitute a residue in a CDR with the residue occupying the corresponding position of the human acceptor sequence used to supply variable region frameworks.

Often the replacements made in the variant humanized ABC2 sequences are conservative with respect to the replaced HuABC2 amino acids. Preferably, replacements in HuABC2 (whether or not conservative) have no substantial effect on the binding affinity or potency of the humanized mAb, that is, its ability to inhibit interactions between receptors including CD122 and IL-2 and IL-15 (e.g., the potency in some or all of the assays described in the present examples or Background of the variant humanized ABC2 antibody is essentially the same, i.e., within experimental error, as that of HuABC2). Preferably the mature variant light and heavy chain V region sequences are at least 90%, more preferably at least 95%, and most preferably at least 98% identical to the respective HuABC2 mature light and heavy chain V regions. Alternatively, other human antibody acceptor sequences, particularly those with high sequence identity to the variable region framework sequences of ABC2 are also suitable to provide the humanized antibody variable regions framework sequences.

In some variants of HuABC2, at least 1, 2, 3, 4, 5 or all 6 of the positions of acceptor to donor substitutions mentioned in connection with the exemplified antibody (i.e., H28, H48, H49, H68, H93, and L71) are preferably occupied by residues T, I, A, I, A, and Y respectively (the residues occupying the corresponding position of the mouse donor antibody heavy chain). In some variants, position H42 is occupied by a G. If the heavy chain acceptor sequence is other than the sequence encoded by DA430129 cDNA (GenBank accession number), or the light chain acceptor sequence is other than the sequence encoded by M29469 cDNA (GenBank accession number), an acceptor to donor substitution may or may not be required for the specified occupancy of a particular variable framework region position depending on whether the residue occupying the specified position is already the same between the acceptor and donor.

Another exemplary humanized antibody of the invention is a humanized form of ABC101, characterized by a mature light chain variable region of SEQ ID NO:44 and a mature heavy chain variable region of SEQ ID NO:43 and designated HuABC101. The invention also provides variants of HuABC101. Such variants typically differ from the sequences of HuABC101 by a small number (e.g., typically no more than 1, 2, 3, 5 or 10) of replacements, deletions or insertions. Such differences are usually in the framework but can also occur in the CDRs. For example, only a subset of substitutions at positions H27, H30, H48, H66, H67, H71 and L49 can be made. Many of the framework residues not in contact with the CDRs in the humanized antibody can accommodate substitutions of amino acids from the corresponding positions of the donor mouse antibody or other mouse or human antibodies, and even many potential CDR-contact residues are also amenable to substitution or even amino acids within the CDRs may be altered. One example of a CDR substitution is to substitute a residue in a CDR with the residue occupying the corresponding position of the human acceptor sequence used to supply variable region frameworks.

Often the replacements made in the variant humanized ABC101 sequences are conservative with respect to the replaced HuABC101 amino acids. Preferably, replacements in HuABC101 (whether or not conservative) have no substantial effect on the binding affinity or potency of the humanized mAb, that is, its ability to inhibit interactions between receptors including CD122 and IL-2 and IL-15 (e.g., the potency in some or all of the assays described herein of the variant humanized ABC101 antibody is essentially the same, i.e., within experimental error, as that of HuABC101). Preferably the mature variant light and heavy chain V region sequences are at least 90%, more preferably at least 95%, and most preferably at least 98% identical to the respective HuABC101 mature light and heavy chain V regions. Alternatively, other human antibody variable region framework acceptor sequences, particularly those with high sequence identity to the variable region framework sequences of ABC101 are also suitable to provide the humanized antibody framework.

In some variants of HuABC101, at least 1, 2, 3, 4, 5, 6 or all 7 of the positions of acceptor to donor substitutions mentioned in connection with the exemplified antibody (i.e., H27, H30, H48, H66, H67, H71 and L49) are preferably occupied by residues Y, T, M, Q, I, R and K respectively (the residues occupying the corresponding position of the mouse donor antibody heavy chain). If the heavy chain acceptor sequence is other than the sequence encoded by DA936142 cDNA (GenBank accession number), or the light chain acceptor sequence is other than the sequence encoded by Z46622 cDNA (GenBank accession number), an acceptor to donor substitution may or may not be required for the specified occupancy of a particular variable framework region position depending on whether the residue occupying the specified position is already the same between the acceptor and donor.

D. Chimeric and Veneered Antibodies

The invention further provides chimeric and veneered forms of non-human antibodies, particularly the ABC2 and ABC101 antibodies of the examples.

A chimeric antibody is an antibody in which the mature variable regions of light and heavy chains of a non-human antibody (e.g., a mouse) are combined with human light and heavy chain constant regions. Such antibodies substantially or entirely retain the binding specificity of the mouse antibody, and are about two-thirds human sequence.

A veneered antibody is a type of humanized antibody that retains some and usually all of the CDRs and some of the non-human variable region framework residues of a non-human antibody but replaces other variable region framework residues that may contribute to B- or T-cell epitopes, for example exposed residues (Padlan, Mol. Immunol. 28:489, 1991) with residues from the corresponding positions of a human antibody sequence. The result is an antibody in which the CDRs are entirely or substantially from a non-human antibody and the variable region frameworks of the non-human antibody are made more human-like by the substitutions. Veneered forms of either the ABC2 or ABC 101 antibody are included in the invention.

E. Human Antibodies.

Human antibodies against CD122 are provided by a variety of techniques described below. Some human antibodies are selected by competitive binding experiments, by the phage display method of Winter, above, or otherwise, to have the same epitope specificity as a particular mouse antibody, such as one of the mouse monoclonals described in the examples. Human antibodies can also be screened for a particular epitope specificity by using only a fragment of CD122 as the target antigen, and/or by screening antibodies against a collection of deletion mutants of CD122.

Methods for producing human antibodies include the trioma method of Oestberg et al., *Hybridoma* 2:361-367 (1983); Oestberg, U.S. Pat. No. 4,634,664; and Engleman et al., U.S. Pat. No. 4,634,666, use of transgenic mice including human immunoglobulin genes (see, e.g., Lonberg et al., WO93/12227 (1993); U.S. Pat. No. 5,877,397, U.S. Pat. No. 5,874,299, U.S. Pat. No. 5,814,318, U.S. Pat. No. 5,789,650, U.S. Pat. No. 5,770,429, U.S. Pat. No. 5,661,016, U.S. Pat. No. 5,633,425, U.S. Pat. No. 5,625,126, U.S. Pat. No. 5,569, 825, U.S. Pat. No. 5,545,806, *Nature* 148, 1547-1553 (1994), *Nature Biotechnology* 14, 826 (1996), Kucherlapati, WO 91/10741 (1991) and phage display methods (see, e.g., Dower et al., WO 91/17271 and McCafferty et al., WO 92/01047, U.S. Pat. No. 5,877,218, U.S. Pat. No. 5,871,907, U.S. Pat. No. 5,858,657, U.S. Pat. No. 5,837,242, U.S. Pat. No. 5,733, 743 and U.S. Pat. No. 5,565,332.

F. Selection of Constant Region

The heavy and light chain variable regions of chimeric, humanized (including veneered), or human antibodies can be linked to at least a portion of a human constant region. The choice of constant region depends, in part, whether antibody-dependent complement and/or cellular mediated cytotoxicity is desired. For example, human isotypes IgG1 and IgG3 have complement-mediated cytotoxicity and human isotypes IgG2 and IgG4 do not. Light chain constant regions can be lambda or kappa. Antibodies can be expressed as tetramers containing two light and two heavy chains, as separate heavy chains, light chains, as Fab, Fab', F(ab')2, and Fv, or as single chain antibodies in which heavy and light chain variable domains are linked through a spacer.

Human constant regions show allotypic variation and isoallotypic variation between different individuals, that is, the constant regions can differ in different individuals at one or more polymorphic positions. Isoallotypes differ from allotypes in that sera recognizing an isoallotype binds to a non-polymorphic region of a one or more other isotypes. Reference to a human constant region includes a constant region with any natural allotype or any permutation of residues occupying polymorphic positions in natural allotypes.

One or several amino acids at the amino or carboxy terminus of the light and/or heavy chain, such as the C-terminal lysine of the heavy chain, may be missing or derivatized in a proportion or all of the molecules. Substitutions can be made in the constant regions to reduce or increase effector function such as complement-mediated cytotoxicity or ADCC (see, e.g., Winter et al., U.S. Pat. No. 5,624,821; Tso et al., U.S. Pat. No. 5,834,597; and Lazar et al., Proc. Natl. Acad. Sci. USA 103:4005, 2006), or to prolong half-life in humans (see, e.g., Hinton et al., J. Biol. Chem. 279:6213, 2004). Exemplary substitutions include a Gln at position 250 and/or a Leu at position 428 (EU numbering) for increasing the half life of an antibody. Substitution any of positions 234, 235, 236 and/or 237 reduce affinity for Fcγ receptors, particularly FcγRI receptor (see, e.g., U.S. Pat. No. 6,624,821). Optionally, positions 234, 236 and/or 237 in human IgG2 are substituted with alanine and position 235 with glutamine. (See, e.g., U.S. Pat. No. 5,624,821.)

H. Expression of Recombinant Antibodies

Chimeric, humanized (including veneered) and human antibodies are typically produced by recombinant expression. Recombinant polynucleotide constructs typically include an expression control sequence operably linked to the coding sequences of antibody chains, including naturally-associated or heterologous promoter regions. Preferably, the expression control sequences are eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the crossreacting antibodies.

Mammalian cells are a preferred host for expressing nucleotide segments encoding immunoglobulins or fragments thereof. See Winnacker, From Genes to Clones, (VCH Publishers, NY, 1987). A number of suitable host cell lines capable of secreting intact heterologous proteins have been developed in the art, and include CHO cell lines, various COS cell lines, HeLa cells, HEK293 cells, L cells, and non-antibody-producing myelomas including Sp2/0 and NS0. Preferably, the cells are nonhuman. Expression vectors for these cells can include expression control sequences, such as an origin of replication, a promoter, an enhancer (Queen et al., Immunol. Rev. 89:49 (1986)), and necessary processing information sites, such as ribosome binding sites, RNA splice sites, polyadenylation sites, and transcriptional terminator sequences. Preferred expression control sequences are promoters derived from endogenous genes, cytomegalovirus, SV40, adenovirus, bovine papillomavirus, and the like. See Co et al., J. Immunol. 148:1149 (1992).

Once expressed, antibodies can be purified according to standard procedures of the art, including HPLC purification, column chromatography, gel electrophoresis and the like (see generally, Scopes, *Protein Purification* (Springer-Verlag, NY, 1982)).

IV. Therapeutic Applications

The antibodies can be used for suppressing various undesirable immune response including those in which antibodies inhibiting interactions of IL-2 or IL-15 individually have been used.

One category of immune disorders treatable by antibodies of the invention is transplant rejection. When allogeneic cells or organs (e.g., skin, kidney, liver, heart, lung, pancreas and bone marrow) are transplanted into a host (i.e., the donor and donee are different individual from the same species), the host immune system is likely to mount an immune response to foreign antigens in the transplant (host-versus-graft disease) leading to destruction of the transplanted tissue. The monoclonal antibodies of the present invention are useful, inter alia, to block alloantigen-induced immune responses in the donee.

A related use for monoclonal antibodies of the present invention is in modulating the immune response involved in "graft versus host" disease (GVHD). GVHD is a potentially fatal disease that occurs when immunologically competent cells are transferred to an allogeneic recipient. In this situation, the donor's immunocompetent cells may attack tissues in the recipient. Tissues of the skin, gut epithelia and liver are frequent targets and may be destroyed during the course of GVHD. The disease presents an especially severe problem when immune tissue is being transplanted, such as in bone marrow transplantation; but less severe GVHD has also been reported in other cases as well, including heart and liver transplants.

A further situation in which immune suppression is desirable is in treatment of autoimmune diseases such as type 1 diabetes, Crohn's disease, ulcerative colitis, multiple sclerosis, stiff man syndrome, rheumatoid arthritis, myasthenia gravis and lupus erythematosus. In these disease, the body develops a cellular and/or humoral immune response against one of its own antigens leading to destruction of that antigen, and potentially crippling and/or fatal consequences. Autoimmune diseases are treated by administering one of the monoclonal antibodies of the invention.

Other immune disorders treatable by the monoclonal antibodies of the invention, include asthma, allergies, celiac disease, psoriasis, and uveitis. Celiac disease, psoriasis and uveitis are autoimmune diseases.

Other disorders treatable by monoclonal antibodies of the invention include cancers, particularly hematological malignancies, such as leukemia (e.g., T cell large granular lymphocyte leukemia) or lymphoma. Some such cancers show detectable levels of CD122 measured at either the protein (e.g., by immunoassay using one of the exemplified antibodies) or mRNA level. Some such cancers show elevated levels of CD122 relative to noncancerous tissue of the same type, preferably from the same patient. Optionally, a level of CD122 in a cancer is measured before performing treatment.

Monoclonal antibodies are administered in an effective regime meaning a dosage, route of administration and frequency of administration that delays the onset, reduces the severity, inhibits further deterioration, and/or ameliorates at least one sign or symptom of a disorder. If a patient is already suffering from a disorder, the regime can be referred to as a therapeutically effective regime. If the patient is at elevated risk of the disorder relative to the general population but is not yet experiencing symptoms, the regime can be referred to as a prophylactically effective regime. In some instances, therapeutic or prophylactic efficacy can be observed in an individual patient relative to historical controls or past experience in the same patient. In other instances, therapeutic or prophylactic efficacy can be demonstrated in a preclinical or clinical trial in a population of treated patients relative to a control population of untreated patients.

Exemplary dosages for a monoclonal antibody are 0.1-20, or 0.5-5 mg/kg body weight (e.g., 0.5, 1, 2, 3, 4 or 5 mg/kg) or 10-1500 mg as a fixed dosage. The dosage depends on the condition of the patient and response to prior treatment, if any, whether the treatment is prophylactic or therapeutic and whether the disorder is acute or chronic, among other factors.

Administration can be parenteral, intravenous, oral, subcutaneous, intra-arterial, intracranial, intrathecal, intraperitoneal, topical, intranasal or intramuscular. Administration into the systemic circulation by intravenous or subcutaneous administration is preferred. Intravenous administration can be, for example, by infusion over a period such as 30-90 min.

The frequency of administration depends on the half-life of the antibody in the circulation, the condition of the patient and the route of administration among other factors. The frequency, can be daily, weekly, monthly, quarterly, or at irregular intervals in response to changes in the patient's condition or progression of the disorder being treated. An exemplary frequency for intravenous administration is between weekly and quarterly over a continuous cause of treatment, although more or less frequent dosing is also possible. For subcutaneous administration, an exemplary dosing frequency is daily to monthly, although more or less frequent dosing is also possible.

The number of dosages administered depends on whether the disorder is acute or chronic and the response of the disorder to the treatment. For acute disorders or acute exacerbations of a chronic disorders between 1 and 10 doses are often sufficient. Sometimes a single bolus dose, optionally in divided form, is sufficient for an acute disorder or acute exacerbation of a chronic disorder. Treatment can be repeated for recurrence of an acute disorder or acute exacerbation. For chronic disorders, an antibody can be administered at regular intervals, e.g., weekly, fortnightly, monthly, quarterly, every six months for at least 1, 5 or 10 years, or the life of the patient.

Pharmaceutical compositions for parenteral administration are preferably sterile and substantially isotonic and manufactured under GMP conditions. Pharmaceutical compositions can be provided in unit dosage form (i.e., the dosage for a single administration). Pharmaceutical compositions can be formulated using one or more physiologically acceptable carriers, diluents, excipients or auxiliaries. The formulation depends on the route of administration chosen. For injection, antibodies can be formulated in aqueous solutions, preferably in physiologically compatible buffers such as Hank's solution, Ringer's solution, or physiological saline or acetate buffer (to reduce discomfort at the site of injection). The solution can contain formulatory agents such as suspending, stabilizing and/or dispersing agents. Alternatively antibodies can be in lyophilized form for constitution with a suitable vehicle, e.g., sterile pyrogen-free water, before use.

Treatment with antibodies of the invention can be combined with other treatments effective against the disorder being treated. For treatment of immune disorders, conventional treatments include mast cell degranulation inhibitors, corticosteroids, nonsteroidal anti-inflammatory drugs, and stronger anti-inflammatory drugs such as azathioprine, cyclophosphamide, leukeran, FK506 and cyclosporine. Biologic anti-inflammatory agents, such as Tysabri® (natalizumab) or Humira® (adalimumab), can also be used. When used in treating cancer, the antibodies of the invention can be combined with chemotherapy, radiation, stem cell treatment, surgery or treatment with other biologics such as Herceptin® (trastuzumab) against the HER2 antigen, Avastin® (bevacizumab) against VEGF, or antibodies to the EGF receptor, such as (Erbitux®, cetuximab), and Vectibix® (panitumumab). Chemotherapy agents include chlorambucil, cyclophosphamide or melphalan, carboplatinum, daunorubicin, doxorubicin, idarubicin, and mitoxantrone, methotrexate, fludarabine, and cytarabine, etoposide or topotecan, vincristine and vinblastine.

V. Other Applications

The anti-CD122 antibodies can be used for detecting CD122 in the context of clinical diagnosis or treatment or in research. For example, the antibodies can be used to detect presence of CD122 on T-cells as an indication a patient is suffering from an immune mediated disorder amenable to treatment. Expression of CD122 on a cancer also provides an indication that the cancer is amenable to treatment with the antibodies of the present invention. The antibodies can also be sold as research reagents for laboratory research in detecting T-cells and their response to various stimuli. In such uses, monoclonal antibodies can be labeled with fluorescent molecules, spin-labeled molecules, enzymes or radioisotopes, and can be provided in the form of kit with all the necessary reagents to perform the assay for CD122. The antibodies can also be used to purify CD122, e.g., by affinity chromatography.

All patent filings, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise if different versions of a publication, website or the like are published at different times, the version most recently published at the effective filing date of the application is meant unless otherwise indicated. Any feature, step, element, embodiment, or aspect of the invention can be used in combination with any other unless specifically indicated otherwise. Although the present invention has been described in some detail by way of illustration and example for purposes of clarity and understanding, it will be apparent that certain changes and modifications may be practiced within the scope of the appended claims.

EXAMPLES

The following examples discuss the production, characterization, and humanization of monoclonal antibodies against human CD122 and also provide exemplary methods by which binding characteristics by which the antibodies described in this application can be determined.

Example 1

Isolation of Mouse Anti-Human CD122 Monoclonal Antibodies

Two forms of immunogens were used to elicit an anti-CD122 response in mice: the isolated human CD122 extracellular region fused to the human IgG1 Fc region (CD122-Fc) and a murine myeloma cell (NS0) transfectant stably expressing full length human CD122 and human CD132 (the intact native human IL-2/15 intermediate affinity receptor) on the cell surface (NS0-βγ). The gene encoding CD122-Fc was created by fusing the human CD122 extracellular region (including its signal peptide) coding sequence 5' to the human IgG1 Fc coding sequence. The CD122-Fc gene was cloned into an expression vector under the control of human CMV early promoter. The expression vector also contains a gpt marker for selection. The CD122-Fc expression vector was then introduced into the mouse myeloma cell line NS0 (European Collection of Animal Cell Cultures, Salisbury, Wiltshire, UK) by electroporation, and transfectants were selected by the use of the gpt marker. Spent media of transfectants was screened by ELISA for secretion of CD122-Fc, and a high producing cell line was expanded into serum-free growth medium using Hybridoma SFM (Invitrogen, Carlsbad, Calif.). CD122-Fc was purified from the spent serum free medium by Protein A Sepharose® affinity chromatography. An NS0-βγ stable transfectant was similarly created by transfecting an expression vector containing both the full length human CD122 and CD132 coding sequences into NS0 cells. Transfectants expressing both gene products on the cell surface were identified by flow cytometry using commercially available anti-human CD122 and CD 132 antibodies.

Generation of mouse hybridoma was performed using standard protocols. Hybridoma culture supernatants were first screened for reactivity to human CD122 by ELISA. Microtiter plates were coated with either CD122-Fc or an irrelevant-Fc fusion protein. Spent media of mouse hybridoma were added to each well of the microtiter plates. After incubation, the plates were washed with PBS, incubated with peroxidase-conjugated goat-anti-mouse kappa polyclonal antibodies, washed again, and developed with peroxidase substrate ABTS. Supernatants showing reactivity to CD122-Fc but not to the irrelevant Fc-fusion protein were designated as specific for CD122 and the hybridomas were expanded. Reactivity to native human CD122 expressed on the cell surface was established by demonstrating reactivity of these supernatants to NS0-βγ and human T-cells activated by PHA and IL-2, but not to untransfected NS0, by flow cytometry.

Mouse hybridomas secreting antibodies that exhibit specific binding to native human CD122 were individually subcloned, isotyped, and expanded in serum-free media using Hybridoma-SFM for purification of monoclonal antibodies. Mouse IgG2a and IgG2b antibodies were purified using Protein A Sepharose® affinity chromatography, and mouse IgG1 was purified using Protein G. Purified mouse anti-human CD122 monoclonal antibodies were initially characterized by confirming binding to human CD122 expressed on the surface of normal (human T cells) and transfected (NS0-βγ) cells by flow cytometry. Two anti-CD122 antibodies, ABC2 (IgG1/kappa) and ABC101 (IgG2b/kappa), were selected based on their preliminary performance in CD122 binding and functional assays. Both ABC2 and ABC101 specifically bind to human and cynomolgus CD122 and lacked significant binding to dog and mouse CD122 (i.e., not detectably different than an irrelevant control antibody).

Example 2

Inhibition of IL-15-Mediated Proliferation

Growth of the human erythroleukemia cell line TF-1 (ATCC, Manassas, Va.) is completely dependent on exogenously supplied cytokines such as GM-CSF or IL-3 (Kitamura, T., et al., Blood 73:375-380 (1989)). TF-1 expresses the common γ chain (CD132) and the IL-15 receptor α chain (Mortier et al., J. Biol. Chem., 281:1612-1619 (2006)), but not the IL-2/IL-15 receptor β chain (CD122), so IL-15 cannot support the growth of TF-1. Expression of the CD122 gene in TF-1 allows for the expression of the intermediate and high affinity IL-15 receptors, and permits human IL-15 to support the growth of the transfectant. TF-1β was generated by stable transfection of TF-1 with a mammalian expression vector carrying a gene coding for human CD122 and a puromycin resistance gene. TF-1β grows in the presence of human IL-15 as well as when supplied with a soluble complex of human IL-15 bound to a portion of the extracellular region of the human IL-15Rα (scIL-15/IL-15Rα), which substitutes for the cell bound IL-15/IL-15Rα complex and represents the trans-presentation of IL-15 (Mortier et al., J. Biol. Chem., 281:1612-1619 (2006)). The IL-15/IL-15Rα fragment complex (scIL-15/IL-15Rα) was constructed by connecting the human IL-15Rα sushi domain to human IL-15 with a peptide linker and adding six histidine residues to the carboxyl terminus essentially according to the report by Mortier et al. (J. Biol. Chem., 281:1612-1619 (2006)), and provided a model of IL-15 trans-presentation.

The ability of anti-CD122 monoclonal antibodies to inhibit cell proliferation mediated by trans-presented IL-15 was examined using TF-1β cells and scIL-15/IL-15Rα. In typical experiments, $6 \times 10^4$ TF-1β cells were incubated with varying amounts of purified mouse anti-CD122 monoclonal antibodies for 10 min at 37° C. Ten ng/ml of scIL-15/IL-15Rα was then added, and the cells were incubated for an additional 72 hr at 37° C., after which the tetrazolium salt WST-8 (Dojindo Molecular Technologies, Rockville, Md.) was added. Following 3 hr incubation with WST-8 at 37° C., cell proliferation was inferred by measuring absorbance at 450 nm, which is indicative of dehydrogenase activity and directly proportional to the number of living cells. The proliferation level in the presence of test antibodies was compared to that in the absence of antibody to determine inhibitory activity. As shown in FIG. 1, ABC2 and ABC101 substantially suppressed the growth of TF-1β cells mediated by the trans-presentation of IL-15 (i.e., in the presence of scIL-15/IL-15Rα), exhibiting approximately 50% inhibition at a concentration of 1.0 μg/ml for ABC2 and 0.5 μg/ml for ABC101.

The ability of anti-CD122 monoclonal antibodies to inhibit cell proliferation mediated by cis-presented IL-15 was also examined using TF-1β. In typical experiments, $6 \times 10^4$ TF-1β cells were incubated with varying amounts of purified anti-CD122 antibodies for 10 min at 37° C. IL-15 was then added at 10 ng/ml, and the cells were incubated for an additional 72 hr at 37° C. The level of cell proliferation was measured using the tetrazolium salt WST-8 as described above and compared to that without test antibodies. ABC2 and ABC101 substantially inhibited TF-1β proliferation by approximately 75% and 40%, respectively, at a concentration of 370 ng/ml.

Example 3

Inhibition of IL-2-Mediated Proliferation Via the Intermediate and High Affinity IL-2 Receptors ABC2 and ABC101 were analyzed for the ability to inhibit IL-2-mediated cell proliferation via the intermediate affinity IL-2 receptor using TF-1β cells. In typical experiments, $6 \times 10^4$ TF-1β cells were incubated with varying amounts of purified anti-CD122 antibodies for 10 min at 37° C. IL-2 was then added at 200 ng/ml, and the cells were incubated for an additional 72 hr at 37° C. The level of cell proliferation was measured using the tetrazolium salt WST-8 as described above and compared to that without test antibodies. Both of ABC2 and ABC101 substantially neutralized IL-2 activity by exhibiting over 50% inhibition of IL-2-mediated growth of TF-1β cells at a concentration of 80 ng/ml.

Figure 2:
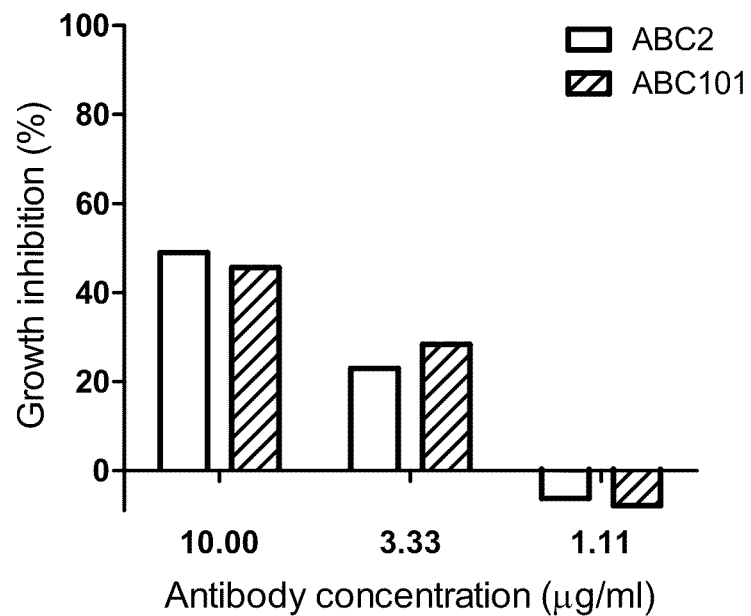
FIG. 2. Effects of ABC2 and ABC101 on IL-2-mediated cell proliferation via the high affinity IL-2 receptor.

ABC2 and ABC101 were further examined for the ability to inhibit IL-2-mediated cell proliferation via the high affinity IL-2 receptor. TF-1αβ was generated by stable transfection of TF-1 with a mammalian expression vector encoding both human CD25 and CD122 and thus expresses the high affinity IL-2 receptor. In typical experiments, 6×10$^4$ TF-1αβ cells were incubated with varying amounts of purified anti-CD122 antibodies for 10 min at 37° C. IL-2 was then added at 10 ng/ml, and the cells were incubated for an additional 72 hr at 37° C. The level of cell proliferation was measured using the tetrazolium salt WST-8 as described above and compared to that without test antibodies. As shown in FIG. 2, ABC2 and ABC101 substantially inhibited the growth of TF-1αβ cells in the presence of IL-2. At 10 μg/ml, ABC2 and ABC101 inhibited TF-1αβ proliferation by 49% and 46%, respectively.

Example 4

Sequencing of Heavy and Light Chain Variable Regions

Total RNA was extracted from approximately 10$^7$ hybridoma cells using TRIzol reagent (Invitrogen) and oligo dT-primed cDNA for 5'-RACE was synthesized using the GeneRacer Kit (Invitrogen, Carlsbad, Calif.) or SMARTer RACE cDNA Amplification Kit (Clontech, Mountain View, Calif.) following the supplier's protocol. The variable region cDNAs for heavy and light chains were amplified by polymerase chain reaction (PCR) using 3' primers that anneal respectively to the mouse gamma-1 and kappa chain constant regions, and the 5'-RACE primer provided in the GeneRacer Kit or SMARTer RACE cDNA Amplification Kit. For PCR amplification of heavy chain variable regions (VH), the 3' primer has the sequence 5'-GCCAGTGGATAGACAGATGG-3' (for gamma-1) (SEQ ID NO:17), 5'-GCCAGTGGATAGAC-CGATGG-3' (for gamma-2a) (SEQ ID NO:18) or 5'-GC-CAGTGGATAGACTGATGG-3' (for gamma-2b) (SEQ ID NO:19). For light chain variable region (VL), the 3' primer has the sequence 5'-GATGGATACAGTTGGTGCAGC-3' (SEQ ID NO:20). The amplified VH and VL cDNAs were subcloned into the pCR4Blunt-TOPO vector (Invitrogen) for sequence determination. Several heavy and light chain clones were sequenced and unique sequences homologous to typical mouse heavy and light chain variable regions were identified.

The consensus cDNA and deduced amino acid sequences of ABC2 VH are shown in FIG. 3. The signal peptide sequence (MKLWLNWVFLLTLLHGIQC) (SEQ ID NO:21) is in italic. The N-terminal amino acid residue of the mature polypeptide (E) is double-underlined. CDR sequences according to the definition of Kabat et al. (Sequences of Proteins of Immunological Interests, Fifth edition, NIH Publication No. 91-3242, U.S. Department of Health and Human Services, 1991) are underlined. The CDR1, CDR2 and CDR3 sequences of ABC VH are DFYME (SEQ ID NO:22), ASRNKANDYTTEYSASVKG (SEQ ID NO:23) and SYYRYDGMDY (SEQ ID NO:24), respectively. The amino acid sequence of the mature ABC2 VH is EVKLVESGGGLVQPGGSLRLSCATSG-FTFSDFYMEWVRQPPGKRLEWIAASRNKANDY TTEYSASVKGRFIVSRDTSQSILYLQM-NALRAEDTAIYYCARSYYRYDGMDYWGQGTS VTVSS (SEQ ID NO:25).

The consensus cDNA and deduced amino acid sequences of ABC2 VL are shown in FIG. 4. The signal peptide sequence (MDFQVQIFSFLLISASVIVSRG) (SEQ ID NO:26) is in italic. The N-terminal amino acid residue of the mature polypeptide (Q) is double-underlined. CDR sequences according to the definition of Kabat et al. (supra) are underlined. The CDR1, CDR2 and CDR3 sequences of ABC2 VL are SAISSVSYMY (SEQ ID NO:27), DTSNLVS (SEQ ID NO:28) and QQWNTYPYT (SEQ ID NO:29), respectively. The amino acid sequence of the mature ABC2 VL is QVV-LTQSPVIMSASPGEKVTMTCSAISSVSY-MYWYQQKPGSSPRLLIYDTSNLVSGVPV RFSGSGS-GTSYSLTISRMEAEDAATYYCQQWNTYPYTFGG GTKLEIK (SEQ ID NO:30).

The consensus cDNA and deduced amino acid sequences of ABC101 VH are shown in FIG. 5. The signal peptide sequence (MRVLILVYLLTVLPGILS) (SEQ ID NO:31) is in italic. The N-terminal amino acid residue of the mature polypeptide (D) is double-underlined. CDR sequences according to the definition of Kabat et al. (supra) are underlined. The CDR1, CDR2 and CDR3 sequences of ABC101 VH are NDNHWWN (SEQ ID NO:32), YIDSSGSSDN-NPSLKS (SEQ ID NO:33) and GGGRDYYGMDY (SEQ ID NO:34), respectively. The amino acid sequence of the mature ABC101 VH is DVQLQESGPGLVKPSQTVSLTCTVT-GYSITNDNHWWNWIRQVSGSKLEWMGYIDSSGS SDNNPSLKSQISITRDTSKNQLFLQLNS-VTIEDIGTYYCARGGGRDYYGMDYWGQGTSV TVSS (SEQ ID NO:35).

The consensus cDNA and deduced amino acid sequences of ABC101 VL are shown in FIG. 6. The signal peptide sequence (METDTLLLWVLLLWVPGSTG) (SEQ ID NO:36) is in italic. The N-terminal amino acid residue of the mature polypeptide (D) is double-underlined. CDR sequences according to the definition of Kabat et al. (supra) are underlined. The CDR1, CDR2 and CDR3 sequences of ABC101 VL are RASQSVSTSSYSYVH (SEQ ID NO:37), YASNLES (SEQ ID NO:38) and QHSWDIPFT (SEQ ID NO:39), respectively. The amino acid sequence of the mature ABC101 VL is DIVLTQSPASLAVSLGQRATISCRASQS-VSTSSYSYVHWYQQKPGQPPKLLIKYASNLES GVPARFSGSGSGTDFTLNIHPVEEED-TATYYCQHSWDIPFTFGGGTKLEIK (SEQ ID NO:40).

Example 5

Humanization of ABC2 VH and VL

Designing and construction of humanized VH and VL genes was carried as described previously (Tsurushita, N., et al., Methods 36:69-83 (2005)). Human VH sequences homologous to the mouse ABC2 VH frameworks were searched for within the GenBank database, and the VH sequence encoded by the human DA430129 cDNA (DA430129 VH) (GenBank accession number; Kimura, K., et al., Genome Res. 16:55-65 (2006)) was chosen as an acceptor for humanization. Alignment of the amino acid sequences of the mature ABC2 VH, humanized ABC2 VH (HuABC2 VH), and human acceptor DA430129 VH regions is shown in FIG. 7. Numbers above the sequences indicate the locations according to Kabat et al. (supra). CDR sequences defined by Kabat et al. (supra) are underlined in the ABC2 VH amino acid sequence. For designing the HuABC2 VH amino acid sequence, the CDR sequences of mouse ABC2 VH were first transferred to the corresponding positions of DA430129 VH. Next, at framework positions where the three-dimensional model of the mouse ABC2 variable regions suggested significant contact with the CDRs, amino acid residues of mouse ABC2 VH were substituted for the corresponding human residues. These substitutions, underlined in the HuABC2 amino acid sequence, were performed at positions 28, 48, 49, 68 and 93 (FIG. 7). In addition, human framework amino acid residues in DA430129 VH that were found to be atypical in the corresponding V region subgroup were substituted with typical residues to reduce potential immunogenicity. This type of substitution, double-underlined in the HuABC2 VH amino acid sequence, was performed at position 42 (FIG. 7). A gene encoding HuABC2 VH was designed as an exon including a signal peptide, a splice donor signal, and appropriate restriction enzyme sites for subsequent cloning into a mammalian expression vector. The signal peptide sequence of the HuABC2 VH gene was derived from the mouse ABC2 VH gene. The splice donor signal of the HuABC2 VH exon was derived from the human germline JH1 segment. The nucleotide and deduced amino acid sequences of the designed HuABC2 VH gene flanked by SpeI and HindIII sites are shown in FIG. 8. The signal peptide sequence is in italic. The N-terminal amino acid residue of the mature polypeptide is double-underlined. CDR sequences according to the definition of Kabat et al. (supra) are underlined. The amino acid sequence of the mature HuABC2 VH is EVQLVESGGGLVQPGGSLRLSCAASG-FTFSDFYMEWVRQAPGKGLEWIAASRNKANDY TTEYSASVKGRFIVS-RDDSKNSLYLQMNSLKTEDTAVYY-CARSYYRYDGMDYWGQGT TVTVSS. (SEQ ID NO:41).

Human Vk sequences homologous to the mouse ABC2 VL frameworks were searched for within the GenBank database, and the Vk sequence encoded by the human M29469 cDNA (M29469 VL) (GenBank accession number; Spatz et al., J. Immunol. 144:2821-2828 (1990)) was chosen as an acceptor for humanization. Alignment of the amino acid sequences of the mature ABC2 VL, humanized ABC2 VL (HuABC2 VH), and human acceptor M29469 VL regions is shown in FIG. 9. Numbers above the sequences indicate the locations according to Kabat et al. (supra). CDR sequences defined by Kabat et al. (supra) are underlined in the ABC2 VL amino acid sequence. For designing the HuABC2 VL amino acid sequence, the CDR sequences of mouse ABC2 VL were first transferred to the corresponding positions of M29469 VL. Next, at the single framework position where the three-dimensional model of the mouse ABC2 variable regions suggested significant CDR contact, the amino acid of mouse ABC2 VL at position 71, underlined in HuABC2 VL, was substituted for the corresponding human residue (FIG. 9). A gene encoding HuABC2 VL was designed as an exon including the signal peptide sequence of the mouse ABC2 VL gene and the splice donor signal derived from the mouse germline Jk1 segment. The nucleotide and deduced amino acid sequences of the designed HuABC2 VL gene flanked by NheI and EcoRI sites are shown in FIG. 10. The signal peptide sequence is in italic. The N-terminal amino acid residue of the mature polypeptide is double-underlined. CDR sequences according to the definition of Kabat et al. (1991) are underlined. The amino acid sequence of the mature HuABC2 VL is EIVLTQSPATLSLSPGERATLSCSAISS-VSYMYWYQQKPGQAPRLLIYDTSNLVSGVPARF SGSGSGTDYTLTISSLEPEDFAVYYC-QQWNTYPYTFGGGTKVEIK (SEQ ID NO:42).

Example 6

Humanization of ABC101 VH and VL

Human VH sequences homologous to the mouse ABC101 VH frameworks were searched for within the GenBank database, and the VH sequence encoded by the human DA936142 cDNA (DA936142 VH) (GenBank accession number; Kimura, K., et al., Genome Res. 16:55-65 (2006)) was chosen as an acceptor for humanization. Alignment of the amino acid sequences of the mature ABC101 VH, humanized ABC101 VH (HuABC101 VH), and human acceptor DA936142 VH regions is shown in FIG. 11. Numbers above the sequences indicate the locations according to Kabat et al. (supra). CDR sequences defined by Kabat et al. (supra) are underlined in the ABC101 VH amino acid sequence. For designing the HuABC101 VH amino acid sequence, the CDR sequences of mouse ABC101 VH were first transferred to the corresponding positions of DA936142 VH. Next, mouse amino acids at positions at 27, 30, 48, 66, 67 and 71, where the three-dimensional model of the mouse ABC101 variable regions suggested significant contact with the CDRs, were substituted for the corresponding human framework residues. The amino acid residues at these positions are underlined in the HuABC101 VH sequence (FIG. 11). A gene encoding HuABC101 VH was designed as an exon including the signal peptide sequence of the mouse ABC101 VH gene and the splice donor signal derived from the human germline JH6 segment. The nucleotide and deduced amino acid sequences of the designed HuABC101 VH gene flanked by SpeI and HindIII sites are shown in FIG. 12. The signal peptide sequence is in italic. The N-terminal amino acid residue of the mature polypeptide is double-underlined. CDR sequences according to the definition of Kabat et al. (1991) are underlined. The amino acid sequence of the mature HuABC101 VH is QVQLQESGPGLVKPSQTLSLTCTVS-GYSITNDNHWWNWIRQHPGKGLEWMGYIDSSGS SDNNPSLKSQITISRDTSKNQLSLKLSS-VTAADTAVYYCARGGGRDYYGMDYWGQGTT VTVSS (SEQ ID NO:43).

For humanization of mouse ABC101 VL, the Vk sequence encoded by the human Z46622 cDNA (Z46622 VL) (GenBank accession number; Giachino et al., J. Exp. Med. 181: 1245-1250 (1995)) was chosen as an acceptor. Alignment of the amino acid sequences of the mature ABC101 VL, humanized ABC101 VL (HuABC101 VL), and human acceptor Z46622 VL regions is shown in FIG. 13. Numbers above the sequences indicate the locations according to Kabat et al. (supra). CDR sequences defined by Kabat et al. (supra) are underlined in the ABC101 VL amino acid sequence. For designing the HuABC101 VL amino acid sequence, the CDR sequences of mouse ABC101 VL were first transferred to the corresponding positions of Z46622 VL. Next, the mouse amino acid at positions 49, where the three-dimensional model of the mouse ABC101 variable regions suggested significant CDR contact, was substituted for the corresponding human framework residue. The amino acid residue at this position is underlined in the HuABC101 VL sequence (FIG. 13). A gene encoding HuABC101 VL was designed as an exon including the signal peptide sequence of the mouse ABC101 VL gene and splice donor signal derived from the mouse germline Jk2 segment. The nucleotide and deduced amino acid sequences of the designed HuABC101 VL gene flanked by NheI and EcoRI sites are shown in FIG. 14. The signal peptide sequence is in italic. The N-terminal amino acid residue of the mature polypeptide is double-underlined. CDR sequences according to the definition of Kabat et al. (1991) are underlined. The amino acid sequence of the mature HuABC101 VL is DIVMTQSPDSLGVSLGERATIN-CRASQSVSTSSYSYVHWYQQKPGQPPKL-LIKYASNLES GVPDRFSGSGSGTDFTLTISSLQAED-VAVYYCQHSWDIPFTFGQGTKLEIK (SEQ ID NO:44).

Example 7

Expression of HuABC2 and HuABC101 IgG1/κ Antibodies

Figure 15:
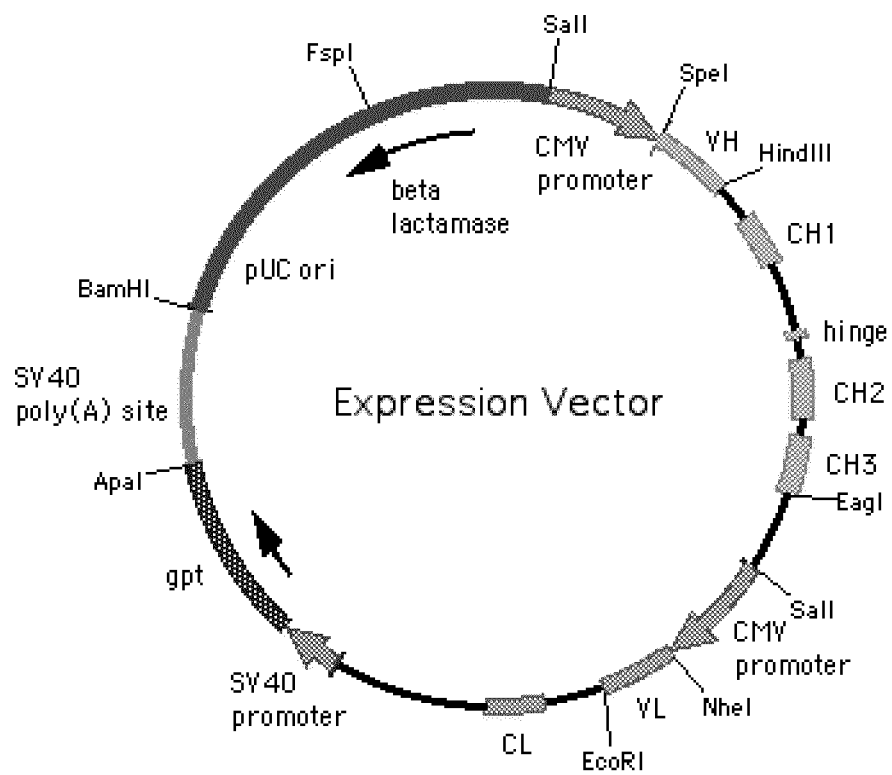
FIG. 15. The schematic structure of the pHuABC2 and pHuABC101 expression vectors.

The HuABC2 VH gene digested with SpeI and HindIII and the HuABC2 VL gene digested with NheI and EcoRI were inserted into the corresponding sites of a mammalian expression vector to generate pHuABC2. The HuABC101 VH gene digested with SpeI and HindIII and the HuABC101 VL gene digested with NheI and EcoRI were inserted into the corresponding sites of a mammalian expression vector to generate pHuABC101. The structure of pHuABC2 and pHuABC101 (collectively, Expression Vector) is shown in FIG. 15. Proceeding clockwise from the SalI site at the top, the Expression Vector contains the heavy chain transcription unit starting with the human cytomegalovirus (CMV) major immediate early promoter and enhancer (CMV promoter) to initiate transcription of the antibody heavy chain gene. The CMV promoter is followed by the VH exon, a genomic sequence containing the human gamma-1 heavy chain constant region including the CH1, hinge, CH2 and CH3 exons with the intervening introns, and a polyadenylation site of the gamma-1 gene for mRNA processing following CH3. After the heavy chain gene sequence, the light chain transcription unit begins with the CMV promoter, followed by the VL exon and a genomic sequence containing the human kappa chain constant region exon (CL) with part of the intron preceding it, and a poly A signal of the kappa gene. The light chain gene is then followed by the SV40 early promoter (SV40 promoter), the *E. coli* xanthine guanine phosphoribosyl transferase gene (gpt), and a segment containing the SV40 polyadenylation site (SV40 poly(A) site). Finally, the Expression Vector contains a part of the plasmid pUC19, comprising the bacterial origin of replication (pUC ori) and beta-lactamase gene (beta lactamase).

To obtain cell lines stably producing HuABC2 and HuABC101 IgG1/κ antibodies (HuABC2 and HuABC101, respectively), the expression vectors pHuABC2 and pHuABC101, respectively, were introduced into the chromosome of the mouse myeloma cell line NS0. Stable transfection into NS0 was carried out by electroporation as described in Bebbington et al. (Bio/Technology 10: 169-175, 1992). Before transfection, expression vector was linearized using FspI. Approximately $10^7$ cells were transfected with 10 μg of linearized plasmid, suspended in DME medium containing 10% FBS, and plated into several 96-well plates. After 24 hr, selection media (DME medium containing 10% FBS, HT media supplement (Sigma, St. Louis, Mo.), 0.25 mg/ml xanthine and 1 μg/ml mycophenolic acid) was applied. Approximately 10 days after the initiation of selection, culture supernatants from transfectants surviving selection were assayed for antibody production.

Expression of HuABC2 and HuABC101 was measured by sandwich ELISA following standard procedures, typically using goat anti-human IgG Fc polyclonal antibody for capture and HRP-conjugated goat anti-human kappa chain polyclonal antibody for detection of bound humanized antibodies. Varying quantities of an appropriate human IgG1/κ antibody was used to construct a standard curve to allow for quantification. NS0 stable transfectants producing a high level of each of HuABC2 and HuABC101 were adapted to and expanded in serum-free media using Hybridoma SFM (Invitrogen). HuABC2 and HuABC101 were purified from culture supernatant by Protein A affinity chromatography.

Example 8

Characterization of Humanized Anti-CD122 Antibodies

Figure 16:
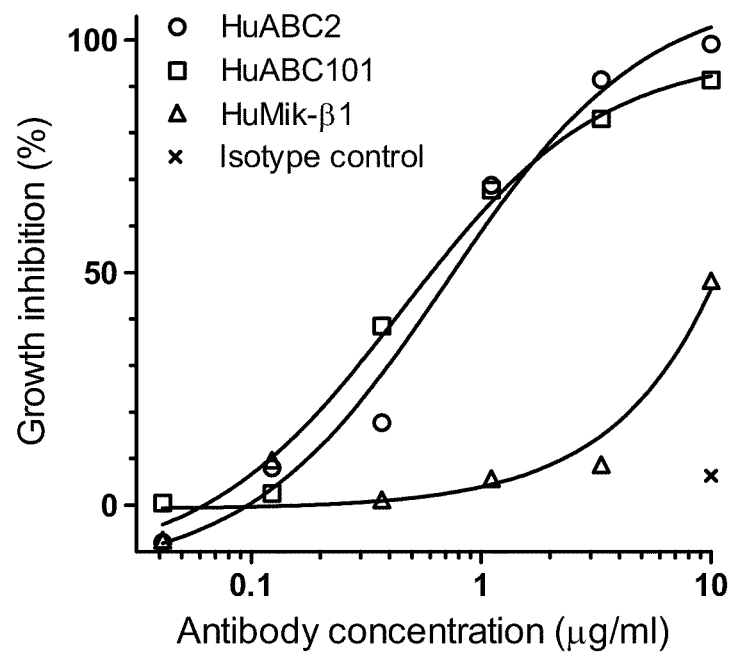
FIG. 16. Effects of HuABC2 and HuABC101 on trans-presentation of IL-15.

Purified HuABC2 and HuABC 101 were characterized for the ability to inhibit the proliferation of TF-1β mediated by a soluble IL-15/IL-15Rα complex (trans-presentation of IL-15 using scIL-15/IL-15Rα as described above) (FIG. 16). Both HuABC2 and HuABC101 substantially inhibited the growth of TF-1β whereas the humanized version of the mouse anti-CD122 monoclonal antibody Mik-β1 (HuMik-β1; Hakimi et al., supra) exhibited only slight inhibition at the highest concentration (10 μg/ml) tested. The antibody concentration required for 50% inhibition of proliferation mediated by trans-presentation of IL-15 to TF-1β cells was 0.7 μg/ml for HuABC2, 0.5 μg/ml for HuABC101, and approximately 10 μg/ml for HuMik-β1.

Figure 17:
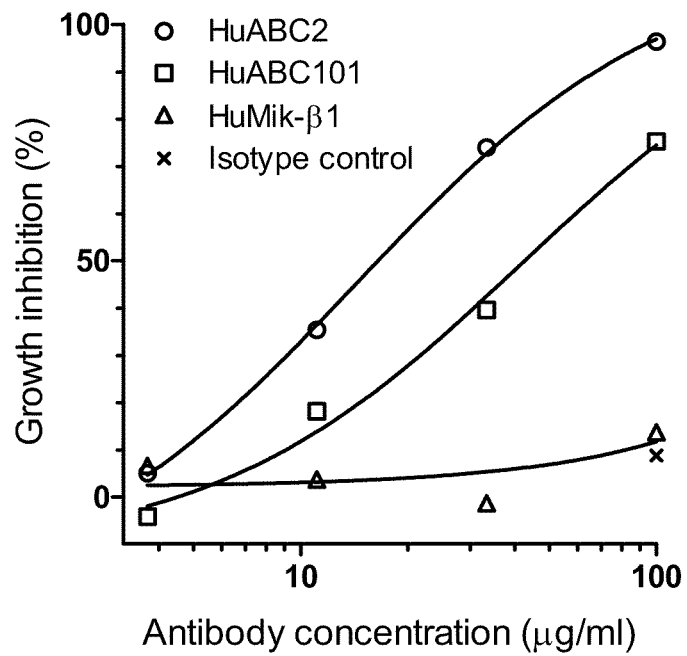
FIG. 17. Effects of HuABC2 and HuABC101 on IL-2-mediated cell proliferation via the high affinity IL-2 receptor.

Purified HuABC2 and HuABC101 were further characterized for the ability to inhibit the proliferation of TF-1αβ, which expresses the high affinity IL-2 receptor, in the presence of IL-2 as described above (FIG. 17). Both HuABC2 and HuABC101 substantially inhibited the growth of TF-1αβ whereas HuMik-β1 exhibited no activity and showed a level of inhibition equivalent to that seen with the isotype control at the highest antibody concentration (100 μg/ml) tested. The antibody concentration required for 50% inhibition IL-2-mediated TF-1αβ proliferation was 14 μg/ml for HuABC2 and 42 μg/ml for HuABC101.

Example 9

In Vivo Analysis of Humanized Anti-CD122 Antibodies on the Development of Xenographic Graft Versus Host Disease The effect of HuABC2 treatment on the development of graft versus host disease was established in a xenographic model utilizing immunodeficient mice (van Rijn, R. S., et al., Blood 102:2522-2531 (2003)) receiving human immuocompetant cells. Xenogeneic graft versus host disease (XGVHD) was induced in NOD/Shi-scid, IL-2Rγ$^{null}$ (NOG) mice by the transfer of human peripheral blood mononuclear cells (PBMC) as described (Ito, R., et al., Transplantation 87:1654-1658 (2009)). In particular, NOG mice 8-10 weeks of age were irradiated with 2.5 Gy one day before PBMC transfer by intravenous injection with $1\times10^7$ human PBMC. The mice were monitored every day and weighed twice per week to track disease development. Mice that develop XGVHD begin to lose weight 2-3 days post PBMC transfer and exhibit hunched posture, ruffled fur, reduced mobility, tachypnea, and anemia; death commonly occurs at 10 to 14 days post transfer of $1\times10^7$ human PBMC into irradiated recipients. To show that treatment of the mice with humanized anti-CD122 antibodies alters the course of XGVHD, NOG mice were treated with an intraperitoneal injection of 10 mg/kg (antibody/body weight) of either a control human IgG1 antibody or a HuABC2 one day prior to PBMC transfer, the day of PBMC transfer, and on days 3, 7, and 10 post PBMC transfer. Mice were weighted prior to each antibody administration and monitored for signs of XGVHD as described above until death or sacrifice as per IACUC guidelines. Human cell engraftment, an indication of disease progression, was monitored 10 days post PBMC transfer by determining the percentage of human CD45+ cells present in the blood of each mouse by flow cytometry. Ten days post PBMC transfer, mice treated with a control antibody had lost an average of 20±2.8% of their body weight, whereas mice treated with HuABC2 only lost an average of 10±2.3% of their body weight. Mice treated with a control antibody had an average of 89.2±4.2% human CD45+ cells in their blood ten days post PBMC transfer, while mice treated with HuABC2 had 64.9±11.6% human CD45+ cells in their blood ten days post PBMC transfer. All six mice treated with a control antibody had died by day 10 post PBMC transfer, while only two out of six mice treated with HuABC2 had died by that day. Thus by three separate parameters, percentage of body weight loss, percentage of human cell engraftment, and mortality, mice treated with HuABC2 exhibited a less severe form of GVHD than did mice treated with a control antibody.

Example 10

Analysis of Humanized Anti-CD122 Antibodies in a Model of Psoriasis

Phenotypic features of psoriasis (e.g., epidermal thickening, extensive rete peg formation and presence of inflammatory cells) are maintained when human psoriatic skin is transplanted onto severe combined immunodeficienct (SCID) mice (Nickoloff et al., Am. J. Pathol. 146:580-588 (1995)). This model has been used for the study of the efficacy of drug candidates on psoriasis (Zegler et al., Lab Invest. 81:1253-1261 (2001); Villadsen et al., J. Clin. Invest. 112:1571-1580 (2003); Bhagavathula et al., Am. J. Pathol. 166:1009-1016 (2005)), and a positive effect in this model usually corresponds to efficacy in humans. This example describes an in vivo study demonstrating the efficacy of HuABC2 in the human psoriatic skin-SCID mouse transplant model.

In a typical experiment, human psoriatic plaque skin is transplanted onto several SCID mice. After allowing the tissue to heal, mice are treated by an intraperitoneal injection of either HuABC2 or control antibody at 10 mg/kg per animal every 3 days for 21 days. At the end of the treatment period, animals are sacrificed. The transplanted human skin with a small amount of surrounding mouse skin is removed and fixed in 10% buffered formalin. After staining with hexatoxylin and eosin, tissue sections are examined histologically by light microscopy. The epidermal area of each tissue section is captured in equal segments and epidermal thickness is determined in a blinded manner. A small piece of psoriatic donor skin fixed in 10% buffered formalin before transplantation is used for the zero-time assessment of epidermal thickness. The epidermal thickness is compared between HuABC2 and control groups to evaluate the therapeutic efficacy of HuABC2 on psoriasis. The effects of HuABC2 are further evaluated by (1) analyzing skin grafts histologically for characteristic features of psoriasis including epidermal hyperplasia and rete peg formation and (2) staining tissue sections with an antibody to human CD3 or other cell surface markers to identify infiltrating cells.

Example 11

Epitope Mapping

The extracellular region of CD122 is composed of two fibronectin type III domains termed D1 and D2 (Wang, X. et al. Science 310:1159-1163 (2005)). To localize the epitopes in the CD122 molecule recognized by ABC2 and ABC101, all mouse anti-human CD122 antibodies obtained at JN Biosciences, the pattern of their binding to various murine/human chimeric molecules of CD122 and isolated domains of the human CD122 molecule expressed on the surface of HEK293 cells was determined by flow cytometry. In addition, the mouse anti-CD122 monoclonal antibody Mik-β1 (Tsudo et al., Proc. Natl. Acad. Sci. USA 86:1982-1986 (1989)) was included in the analysis as was a further mouse anti-CD122 antibody generated by the present applicant, ABC116, which has weak ability to inhibit CD122 interactions with IL-2 and IL-15 compared with ABC2 and ABC101.

The six different recombinant CD122 constructs depicted in FIG. 18 were used for the analysis. HuD1/HuD2 contains the human CD122 D1 (Ala at position 1 to Phe at position 101 of mature protein; SEQ ID NO:49) and D2 (Glu at position 102 to Thr at position 214 of mature protein; SEQ ID NO:50) domains. Ala at position 1 corresponds to the twenty-seventh amino acid counted from the N-terminal Met in the human CD122 coding region. MoD1/MoD2 contains the mouse CD122 D1 (Ala at position 1 to Phe at position 102 of mature protein; SEQ ID NO:51) and D2 (Asp at position 103 to Ile at position 215 of mature protein; SEQ ID NO:52) domains. HuD1/MoD2 contains the human D1 and mouse D2 domains (SEQ ID NO:49 and SEQ ID NO:52, respectively). MoD1/HuD2 contains the mouse D1 and human D2 domains (SEQ ID NO:51 and SEQ ID NO:50, respectively). HuD1 contains the isolated human D1 domain (SEQ ID NO:49), and HuD2 contains the isolated human D2 domain (SEQ ID NO:50). All of the six constructs were fused at the carboxyl terminus to the FLAG peptide followed by the GPI anchorage signal derived from the human CD55 gene (SEQ ID NO:53). These constructs were cloned in an appropriate plasmid vector for expression on the surface of HEK293 cells.

Binding of ABC2, ABC101, ABC116 and Mik-β1 (5 μg/ml) to transfectants expressing each of the six CD122 constructs was examined by flow cytometry using standard procedures. Expression of these constructs on the cell surface was confirmed using a rat anti-FLAG peptide antibody L5 (BioLegend, San Diego, Calif.). HEK293 cells transiently expressing each one of the six CD122 constructs were first incubated with one of the test antibodies. Bound mouse antibodies were then detected with PE-labeled goat anti-mouse IgG antibody. The binding pattern of ABC2, ABC101, ABC116 and Mik-β1 to these CD122 constructs is summarized in FIG. 18. The symbol "+" in the figure indicates that the MCF (geometrical mean channel fluorescence) value with a test antibody was at least 50% of the MCF value with L5 for each transfectant. The symbol "−" indicates that the MCF value with a test antibody was less than 10% of the value with L5 (i.e., an indication of lack of specific binding within the margin of accuracy with which such binding can be measured). The D1 domain of human CD122 alone was sufficient for binding of ABC2 and Mik-β1. Likewise, the D2 domain of human CD122 alone was sufficient for binding of ABC116. For binding of ABC101, the presence of the both human D1 domain and either the human or mouse D2 domain was necessary, indicating the epitope of ABC101 requires amino acid residues from both the D1 and D2 domains.

More specifically to localize the epitope recognized in the CD122 molecule by each of ABC2, ABC101 and Mik-131, single amino acid substitution mutants were generated in the HuD1/HuD2 construct (SEQ ID NO:54) by site-directed mutagenesis using standard procedures. Each mutant HuD1/HuD2 construct was then fused at the carboxyl terminus to the FLAG peptide followed by the GPI anchorage signal derived from the human CD55 gene (SEQ ID NO:53) for detection and expression, respectively, on the surface of HEK293 cells. The HuD1/HuD2 mutants used in the analysis are listed in FIG. 19. The letter on the left, number in the middle, and the letter on the right in the name of each mutant denote an amino acid in the wild-type CD122, location in CD122, and an amino acid in the mutant, respectively. The symbols "+", "+/−" and "−" in the figure indicate that the MCF value with a test antibody was at least 50%, between 10% and 20%, and no more than 10% of the MCF value obtained with a rat anti-FLAG peptide antibody L5 for each transfectant, respectively, when a test antibody was used at 100 ng/ml.

Amino acid residues at positions 39 and 41 of human CD122 were identified to be important for binding of Mik-β1 to cell surface expressed CD122 Dionyssopoulou et al., J. Immunol. Methods, 241:83-95 (2000), using a solid phase peptide scanning strategy, had previously reported that Mik-β1 recognized a discontinuous epitope formed by amino acids located in two areas in the D2 domain; one from Leu at 106 to Pro at 148 and another from Glu at 170 to Ala at 202. Our results examining cell surface expressed CD122 suggest that the D2 domain is not critical for binding of Mik-β1 to CD122 and that the determinant recognized by Mik-β1 resides solely in the D1 domain.

Amino acid residues at positions 42, 43 and 65 in the D1 domain were found to be important for binding of ABC2 to human CD122 (FIG. 19). For binding of ABC101, amino acid residues at positions 65 and 70 in the D1 domain and a residue at position 133 in the D2 domain were important (FIG. 19). Thus, a unique set of amino acid residues is involved in the binding of each of ABC2 and ABC101 to human CD122.

The binding of HuABC2 and HuABC101 to the eighteen single-amino-acid-substitution mutants of human CD122 shown in FIG. 19 was also examined by FACS following the procedure described above, except that bound humanized antibodies were detected with PE-labeled goat anti-human IgG antibody. HuABC2 and ABC2 showed the same binding pattern with these eighteen CD122 mutants. Likewise, the binding pattern of HuABC101 with these CD122 mutants was same as that of ABC101. Twenty nine other single-amino-acid-substitution mutants in the D1 and D2 domains of human CD122 did not substantially reduce the binding of HuABC2 or HuABC101 to CD122.

The importance of amino acid residues at positions 42, 43, 65 and 133 in the functional ability of human CD122 to transmit IL-2 and IL-15 mediated signaling was assessed in the following manner. The expression vector for full length human CD122 (SEQ ID NO:73), which had been used for generation of TF-1β cells in Example 2, was subjected to site-directed mutagenesis at positions 42, 43, 65 and 133. The resulting mutant CD122 genes designated as F-R42A (SEQ ID NO:74), F-R43A (SEQ ID NO:75), F-G65T (SEQ ID NO:76) and F-H133A (SEQ ID NO:77) (FIG. 20) carry single amino acid substitutions from Arg to Ala at position 42, Arg to Ala at position 43, Gly to Thr at position 65, and H is to Ala at position 133, respectively. TF-1 stable transfectants were generated with each of these four mutant CD122 genes as described in Example 2.

When RPMI-1640 medium containing 10% FCS was used as basal media, TF-1 grew healthily in the presence of 2 ng/ml GM-CSF, but did not grow at all in the absence of GM-CSF. TF-1 also did not grow in the presence of 200 ng/ml IL-2 or 10 ng/ml of IL-15/IL-15Rα complex (scIL-15/IL-15Rα; a soluble complex of human IL-15 bound to a portion of the extracellular domain of the human IL-15Rα). TF-1β, which expresses intermediate affinity IL-2/IL-15 receptors, grew healthily in the presence of GM-CSF, IL-2, or IL-15/IL-15Rα complex. TF-1 cells expressing the F-R42A, F-G65T or F-H133A mutant of human CD122 lost the ability to grow in the presence of IL-2 or IL-15/IL-15Rα complex, yet they were still capable of growing in the presence of GM-CSF. TF-1 cells expressing the F-R43A mutant maintained the ability to grow in the presence of IL-2, IL-15/IL15Rα complex, or GM-CSF.

What is claimed is:

1. An isolated monoclonal antibody that specifically binds to CD122 (SEQ ID NO:73) comprising three light chain CDRs designated SEQ ID NOS. 27-29 respectively and three heavy chain CDRs designated SEQ ID NOS. 22-24 respectively.

2. The monoclonal antibody of claim 1 that is chimeric, humanized, or veneered.

3. The monoclonal antibody of claim 1 that has human IgG1 kappa isotype.

4. The monoclonal antibody of claim 1 that is an intact antibody.

5. The monoclonal antibody of claim 1 that is a single-chain antibody, Fab or Fab'2 fragment.

6. A pharmaceutical composition comprising a monoclonal antibody as defined by claim 1.

7. A humanized or chimeric ABC2 antibody that specifically binds to CD122, comprising a light chain comprising three CDRs of the ABC2 light chain (SEQ ID NO:30) and a heavy chain comprising three CDRs of the ABC2 heavy chain (SEQ ID NO:25).

8. The antibody of claim 7, which is a humanized antibody.

9. A humanized antibody of claim 7 comprising a humanized mature light chain variable region having an amino acid sequence at least 90% identical to SEQ ID NO:42 and a humanized mature heavy chain variable region having an amino acid sequence at least 90% identical to SEQ ID NO.41.

10. The humanized antibody of claim 9, wherein the humanized mature light chain variable region has an amino acid sequence identical to SEQ ID NO:42 and the humanized mature heavy chain variable region has an amino acid sequence identical to SEQ ID NO.41.

11. The humanized antibody of claim 7, provided that positions H28, H48, H49, H68, H93 and L71 by Kabat numbering are occupied by residues T, I, A, I, A and Y respectively.

12. The humanized antibody of claim 11, further provided that position H42 by Kabat numbering is occupied by G.

13. The humanized antibody of claim 7, wherein the light chain CDRs are SEQ ID NOS. 27-29 and the heavy chain CDRs are SEQ ID NOS:22-24.

* * * * *

SEQUENCE LISTING

```
<160> NUMBER OF SEQ ID NOS: 77

<210> SEQ ID NO 1
<211> LENGTH: 420
<212> TYPE: DNA
<213> ORGANISM: Mus sp.
<220> FEATURE:
<221> NAME/KEY: CDS
<222> LOCATION: (1)..(420)

<400> SEQUENCE: 1 atg aag ttg tgg tta aac tgg gtt ttt ctt tta aca ctt tta cat ggt      48
Met Lys Leu Trp Leu Asn Trp Val Phe Leu Leu Thr Leu Leu His Gly
1               5                   10                  15 atc cag tgt gag gtg aag ctg gtg gaa tct gga gga ggc ttg gta cag      96
Ile Gln Cys Glu Val Lys Leu Val Glu Ser Gly Gly Gly Leu Val Gln
                20                  25                  30 cct ggg ggt tct ctg aga ctc tcc tgt gca act tct ggg ttc acc ttc     144
Pro Gly Gly Ser Leu Arg Leu Ser Cys Ala Thr Ser Gly Phe Thr Phe
            35                  40                  45 agt gat ttc tac atg gag tgg gtc cgc cag cct cca ggg aag aga ctg     192
Ser Asp Phe Tyr Met Glu Trp Val Arg Gln Pro Pro Gly Lys Arg Leu
        50                  55                  60 gag tgg att gct gca agt aga aac aaa gct aat gat tat aca aca gag     240
Glu Trp Ile Ala Ala Ser Arg Asn Lys Ala Asn Asp Tyr Thr Thr Glu
65                  70                  75                  80 tac agt gca tct gtg aag ggt cgg ttc atc gtc tcc aga gac act tcc     288
Tyr Ser Ala Ser Val Lys Gly Arg Phe Ile Val Ser Arg Asp Thr Ser
                85                  90                  95
```

```
caa agc atc ctc tac ctt cag atg aat gcc ctg aga gct gag gac act    336
Gln Ser Ile Leu Tyr Leu Gln Met Asn Ala Leu Arg Ala Glu Asp Thr
            100                 105                 110 gcc att tat tac tgt gca aga tcc tac tat agg tac gac ggt atg gac    384
Ala Ile Tyr Tyr Cys Ala Arg Ser Tyr Tyr Arg Tyr Asp Gly Met Asp
            115                 120                 125 tac tgg ggt caa gga acc tca gtc acc gtc tcc tca                    420
Tyr Trp Gly Gln Gly Thr Ser Val Thr Val Ser Ser
            130                 135                 140

<210> SEQ ID NO 2
<211> LENGTH: 140
<212> TYPE: PRT
<213> ORGANISM: Mus sp.

<400> SEQUENCE: 2

Met Lys Leu Trp Leu Asn Trp Val Phe Leu Leu Thr Leu Leu His Gly
1               5                   10                  15

Ile Gln Cys Glu Val Lys Leu Val Glu Ser Gly Gly Gly Leu Val Gln
            20                  25                  30

Pro Gly Gly Ser Leu Arg Leu Ser Cys Ala Thr Ser Gly Phe Thr Phe
        35                  40                  45

Ser Asp Phe Tyr Met Glu Trp Val Arg Gln Pro Pro Gly Lys Arg Leu
    50                  55                  60

Glu Trp Ile Ala Ala Ser Arg Asn Lys Ala Asn Asp Tyr Thr Thr Glu
65                  70                  75                  80

Tyr Ser Ala Ser Val Lys Gly Arg Phe Ile Val Ser Arg Asp Thr Ser
                85                  90                  95

Gln Ser Ile Leu Tyr Leu Gln Met Asn Ala Leu Arg Ala Glu Asp Thr
            100                 105                 110

Ala Ile Tyr Tyr Cys Ala Arg Ser Tyr Tyr Arg Tyr Asp Gly Met Asp
        115                 120                 125

Tyr Trp Gly Gln Gly Thr Ser Val Thr Val Ser Ser
    130                 135                 140

<210> SEQ ID NO 3
<211> LENGTH: 384
<212> TYPE: DNA
<213> ORGANISM: Mus sp.
<220> FEATURE:
<221> NAME/KEY: CDS
<222> LOCATION: (1)..(384)

<400> SEQUENCE: 3 atg gat ttt caa gtg cag att ttc agc ttc ctg cta atc agt gcc tca    48
Met Asp Phe Gln Val Gln Ile Phe Ser Phe Leu Leu Ile Ser Ala Ser
1               5                   10                  15 gtc ata gtg tcc aga gga caa gtt gtt ctc acc cag tct cca gta atc    96
Val Ile Val Ser Arg Gly Gln Val Val Leu Thr Gln Ser Pro Val Ile
            20                  25                  30 atg tct gca tct cca ggg gag aag gtc acc atg acc tgc agt gcc atc    144
Met Ser Ala Ser Pro Gly Glu Lys Val Thr Met Thr Cys Ser Ala Ile
        35                  40                  45 tca agt gta agt tac atg tac tgg tac cag cag aag cca gga tcc tcc    192
Ser Ser Val Ser Tyr Met Tyr Trp Tyr Gln Gln Lys Pro Gly Ser Ser
    50                  55                  60 ccc aga ctc ctg att tat gac aca tcc aac ctg gtt tct gga gtc cct    240
Pro Arg Leu Leu Ile Tyr Asp Thr Ser Asn Leu Val Ser Gly Val Pro
65                  70                  75                  80
```

| | | |
|---|---|---|
| gtt cgc ttc agt ggc agt ggg tct ggg acc tct tac tct ctc aca atc<br>Val Arg Phe Ser Gly Ser Gly Ser Gly Thr Ser Tyr Ser Leu Thr Ile<br>                              85                            90                       95 | | 288 |
| agc cga atg gag gct gaa gat gct gcc act tat tac tgc cag cag tgg<br>Ser Arg Met Glu Ala Glu Asp Ala Ala Thr Tyr Tyr Cys Gln Gln Trp<br>                              100                       105                    110 | | 336 |
| aat act tac ccg tac acg ttc gga ggg ggg acc aag ctg gaa ata aaa<br>Asn Thr Tyr Pro Tyr Thr Phe Gly Gly Gly Thr Lys Leu Glu Ile Lys<br>         115                    120                    125 | | 384 |

<210> SEQ ID NO 4
<211> LENGTH: 128
<212> TYPE: PRT
<213> ORGANISM: Mus sp.

<400> SEQUENCE: 4

Met Asp Phe Gln Val Gln Ile Phe Ser Phe Leu Leu Ile Ser Ala Ser
1               5                   10                  15

Val Ile Val Ser Arg Gly Gln Val Val Leu Thr Gln Ser Pro Val Ile
                20                  25                  30

Met Ser Ala Ser Pro Gly Glu Lys Val Thr Met Thr Cys Ser Ala Ile
            35                  40                  45

Ser Ser Val Ser Tyr Met Tyr Trp Tyr Gln Gln Lys Pro Gly Ser Ser
        50                  55                  60

Pro Arg Leu Leu Ile Tyr Asp Thr Ser Asn Leu Val Ser Gly Val Pro
65                  70                  75                  80

Val Arg Phe Ser Gly Ser Gly Ser Gly Thr Ser Tyr Ser Leu Thr Ile
                85                  90                  95

Ser Arg Met Glu Ala Glu Asp Ala Ala Thr Tyr Tyr Cys Gln Gln Trp
                100                 105                 110

Asn Thr Tyr Pro Tyr Thr Phe Gly Gly Gly Thr Lys Leu Glu Ile Lys
            115                 120                 125

<210> SEQ ID NO 5
<211> LENGTH: 417
<212> TYPE: DNA
<213> ORGANISM: Mus sp.
<220> FEATURE:
<221> NAME/KEY: CDS
<222> LOCATION: (1)..(417)

<400> SEQUENCE: 5

| | | |
|---|---|---|
| atg aga gtg ttg att ctt gtg tac ctg ttg aca gtc ctt cct ggt ata<br>Met Arg Val Leu Ile Leu Val Tyr Leu Leu Thr Val Leu Pro Gly Ile<br>1                 5                    10                  15 | | 48 |
| ctg tct gat gta cag ctt cag gag tca gga cct ggc ctg gtg aag cct<br>Leu Ser Asp Val Gln Leu Gln Glu Ser Gly Pro Gly Leu Val Lys Pro<br>                 20                    25                    30 | | 96 |
| tct cag aca gtg tcc ctc acc tgc act gtc act ggc tac tct atc act<br>Ser Gln Thr Val Ser Leu Thr Cys Thr Val Thr Gly Tyr Ser Ile Thr<br>         35                    40                    45 | | 144 |
| aat gat aat cac tgg tgg aac tgg atc cgg cag gtt tca gga agc aaa<br>Asn Asp Asn His Trp Trp Asn Trp Ile Arg Gln Val Ser Gly Ser Lys<br>     50                    55                    60 | | 192 |
| ctg gag tgg atg ggg tac ata gac tcc agt ggt agt tct gac aac aat<br>Leu Glu Trp Met Gly Tyr Ile Asp Ser Ser Gly Ser Ser Asp Asn Asn<br>65                   70                    75                  80 | | 240 |
| cca tct ctc aaa agt caa atc tcc atc act aga gac act tcc aag aac<br>Pro Ser Leu Lys Ser Gln Ile Ser Ile Thr Arg Asp Thr Ser Lys Asn<br>                 85                    90                    95 | | 288 |

```
cag tta ttc ctg cag ttg aac tct gtg act att gaa gat ata ggc aca      336
Gln Leu Phe Leu Gln Leu Asn Ser Val Thr Ile Glu Asp Ile Gly Thr
            100                 105                 110 tat tac tgt gca aga ggc ggt ggt agg gat tac tat ggc atg gac tac      384
Tyr Tyr Cys Ala Arg Gly Gly Gly Arg Asp Tyr Tyr Gly Met Asp Tyr
            115                 120                 125 tgg ggt caa gga acc tca gtc acc gtc tcc tca                          417
Trp Gly Gln Gly Thr Ser Val Thr Val Ser Ser
130                 135

<210> SEQ ID NO 6
<211> LENGTH: 139
<212> TYPE: PRT
<213> ORGANISM: Mus sp.

<400> SEQUENCE: 6

Met Arg Val Leu Ile Leu Val Tyr Leu Leu Thr Val Leu Pro Gly Ile
1               5                   10                  15

Leu Ser Asp Val Gln Leu Gln Glu Ser Gly Pro Gly Leu Val Lys Pro
            20                  25                  30

Ser Gln Thr Val Ser Leu Thr Cys Thr Val Thr Gly Tyr Ser Ile Thr
        35                  40                  45

Asn Asp Asn His Trp Trp Asn Trp Ile Arg Gln Val Ser Gly Ser Lys
    50                  55                  60

Leu Glu Trp Met Gly Tyr Ile Asp Ser Ser Gly Ser Ser Asp Asn Asn
65                  70                  75                  80

Pro Ser Leu Lys Ser Gln Ile Ser Ile Thr Arg Asp Thr Ser Lys Asn
                85                  90                  95

Gln Leu Phe Leu Gln Leu Asn Ser Val Thr Ile Glu Asp Ile Gly Thr
            100                 105                 110

Tyr Tyr Cys Ala Arg Gly Gly Gly Arg Asp Tyr Tyr Gly Met Asp Tyr
        115                 120                 125

Trp Gly Gln Gly Thr Ser Val Thr Val Ser Ser
    130                 135

<210> SEQ ID NO 7
<211> LENGTH: 393
<212> TYPE: DNA
<213> ORGANISM: Mus sp.
<220> FEATURE:
<221> NAME/KEY: CDS
<222> LOCATION: (1)..(393)

<400> SEQUENCE: 7 atg gag aca gac aca ctc ctg cta tgg gtg ctg ctg ctc tgg gtt cca      48
Met Glu Thr Asp Thr Leu Leu Leu Trp Val Leu Leu Leu Trp Val Pro
1               5                   10                  15 ggt tcc act ggt gac att gtg ctg aca cag tct cct gct tcc tta gct      96
Gly Ser Thr Gly Asp Ile Val Leu Thr Gln Ser Pro Ala Ser Leu Ala
            20                  25                  30 gta tct ctg ggg cag agg gcc acc atc tca tgc agg gcc agc caa agt      144
Val Ser Leu Gly Gln Arg Ala Thr Ile Ser Cys Arg Ala Ser Gln Ser
        35                  40                  45 gtc agt aca tct agc tat agt tat gtt cac tgg tac caa cag aaa cca      192
Val Ser Thr Ser Ser Tyr Ser Tyr Val His Trp Tyr Gln Gln Lys Pro
    50                  55                  60 gga cag cca ccc aaa ctc ctc atc aag tat gca tcc aac cta gaa tct      240
Gly Gln Pro Pro Lys Leu Leu Ile Lys Tyr Ala Ser Asn Leu Glu Ser
65                  70                  75                  80 ggg gtc cct gcc agg ttc agt ggc agt ggg tct ggg aca gac ttc acc      288
Gly Val Pro Ala Arg Phe Ser Gly Ser Gly Ser Gly Thr Asp Phe Thr
```

```
Gly Val Pro Ala Arg Phe Ser Gly Ser Gly Ser Gly Thr Asp Phe Thr
                85                  90                  95 ctc aac atc cat cct gtg gag gag gag gat act gca aca tat tac tgt    336
Leu Asn Ile His Pro Val Glu Glu Glu Asp Thr Ala Thr Tyr Tyr Cys
            100                 105                 110 cag cac agt tgg gac att ccg ttc acg ttc gga ggg ggg acc aag ctg    384
Gln His Ser Trp Asp Ile Pro Phe Thr Phe Gly Gly Gly Thr Lys Leu
        115                 120                 125 gaa ata aaa                                                         393
Glu Ile Lys
    130

<210> SEQ ID NO 8
<211> LENGTH: 131
<212> TYPE: PRT
<213> ORGANISM: Mus sp.

<400> SEQUENCE: 8

Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Ala Ser Leu Ala
            20                  25                  30

Val Ser Leu Gly Gln Arg Ala Thr Ile Ser Cys Arg Ala Ser Gln Ser
        35                  40                  45

Val Ser Thr Ser Ser Tyr Ser Tyr Val His Trp Tyr Gln Gln Lys Pro
    50                  55                  60

Gly Gln Pro Pro Lys Leu Leu Ile Lys Tyr Ala Ser Asn Leu Glu Ser
65                  70                  75                  80

Gly Val Pro Ala Arg Phe Ser Gly Ser Gly Ser Gly Thr Asp Phe Thr
                85                  90                  95

Leu Asn Ile His Pro Val Glu Glu Glu Asp Thr Ala Thr Tyr Tyr Cys
            100                 105                 110

Gln His Ser Trp Asp Ile Pro Phe Thr Phe Gly Gly Gly Thr Lys Leu
        115                 120                 125

Glu Ile Lys
    130

<210> SEQ ID NO 9
<211> LENGTH: 455
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (13)..(432)

<400> SEQUENCE: 9
actagtacca cc atg aag ttg tgg ttg aac tgg gtt ttt ctt ttg aca ctt    51
           Met Lys Leu Trp Leu Asn Trp Val Phe Leu Leu Thr Leu
           1               5                   10 ttg cat gga atc cag tgt gaa gtg cag ctc gtg gaa tct gga gga ggc    99
Leu His Gly Ile Gln Cys Glu Val Gln Leu Val Glu Ser Gly Gly Gly
    15                  20                  25 ttg gtt cag cct ggg gga tct ctg aga ctc tcc tgt gca gcc tct ggg    147
Leu Val Gln Pro Gly Gly Ser Leu Arg Leu Ser Cys Ala Ala Ser Gly
30                  35                  40                  45 ttc acc ttc agt gat ttc tac atg gag tgg gtc cgc cag gct cca ggg    195
Phe Thr Phe Ser Asp Phe Tyr Met Glu Trp Val Arg Gln Ala Pro Gly
            50                  55                  60
```

```
aag ggg ctc gag tgg att gct gca agt aga aac aaa gct aat gat tat      243
Lys Gly Leu Glu Trp Ile Ala Ala Ser Arg Asn Lys Ala Asn Asp Tyr
            65                  70                  75 aca aca gag tac agt gca tct gtg aag ggt cgg ttc atc gtc tcc aga      291
Thr Thr Glu Tyr Ser Ala Ser Val Lys Gly Arg Phe Ile Val Ser Arg
        80                  85                  90 gac gat tcc aag aac tca ctc tac ctt cag atg aat agc ctg aaa acc      339
Asp Asp Ser Lys Asn Ser Leu Tyr Leu Gln Met Asn Ser Leu Lys Thr
 95                 100                 105 gag gac act gcc gtg tat tac tgt gca aga tcc tac tat agg tac gac      387
Glu Asp Thr Ala Val Tyr Tyr Cys Ala Arg Ser Tyr Tyr Arg Tyr Asp
110                 115                 120                 125 ggt atg gac tac tgg ggt caa gga acc aca gtc acc gtc tcc tca          432
Gly Met Asp Tyr Trp Gly Gln Gly Thr Thr Val Thr Val Ser Ser
                130                 135                 140 ggtaagttgg cttttttaag ctt                                            455

<210> SEQ ID NO 10
<211> LENGTH: 140
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Lys Leu Trp Leu Asn Trp Val Phe Leu Thr Leu Leu His Gly
1               5                   10                  15

Ile Gln Cys Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Asp Phe Tyr Met Glu Trp Val Arg Gln Ala Pro Gly Lys Gly Leu
    50                  55                  60

Glu Trp Ile Ala Ala Ser Arg Asn Lys Ala Asn Asp Tyr Thr Thr Glu
65                  70                  75                  80

Tyr Ser Ala Ser Val Lys Gly Arg Phe Ile Val Ser Arg Asp Asp Ser
                85                  90                  95

Lys Asn Ser Leu Tyr Leu Gln Met Asn Ser Leu Lys Thr Glu Asp Thr
            100                 105                 110

Ala Val Tyr Tyr Cys Ala Arg Ser Tyr Tyr Arg Tyr Asp Gly Met Asp
        115                 120                 125

Tyr Trp Gly Gln Gly Thr Thr Val Thr Val Ser Ser
    130                 135                 140

<210> SEQ ID NO 11
<211> LENGTH: 418
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (13)..(396)

<400> SEQUENCE: 11
gctagcacca cc atg gat ttt caa gtg cag att ttc agc ttc ctg ctg atc     51
              Met Asp Phe Gln Val Gln Ile Phe Ser Phe Leu Leu Ile
               1               5                   10
```

```
agt gcc tca gtc atc gtg tcc aga gga gaa att gtg ctc acc cag tct      99
Ser Ala Ser Val Ile Val Ser Arg Gly Glu Ile Val Leu Thr Gln Ser
 15                  20                  25 cca gcc acc ctg tct ttg tct cca ggg gag aga gcc acc ctc tcc tgc     147
Pro Ala Thr Leu Ser Leu Ser Pro Gly Glu Arg Ala Thr Leu Ser Cys
 30                  35                  40                  45 agt gcc atc tca agt gtg agt tac atg tac tgg tac cag cag aag cca     195
Ser Ala Ile Ser Ser Val Ser Tyr Met Tyr Trp Tyr Gln Gln Lys Pro
                 50                  55                  60 gga cag gct ccc aga ctc ctg att tat gac aca tcc aac ctg gtg tct     243
Gly Gln Ala Pro Arg Leu Leu Ile Tyr Asp Thr Ser Asn Leu Val Ser
             65                  70                  75 gga gtc cct gcc cgc ttc agt ggc agt gga tct ggg acc gac tac act     291
Gly Val Pro Ala Arg Phe Ser Gly Ser Gly Ser Gly Thr Asp Tyr Thr
         80                  85                  90 ctc aca atc agc agc ctg gag cct gaa gat ttt gcc gtt tat tac tgc     339
Leu Thr Ile Ser Ser Leu Glu Pro Glu Asp Phe Ala Val Tyr Tyr Cys
     95                 100                 105 cag cag tgg aat act tac ccc tac acc ttc gga ggg ggg acc aaa gtg     387
Gln Gln Trp Asn Thr Tyr Pro Tyr Thr Phe Gly Gly Gly Thr Lys Val
110                 115                 120                 125 gaa atc aaa cgtaagtaga atccaagaat tc                                 418
Glu Ile Lys
```

<210> SEQ ID NO 12
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

```
Met Asp Phe Gln Val Gln Ile Phe Ser Phe Leu Leu Ile Ser Ala Ser
  1               5                  10                  15

Val Ile Val Ser Arg Gly Glu Ile Val Leu Thr Gln Ser Pro Ala Thr
                 20                  25                  30

Leu Ser Leu Ser Pro Gly Glu Arg Ala Thr Leu Ser Cys Ser Ala Ile
             35                  40                  45

Ser Ser Val Ser Tyr Met Tyr Trp Tyr Gln Gln Lys Pro Gly Gln Ala
         50                  55                  60

Pro Arg Leu Leu Ile Tyr Asp Thr Ser Asn Leu Val Ser Gly Val Pro
 65                  70                  75                  80

Ala Arg Phe Ser Gly Ser Gly Ser Gly Thr Asp Tyr Thr Leu Thr Ile
                 85                  90                  95

Ser Ser Leu Glu Pro Glu Asp Phe Ala Val Tyr Tyr Cys Gln Gln Trp
            100                 105                 110

Asn Thr Tyr Pro Tyr Thr Phe Gly Gly Gly Thr Lys Val Glu Ile Lys
        115                 120                 125
```

<210> SEQ ID NO 13
<211> LENGTH: 452
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (13)..(429)

<400> SEQUENCE: 13

```
actagtacca cc atg aga gtg ttg att ctt gtg tac ctg ttg aca gtc ctt        51
              Met Arg Val Leu Ile Leu Val Tyr Leu Leu Thr Val Leu
              1               5                   10 cct ggt att ctg tct cag gta cag ctt cag gag tca gga cct ggc ctg          99
Pro Gly Ile Leu Ser Gln Val Gln Leu Gln Glu Ser Gly Pro Gly Leu
        15                  20                  25 gtc aag cct tct cag aca ctg tcc ctc acc tgc act gtc tct ggc tac         147
Val Lys Pro Ser Gln Thr Leu Ser Leu Thr Cys Thr Val Ser Gly Tyr
30                  35                  40                  45 tct atc act aat gat aat cac tgg tgg aac tgg atc cgg cag cac cca         195
Ser Ile Thr Asn Asp Asn His Trp Trp Asn Trp Ile Arg Gln His Pro
                50                  55                  60 gga aag ggc ctg gaa tgg atg ggg tac atc gac tcc agt ggt tcc tct         243
Gly Lys Gly Leu Glu Trp Met Gly Tyr Ile Asp Ser Ser Gly Ser Ser
            65                  70                  75 gac aac aat cca tct ctc aaa agt caa atc acc atc tca aga gac act         291
Asp Asn Asn Pro Ser Leu Lys Ser Gln Ile Thr Ile Ser Arg Asp Thr
        80                  85                  90 tcc aag aac cag ctc tcc ctg aag ttg agc tct gtg act gcc gcc gat         339
Ser Lys Asn Gln Leu Ser Leu Lys Leu Ser Ser Val Thr Ala Ala Asp
95                  100                 105 aca gcc gtg tat tac tgt gca aga ggc gga ggc agg gat tac tat ggc         387
Thr Ala Val Tyr Tyr Cys Ala Arg Gly Gly Gly Arg Asp Tyr Tyr Gly
                115                 120                 125
110 atg gac tac tgg ggt caa gga acc acc gtc acc gtc tcc tca                 429
Met Asp Tyr Trp Gly Gln Gly Thr Thr Val Thr Val Ser Ser
            130                 135 ggtaagaatg gcctctcaag ctt                                                452

<210> SEQ ID NO 14
<211> LENGTH: 139
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Met Arg Val Leu Ile Leu Val Tyr Leu Leu Thr Val Leu Pro Gly Ile
1               5                   10                  15

Leu Ser Gln Val Gln Leu Gln Glu Ser Gly Pro Gly Leu Val Lys Pro
            20                  25                  30

Ser Gln Thr Leu Ser Leu Thr Cys Thr Val Ser Gly Tyr Ser Ile Thr
        35                  40                  45

Asn Asp Asn His Trp Trp Asn Trp Ile Arg Gln His Pro Gly Lys Gly
    50                  55                  60

Leu Glu Trp Met Gly Tyr Ile Asp Ser Ser Gly Ser Ser Asp Asn Asn
65                  70                  75                  80

Pro Ser Leu Lys Ser Gln Ile Thr Ile Ser Arg Asp Thr Ser Lys Asn
                85                  90                  95

Gln Leu Ser Leu Lys Leu Ser Ser Val Thr Ala Ala Asp Thr Ala Val
            100                 105                 110

Tyr Tyr Cys Ala Arg Gly Gly Gly Arg Asp Tyr Tyr Gly Met Asp Tyr
        115                 120                 125

Trp Gly Gln Gly Thr Thr Val Thr Val Ser Ser
    130                 135

<210> SEQ ID NO 15
```

```
<211> LENGTH: 428
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (13)..(405)

<400> SEQUENCE: 15
gctagcacca cc atg gag aca gac aca ctc ctg cta tgg gtg ctg ctg ctc      51
              Met Glu Thr Asp Thr Leu Leu Leu Trp Val Leu Leu Leu
                1               5                  10 tgg gtt cca ggt tcc act ggt gac att gtg atg aca cag tct cct gac        99
Trp Val Pro Gly Ser Thr Gly Asp Ile Val Met Thr Gln Ser Pro Asp
 15                  20                  25 tcc tta ggc gta tct ctg ggg gag agg gcc acc atc aac tgc agg gcc       147
Ser Leu Gly Val Ser Leu Gly Glu Arg Ala Thr Ile Asn Cys Arg Ala
 30                  35                  40                  45 agc caa agt gtc agc aca tct agc tat agt tat gtt cac tgg tac caa       195
Ser Gln Ser Val Ser Thr Ser Ser Tyr Ser Tyr Val His Trp Tyr Gln
                 50                  55                  60 cag aaa cca gga cag cca ccc aaa ctc ctc atc aag tat gca tcc aac       243
Gln Lys Pro Gly Gln Pro Pro Lys Leu Leu Ile Lys Tyr Ala Ser Asn
             65                  70                  75 cta gaa tct ggg gtc cct gac agg ttc agc ggc tct ggg tct ggg aca       291
Leu Glu Ser Gly Val Pro Asp Arg Phe Ser Gly Ser Gly Ser Gly Thr
         80                  85                  90 gac ttc acc ctc acc atc agc agc ctg cag gct gag gat gtg gca gtc       339
Asp Phe Thr Leu Thr Ile Ser Ser Leu Gln Ala Glu Asp Val Ala Val
     95                 100                 105 tat tac tgt cag cac agt tgg gac att ccc ttc aca ttc gga cag ggg       387
Tyr Tyr Cys Gln His Ser Trp Asp Ile Pro Phe Thr Phe Gly Gln Gly
110                 115                 120                 125 acc aaa ctc gaa atc aaa cgtaagtagt cttctcagaa ttc                     428
Thr Lys Leu Glu Ile Lys
                130

<210> SEQ ID NO 16
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Met Glu Thr Asp Thr Leu Leu Leu Trp Val Leu Leu Leu Trp Val Pro
  1               5                  10                  15

Gly Ser Thr Gly Asp Ile Val Met Thr Gln Ser Pro Asp Ser Leu Gly
             20                  25                  30

Val Ser Leu Gly Glu Arg Ala Thr Ile Asn Cys Arg Ala Ser Gln Ser
         35                  40                  45

Val Ser Thr Ser Ser Tyr Ser Tyr Val His Trp Tyr Gln Gln Lys Pro
     50                  55                  60

Gly Gln Pro Pro Lys Leu Leu Ile Lys Tyr Ala Ser Asn Leu Glu Ser
 65                  70                  75                  80

Gly Val Pro Asp Arg Phe Ser Gly Ser Gly Ser Gly Thr Asp Phe Thr
                 85                  90                  95

Leu Thr Ile Ser Ser Leu Gln Ala Glu Asp Val Ala Val Tyr Tyr Cys
            100                 105                 110
```

```
Gln His Ser Trp Asp Ile Pro Phe Thr Phe Gly Gln Gly Thr Lys Leu
        115                 120                 125
Glu Ile Lys
    130

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gccagtggat agacagatgg                                                  20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gccagtggat agaccgatgg                                                  20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gccagtggat agactgatgg                                                  20

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gatggataca gttggtgcag c                                                21

<210> SEQ ID NO 21
<211> LENGTH: 19
<212> TYPE: PRT
<213> ORGANISM: Mus sp.

<400> SEQUENCE: 21

Met Lys Leu Trp Leu Asn Trp Val Phe Leu Leu Thr Leu Leu His Gly
1               5                   10                  15
Ile Gln Cys

<210> SEQ ID NO 22
<211> LENGTH: 5
<212> TYPE: PRT
<213> ORGANISM: Mus sp.

<400> SEQUENCE: 22
```

```
Asp Phe Tyr Met Glu
1               5

<210> SEQ ID NO 23
<211> LENGTH: 19
<212> TYPE: PRT
<213> ORGANISM: Mus sp.

<400> SEQUENCE: 23

Ala Ser Arg Asn Lys Ala Asn Asp Tyr Thr Thr Glu Tyr Ser Ala Ser
1               5                   10                  15

Val Lys Gly

<210> SEQ ID NO 24
<211> LENGTH: 10
<212> TYPE: PRT
<213> ORGANISM: Mus sp.

<400> SEQUENCE: 24

Ser Tyr Tyr Arg Tyr Asp Gly Met Asp Tyr
1               5                   10

<210> SEQ ID NO 25
<211> LENGTH: 121
<212> TYPE: PRT
<213> ORGANISM: Mus sp.

<400> SEQUENCE: 25

Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Ser Asp Phe
            20                  25                  30

Tyr Met Glu Trp Val Arg Gln Pro Pro Gly Lys Arg Leu Glu Trp Ile
        35                  40                  45

Ala Ala Ser Arg Asn Lys Ala Asn Asp Tyr Thr Thr Glu Tyr Ser Ala
    50                  55                  60

Ser Val Lys Gly Arg Phe Ile Val Ser Arg Asp Thr Ser Gln Ser Ile
65                  70                  75                  80

Leu Tyr Leu Gln Met Asn Ala Leu Arg Ala Glu Asp Thr Ala Ile Tyr
                85                  90                  95

Tyr Cys Ala Arg Ser Tyr Tyr Arg Tyr Asp Gly Met Asp Tyr Trp Gly
            100                 105                 110

Gln Gly Thr Ser Val Thr Val Ser Ser
        115                 120

<210> SEQ ID NO 26
<211> LENGTH: 22
<212> TYPE: PRT
<213> ORGANISM: Mus sp.

<400> SEQUENCE: 26

Met Asp Phe Gln Val Gln Ile Phe Ser Phe Leu Leu Ile Ser Ala Ser
1               5                   10                  15

Val Ile Val Ser Arg Gly
            20

<210> SEQ ID NO 27
<211> LENGTH: 10
<212> TYPE: PRT
<213> ORGANISM: Mus sp.
```

-continued

```
<400> SEQUENCE: 27

Ser Ala Ile Ser Ser Val Ser Tyr Met Tyr
1               5                   10

<210> SEQ ID NO 28
<211> LENGTH: 7
<212> TYPE: PRT
<213> ORGANISM: Mus sp.

<400> SEQUENCE: 28

Asp Thr Ser Asn Leu Val Ser
1               5

<210> SEQ ID NO 29
<211> LENGTH: 9
<212> TYPE: PRT
<213> ORGANISM: Mus sp.

<400> SEQUENCE: 29

Gln Gln Trp Asn Thr Tyr Pro Tyr Thr
1               5

<210> SEQ ID NO 30
<211> LENGTH: 106
<212> TYPE: PRT
<213> ORGANISM: Mus sp.

<400> SEQUENCE: 30

Gln Val Val Leu Thr Gln Ser Pro Val Ile Met Ser Ala Ser Pro Gly
1               5                   10                  15

Glu Lys Val Thr Met Thr Cys Ser Ala Ile Ser Ser Val Ser Tyr Met
                20                  25                  30

Tyr Trp Tyr Gln Gln Lys Pro Gly Ser Ser Pro Arg Leu Leu Ile Tyr
            35                  40                  45

Asp Thr Ser Asn Leu Val Ser Gly Val Pro Val Arg Phe Ser Gly Ser
        50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Trp Asn Thr Tyr Pro Tyr Thr
                85                  90                  95

Phe Gly Gly Gly Thr Lys Leu Glu Ile Lys
            100                 105

<210> SEQ ID NO 31
<211> LENGTH: 18
<212> TYPE: PRT
<213> ORGANISM: Mus sp.

<400> SEQUENCE: 31

Met Arg Val Leu Ile Leu Val Tyr Leu Leu Thr Val Leu Pro Gly Ile
1               5                   10                  15

Leu Ser

<210> SEQ ID NO 32
<211> LENGTH: 7
<212> TYPE: PRT
<213> ORGANISM: Mus sp.

<400> SEQUENCE: 32

Asn Asp Asn His Trp Trp Asn
```

<210> SEQ ID NO 33
<211> LENGTH: 16
<212> TYPE: PRT
<213> ORGANISM: Mus sp.

<400> SEQUENCE: 33

Tyr Ile Asp Ser Ser Gly Ser Ser Asp Asn Asn Pro Ser Leu Lys Ser
1               5                   10                  15

<210> SEQ ID NO 34
<211> LENGTH: 11
<212> TYPE: PRT
<213> ORGANISM: Mus sp.

<400> SEQUENCE: 34

Gly Gly Gly Arg Asp Tyr Tyr Gly Met Asp Tyr
1               5                   10

<210> SEQ ID NO 35
<211> LENGTH: 121
<212> TYPE: PRT
<213> ORGANISM: Mus sp.

<400> SEQUENCE: 35

Asp Val Gln Leu Gln Glu Ser Gly Pro Gly Leu Val Lys Pro Ser Gln
1               5                   10                  15

Thr Val Ser Leu Thr Cys Thr Val Thr Gly Tyr Ser Ile Thr Asn Asp
            20                  25                  30

Asn His Trp Asn Trp Ile Arg Gln Val Ser Gly Ser Lys Leu Glu
        35                  40                  45

Trp Met Gly Tyr Ile Asp Ser Ser Gly Ser Ser Asp Asn Asn Pro Ser
    50                  55                  60

Leu Lys Ser Gln Ile Ser Ile Thr Arg Asp Thr Ser Lys Asn Gln Leu
65                  70                  75                  80

Phe Leu Gln Leu Asn Ser Val Thr Ile Glu Asp Ile Gly Thr Tyr Tyr
                85                  90                  95

Cys Ala Arg Gly Gly Gly Arg Asp Tyr Tyr Gly Met Asp Tyr Trp Gly
            100                 105                 110

Gln Gly Thr Ser Val Thr Val Ser Ser
        115                 120

<210> SEQ ID NO 36
<211> LENGTH: 20
<212> TYPE: PRT
<213> ORGANISM: Mus sp.

<400> SEQUENCE: 36

Met Glu Thr Asp Thr Leu Leu Leu Trp Val Leu Leu Leu Trp Val Pro
1               5                   10                  15

Gly Ser Thr Gly
            20

<210> SEQ ID NO 37
<211> LENGTH: 15
<212> TYPE: PRT
<213> ORGANISM: Mus sp.

<400> SEQUENCE: 37

Arg Ala Ser Gln Ser Val Ser Thr Ser Ser Tyr Ser Tyr Val His

<210> SEQ ID NO 38
<211> LENGTH: 7
<212> TYPE: PRT
<213> ORGANISM: Mus sp.

<400> SEQUENCE: 38

Tyr Ala Ser Asn Leu Glu Ser
1               5

<210> SEQ ID NO 39
<211> LENGTH: 9
<212> TYPE: PRT
<213> ORGANISM: Mus sp.

<400> SEQUENCE: 39

Gln His Ser Trp Asp Ile Pro Phe Thr
1               5

<210> SEQ ID NO 40
<211> LENGTH: 111
<212> TYPE: PRT
<213> ORGANISM: Mus sp.

<400> SEQUENCE: 40

Asp Ile Val Leu Thr Gln Ser Pro Ala Ser Leu Ala Val Ser Leu Gly
1               5                   10                  15

Gln Arg Ala Thr Ile Ser Cys Arg Ala Ser Gln Ser Val Ser Thr Ser
            20                  25                  30

Ser Tyr Ser Tyr Val His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Thr Ala Thr Tyr Tyr Cys Gln His Ser Trp
                85                  90                  95

Asp Ile Pro Phe Thr Phe Gly Gly Gly Thr Lys Leu Glu Ile Lys
            100                 105                 110

<210> SEQ ID NO 41
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Phe
            20                  25                  30

Tyr Met Glu Trp Val Arg Gln Ala Pro Gly Lys Gly Leu Glu Trp Ile
        35                  40                  45

Ala Ala Ser Arg Asn Lys Ala Asn Asp Tyr Thr Thr Glu Tyr Ser Ala
    50                  55                  60

Ser Val Lys Gly Arg Phe Ile Val Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Ser Tyr Arg Tyr Asp Gly Met Asp Tyr Trp Gly
            100                 105                 110

Gln Gly Thr Thr Val Thr Val Ser Ser
        115                 120

<210> SEQ ID NO 42
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Glu Ile Val Leu Thr Gln Ser Pro Ala Thr Leu Ser Leu Ser Pro Gly
1               5                   10                  15

Glu Arg Ala Thr Leu Ser Cys Ser Ala Ile Ser Ser Val Ser Tyr Met
            20                  25                  30

Tyr Trp Tyr Gln Gln Lys Pro Gly Gln Ala Pro Arg Leu Leu Ile Tyr
        35                  40                  45

Asp Thr Ser Asn Leu Val Ser Gly Val Pro Ala Arg Phe Ser Gly Ser
50                  55                  60

Gly Ser Gly Thr Asp Tyr Thr Leu Thr Ile Ser Ser Leu Glu Pro Glu
65                  70                  75                  80

Asp Phe Ala Val Tyr Tyr Cys Gln Gln Trp Asn Thr Tyr Pro Tyr Thr
                85                  90                  95

Phe Gly Gly Gly Thr Lys Val Glu Ile Lys
            100                 105

<210> SEQ ID NO 43
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Asn Asp
            20                  25                  30

Asn His Trp Trp Asn Trp Ile Arg Gln His Pro Gly Lys Gly Leu Glu
        35                  40                  45

Trp Met Gly Tyr Ile Asp Ser Ser Gly Ser Asp Asn Asn Pro Ser
    50                  55                  60

Leu Lys Ser Gln Ile Thr Ile Ser Arg Asp Thr Ser Lys Asn Gln Leu
65                  70                  75                  80

Ser Leu Lys Leu Ser Ser Val Thr Ala Ala Asp Thr Ala Val Tyr Tyr
                85                  90                  95

Cys Ala Arg Gly Gly Gly Arg Asp Tyr Tyr Gly Met Asp Tyr Trp Gly
            100                 105                 110

Gln Gly Thr Thr Val Thr Val Ser Ser
        115                 120

<210> SEQ ID NO 44
<211> LENGTH: 111

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Asp Ile Val Met Thr Gln Ser Pro Asp Ser Leu Gly Val Ser Leu Gly
1               5                   10                  15

Glu Arg Ala Thr Ile Asn Cys Arg Ala Ser Gln Ser Val Ser Thr Ser
            20                  25                  30

Ser Tyr Ser Tyr Val His Trp Tyr Gln Gln Lys Pro Gly Gln Pro Pro
        35                  40                  45

Lys Leu Leu Ile Lys Tyr Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Trp
                85                  90                  95

Asp Ile Pro Phe Thr Phe Gly Gln Gly Thr Lys Leu Glu Ile Lys
            100                 105                 110

<210> SEQ ID NO 45
<211> LENGTH: 126
<212> TYPE: PRT
<213> ORGANISM: Homo sapiens

<400> SEQUENCE: 45

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Asp His
            20                  25                  30

Tyr Met Asp Trp Val Arg Gln Ala Pro Val Lys Gly Leu Glu Trp Val
        35                  40                  45

Gly Arg Thr Arg Asp Lys Ala Asn Ser Tyr Thr Thr Glu Tyr Ala Ala
    50                  55                  60

Ser Val Lys Gly Arg Phe Thr Val Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Val Arg Gly Gly Ala Ala Met Ala Arg Gly Tyr Gln Asp Gly
            100                 105                 110

Leu Asp Val Trp Gly Gln Gly Thr Thr Val Thr Val Ser Ser
        115                 120                 125

<210> SEQ ID NO 46
<211> LENGTH: 107
<212> TYPE: PRT
<213> ORGANISM: Homo sapiens

<400> SEQUENCE: 46

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Lys Ala Thr Gly Val Pro Ala Arg Phe Ser Gly
```

```
                    50                  55                  60
Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Ser Ser Lys Trp Pro Leu
                     85                  90                  95

Thr Phe Gly Gly Gly Thr Lys Val Glu Ile Lys
                100                 105

<210> SEQ ID NO 47
<211> LENGTH: 122
<212> TYPE: PRT
<213> ORGANISM: Homo sapiens

<400> SEQUENCE: 47

Gln Val Gln Leu Gln Glu Ser Gly Pro Gly Leu Val Lys Pro Ser Gln
  1               5                  10                  15

Thr Leu Ser Leu Thr Cys Thr Val Ser Gly Gly Ser Ile Asp Asn Thr
                 20                  25                  30

Gly Phe Tyr Trp Ser Trp Ile Arg Gln His Pro Gly Lys Gly Leu Glu
             35                  40                  45

Trp Ile Gly Asn Ile Tyr Tyr Ser Gly Ser Thr Tyr Tyr Asn Pro Ser
 50                  55                  60

Leu Lys Ser Arg Val Thr Ile Ser Val Asp Thr Ser Lys Asn Gln Leu
 65                  70                  75                  80

Ser Leu Lys Leu Ser Ser Val Thr Ala Ala Asp Thr Ala Val Tyr Tyr
                 85                  90                  95

Cys Ala Arg Asp Trp Gly Asn Ser Trp Asp Arg Gly Met Asp Val Trp
            100                 105                 110

Gly Gln Gly Thr Thr Val Thr Val Ser Ser
            115                 120

<210> SEQ ID NO 48
<211> LENGTH: 114
<212> TYPE: PRT
<213> ORGANISM: Homo sapiens

<400> SEQUENCE: 48

Asp Ile Val Met Thr Gln Ser Pro Asp Ser Leu Ala Val Ser Leu Gly
  1               5                  10                  15

Glu Arg Ala Thr Ile Asn Cys Lys Ser Ser Gln Ser Val Leu Tyr Ser
                 20                  25                  30

Ser Asn Asn Lys Asn Tyr Leu Ala Trp Tyr Gln Gln Lys Pro Gly Gln
             35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Tyr Tyr Ser Thr Pro Ser Tyr Thr Phe Gly Gln Gly Thr Lys Leu Glu
            100                 105                 110

Ile Lys

<210> SEQ ID NO 49
<211> LENGTH: 101
<212> TYPE: PRT
<213> ORGANISM: Homo sapiens
```

<400> SEQUENCE: 49

Ala Val Asn Gly Thr Ser Gln Phe Thr Cys Phe Tyr Asn Ser Arg Ala
1               5                   10                  15

Asn Ile Ser Cys Val Trp Ser Gln Asp Gly Ala Leu Gln Asp Thr Ser
            20                  25                  30

Cys Gln Val His Ala Trp Pro Asp Arg Arg Arg Trp Asn Gln Thr Cys
        35                  40                  45

Glu Leu Leu Pro Val Ser Gln Ala Ser Trp Ala Cys Asn Leu Ile Leu
    50                  55                  60

Gly Ala Pro Asp Ser Gln Lys Leu Thr Thr Val Asp Ile Val Thr Leu
65                  70                  75                  80

Arg Val Leu Cys Arg Glu Gly Val Arg Trp Arg Val Met Ala Ile Gln
                85                  90                  95

Asp Phe Lys Pro Phe
            100

<210> SEQ ID NO 50
<211> LENGTH: 113
<212> TYPE: PRT
<213> ORGANISM: Homo sapiens

<400> SEQUENCE: 50

Glu Asn Leu Arg Leu Met Ala Pro Ile Ser Leu Gln Val Val His Val
1               5                   10                  15

Glu Thr His Arg Cys Asn Ile Ser Trp Glu Ile Ser Gln Ala Ser His
            20                  25                  30

Tyr Phe Glu Arg His Leu Glu Phe Glu Ala Arg Thr Leu Ser Pro Gly
        35                  40                  45

His Thr Trp Glu Glu Ala Pro Leu Leu Thr Leu Lys Gln Lys Gln Glu
    50                  55                  60

Trp Ile Cys Leu Glu Thr Leu Thr Pro Asp Thr Gln Tyr Glu Phe Gln
65                  70                  75                  80

Val Arg Val Lys Pro Leu Gln Gly Glu Phe Thr Thr Trp Ser Pro Trp
                85                  90                  95

Ser Gln Pro Leu Ala Phe Arg Thr Lys Pro Ala Ala Leu Gly Lys Asp
            100                 105                 110

Thr

<210> SEQ ID NO 51
<211> LENGTH: 102
<212> TYPE: PRT
<213> ORGANISM: Mus sp.

<400> SEQUENCE: 51

Ala Val Lys Asn Cys Ser His Leu Glu Cys Phe Tyr Asn Ser Arg Ala
1               5                   10                  15

Asn Val Ser Cys Met Trp Ser His Glu Ala Leu Asn Val Thr Thr
            20                  25                  30

Cys His Val His Ala Lys Ser Asn Leu Arg His Trp Asn Lys Thr Cys
        35                  40                  45

Glu Leu Thr Leu Val Arg Gln Ala Ser Trp Ala Cys Asn Leu Ile Leu
    50                  55                  60

Gly Ser Phe Pro Glu Ser Gln Ser Leu Thr Ser Val Asp Leu Leu Asp
65                  70                  75                  80

Ile Asn Val Val Cys Trp Glu Glu Lys Gly Trp Arg Arg Val Lys Thr

```
                        85                  90                  95

Cys Asp Phe His Pro Phe
            100

<210> SEQ ID NO 52
<211> LENGTH: 113
<212> TYPE: PRT
<213> ORGANISM: Mus sp.

<400> SEQUENCE: 52

Asp Asn Leu Arg Leu Val Ala Pro His Ser Leu Gln Val Leu His Ile
1               5                   10                  15

Asp Thr Gln Arg Cys Asn Ile Ser Trp Lys Val Ser Gln Val Ser His
            20                  25                  30

Tyr Ile Glu Pro Tyr Leu Glu Phe Glu Ala Arg Arg Arg Leu Leu Gly
        35                  40                  45

His Ser Trp Glu Asp Ala Ser Val Leu Ser Leu Lys Gln Arg Gln Gln
    50                  55                  60

Trp Leu Phe Leu Glu Met Leu Ile Pro Ser Thr Ser Tyr Glu Val Gln
65                  70                  75                  80

Val Arg Val Lys Ala Gln Arg Asn Asn Thr Gly Thr Trp Ser Pro Trp
                85                  90                  95

Ser Gln Pro Leu Thr Phe Arg Thr Arg Pro Ala Asp Pro Met Lys Glu
            100                 105                 110

Ile

<210> SEQ ID NO 53
<211> LENGTH: 52
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Thr Gly Gly Gly Asp Tyr Lys Asp Asp Asp Lys Gly Gly Gly Pro
1               5                   10                  15

Asn Lys Gly Ser Gly Thr Thr Ser Gly Thr Thr Arg Leu Leu Ser Gly
            20                  25                  30

His Thr Cys Phe Thr Leu Thr Gly Leu Leu Gly Thr Leu Val Thr Met
        35                  40                  45

Gly Leu Leu Thr
    50

<210> SEQ ID NO 54
<211> LENGTH: 214
<212> TYPE: PRT
<213> ORGANISM: Homo sapiens

<400> SEQUENCE: 54

Ala Val Asn Gly Thr Ser Gln Phe Thr Cys Phe Tyr Asn Ser Arg Ala
1               5                   10                  15

Asn Ile Ser Cys Val Trp Ser Gln Asp Gly Ala Leu Gln Asp Thr Ser
            20                  25                  30

Cys Gln Val His Ala Trp Pro Asp Arg Arg Arg Trp Asn Gln Thr Cys
        35                  40                  45

Glu Leu Leu Pro Val Ser Gln Ala Ser Trp Ala Cys Asn Leu Ile Leu
    50                  55                  60
```

-continued

```
Gly Ala Pro Asp Ser Gln Lys Leu Thr Thr Val Asp Ile Val Thr Leu
 65                  70                  75                  80

Arg Val Leu Cys Arg Glu Gly Val Arg Trp Arg Val Met Ala Ile Gln
                 85                  90                  95

Asp Phe Lys Pro Phe Glu Asn Leu Arg Leu Met Ala Pro Ile Ser Leu
            100                 105                 110

Gln Val Val His Val Glu Thr His Arg Cys Asn Ile Ser Trp Glu Ile
        115                 120                 125

Ser Gln Ala Ser His Tyr Phe Glu Arg His Leu Glu Phe Glu Ala Arg
    130                 135                 140

Thr Leu Ser Pro Gly His Thr Trp Glu Glu Ala Pro Leu Leu Thr Leu
145                 150                 155                 160

Lys Gln Lys Gln Glu Trp Ile Cys Leu Glu Thr Leu Thr Pro Asp Thr
                165                 170                 175

Gln Tyr Glu Phe Gln Val Arg Val Lys Pro Leu Gln Gly Glu Phe Thr
            180                 185                 190

Thr Trp Ser Pro Trp Ser Gln Pro Leu Ala Phe Arg Thr Lys Pro Ala
        195                 200                 205

Ala Leu Gly Lys Asp Thr
    210
```

<210> SEQ ID NO 55
<211> LENGTH: 214
<212> TYPE: PRT
<213> ORGANISM: Homo sapiens

<400> SEQUENCE: 55

```
Ala Val Asn Gly Thr Ser Gln Phe Thr Cys Phe Tyr Asn Ser Arg Ala
  1               5                  10                  15

Asn Ile Ser Cys Val Trp Ser Gln Asp Gly Ala Leu Gln Asp Thr Ser
                 20                  25                  30

Cys Gln Val His Ala Lys Pro Asp Arg Arg Trp Asn Gln Thr Cys
             35                  40                  45

Glu Leu Leu Pro Val Ser Gln Ala Ser Trp Ala Cys Asn Leu Ile Leu
 50                  55                  60

Gly Ala Pro Asp Ser Gln Lys Leu Thr Thr Val Asp Ile Val Thr Leu
 65                  70                  75                  80

Arg Val Leu Cys Arg Glu Gly Val Arg Trp Arg Val Met Ala Ile Gln
                 85                  90                  95

Asp Phe Lys Pro Phe Glu Asn Leu Arg Leu Met Ala Pro Ile Ser Leu
            100                 105                 110

Gln Val Val His Val Glu Thr His Arg Cys Asn Ile Ser Trp Glu Ile
        115                 120                 125

Ser Gln Ala Ser His Tyr Phe Glu Arg His Leu Glu Phe Glu Ala Arg
    130                 135                 140

Thr Leu Ser Pro Gly His Thr Trp Glu Glu Ala Pro Leu Leu Thr Leu
145                 150                 155                 160

Lys Gln Lys Gln Glu Trp Ile Cys Leu Glu Thr Leu Thr Pro Asp Thr
                165                 170                 175

Gln Tyr Glu Phe Gln Val Arg Val Lys Pro Leu Gln Gly Glu Phe Thr
            180                 185                 190

Thr Trp Ser Pro Trp Ser Gln Pro Leu Ala Phe Arg Thr Lys Pro Ala
        195                 200                 205

Ala Leu Gly Lys Asp Thr
    210
```

```
<210> SEQ ID NO 56
<211> LENGTH: 214
<212> TYPE: PRT
<213> ORGANISM: Homo sapiens

<400> SEQUENCE: 56

Ala Val Asn Gly Thr Ser Gln Phe Thr Cys Phe Tyr Asn Ser Arg Ala
1               5                   10                  15

Asn Ile Ser Cys Val Trp Ser Gln Asp Gly Ala Leu Gln Asp Thr Ser
                20                  25                  30

Cys Gln Val His Ala Trp Ser Asp Arg Arg Trp Asn Gln Thr Cys
                35                  40                  45

Glu Leu Leu Pro Val Ser Gln Ala Ser Trp Ala Cys Asn Leu Ile Leu
    50                  55                  60

Gly Ala Pro Asp Ser Gln Lys Leu Thr Thr Val Asp Ile Val Thr Leu
65                  70                  75                  80

Arg Val Leu Cys Arg Glu Gly Val Arg Trp Arg Val Met Ala Ile Gln
                85                  90                  95

Asp Phe Lys Pro Phe Glu Asn Leu Arg Leu Met Ala Pro Ile Ser Leu
                100                 105                 110

Gln Val Val His Val Glu Thr His Arg Cys Asn Ile Ser Trp Glu Ile
                115                 120                 125

Ser Gln Ala Ser His Tyr Phe Glu Arg His Leu Glu Phe Glu Ala Arg
    130                 135                 140

Thr Leu Ser Pro Gly His Thr Trp Glu Glu Ala Pro Leu Leu Thr Leu
145                 150                 155                 160

Lys Gln Lys Gln Glu Trp Ile Cys Leu Glu Thr Leu Thr Pro Asp Thr
                165                 170                 175

Gln Tyr Glu Phe Gln Val Arg Val Lys Pro Leu Gln Gly Glu Phe Thr
                180                 185                 190

Thr Trp Ser Pro Trp Ser Gln Pro Leu Ala Phe Arg Thr Lys Pro Ala
                195                 200                 205

Ala Leu Gly Lys Asp Thr
    210

<210> SEQ ID NO 57
<211> LENGTH: 214
<212> TYPE: PRT
<213> ORGANISM: Homo sapiens

<400> SEQUENCE: 57

Ala Val Asn Gly Thr Ser Gln Phe Thr Cys Phe Tyr Asn Ser Arg Ala
1               5                   10                  15

Asn Ile Ser Cys Val Trp Ser Gln Asp Gly Ala Leu Gln Asp Thr Ser
                20                  25                  30

Cys Gln Val His Ala Trp Pro Ala Arg Arg Trp Asn Gln Thr Cys
                35                  40                  45

Glu Leu Leu Pro Val Ser Gln Ala Ser Trp Ala Cys Asn Leu Ile Leu
    50                  55                  60

Gly Ala Pro Asp Ser Gln Lys Leu Thr Thr Val Asp Ile Val Thr Leu
65                  70                  75                  80

Arg Val Leu Cys Arg Glu Gly Val Arg Trp Arg Val Met Ala Ile Gln
                85                  90                  95

Asp Phe Lys Pro Phe Glu Asn Leu Arg Leu Met Ala Pro Ile Ser Leu
                100                 105                 110
```

```
Gln Val Val His Val Glu Thr His Arg Cys Asn Ile Ser Trp Glu Ile
            115                 120                 125

Ser Gln Ala Ser His Tyr Phe Glu Arg His Leu Glu Phe Glu Ala Arg
        130                 135                 140

Thr Leu Ser Pro Gly His Thr Trp Glu Glu Ala Pro Leu Leu Thr Leu
145                 150                 155                 160

Lys Gln Lys Gln Glu Trp Ile Cys Leu Glu Thr Leu Thr Pro Asp Thr
                165                 170                 175

Gln Tyr Glu Phe Gln Val Arg Val Lys Pro Leu Gln Gly Glu Phe Thr
            180                 185                 190

Thr Trp Ser Pro Trp Ser Gln Pro Leu Ala Phe Arg Thr Lys Pro Ala
        195                 200                 205

Ala Leu Gly Lys Asp Thr
    210

<210> SEQ ID NO 58
<211> LENGTH: 214
<212> TYPE: PRT
<213> ORGANISM: Homo sapiens

<400> SEQUENCE: 58

Ala Val Asn Gly Thr Ser Gln Phe Thr Cys Phe Tyr Asn Ser Arg Ala
1               5                   10                  15

Asn Ile Ser Cys Val Trp Ser Gln Asp Gly Ala Leu Gln Asp Thr Ser
            20                  25                  30

Cys Gln Val His Ala Trp Pro Asp Ala Arg Arg Trp Asn Gln Thr Cys
        35                  40                  45

Glu Leu Leu Pro Val Ser Gln Ala Ser Trp Ala Cys Asn Leu Ile Leu
    50                  55                  60

Gly Ala Pro Asp Ser Gln Lys Leu Thr Thr Val Asp Ile Val Thr Leu
65                  70                  75                  80

Arg Val Leu Cys Arg Glu Gly Val Arg Trp Arg Val Met Ala Ile Gln
                85                  90                  95

Asp Phe Lys Pro Phe Glu Asn Leu Arg Leu Met Ala Pro Ile Ser Leu
            100                 105                 110

Gln Val Val His Val Glu Thr His Arg Cys Asn Ile Ser Trp Glu Ile
            115                 120                 125

Ser Gln Ala Ser His Tyr Phe Glu Arg His Leu Glu Phe Glu Ala Arg
        130                 135                 140

Thr Leu Ser Pro Gly His Thr Trp Glu Glu Ala Pro Leu Leu Thr Leu
145                 150                 155                 160

Lys Gln Lys Gln Glu Trp Ile Cys Leu Glu Thr Leu Thr Pro Asp Thr
                165                 170                 175

Gln Tyr Glu Phe Gln Val Arg Val Lys Pro Leu Gln Gly Glu Phe Thr
            180                 185                 190

Thr Trp Ser Pro Trp Ser Gln Pro Leu Ala Phe Arg Thr Lys Pro Ala
        195                 200                 205

Ala Leu Gly Lys Asp Thr
    210

<210> SEQ ID NO 59
<211> LENGTH: 214
<212> TYPE: PRT
<213> ORGANISM: Homo sapiens

<400> SEQUENCE: 59
```

```
Ala Val Asn Gly Thr Ser Gln Phe Thr Cys Phe Tyr Asn Ser Arg Ala
1               5                   10                  15

Asn Ile Ser Cys Val Trp Ser Gln Asp Gly Ala Leu Gln Asp Thr Ser
            20                  25                  30

Cys Gln Val His Ala Trp Pro Asp Arg Ala Arg Trp Asn Gln Thr Cys
        35                  40                  45

Glu Leu Leu Pro Val Ser Gln Ala Ser Trp Ala Cys Asn Leu Ile Leu
50                  55                  60

Gly Ala Pro Asp Ser Gln Lys Leu Thr Thr Val Asp Ile Val Thr Leu
65                  70                  75                  80

Arg Val Leu Cys Arg Glu Gly Val Arg Trp Arg Val Met Ala Ile Gln
                85                  90                  95

Asp Phe Lys Pro Phe Glu Asn Leu Arg Leu Met Ala Pro Ile Ser Leu
            100                 105                 110

Gln Val Val His Val Glu Thr His Arg Cys Asn Ile Ser Trp Glu Ile
        115                 120                 125

Ser Gln Ala Ser His Tyr Phe Glu Arg His Leu Glu Phe Glu Ala Arg
130                 135                 140

Thr Leu Ser Pro Gly His Thr Trp Glu Glu Ala Pro Leu Leu Thr Leu
145                 150                 155                 160

Lys Gln Lys Gln Glu Trp Ile Cys Leu Glu Thr Leu Thr Pro Asp Thr
                165                 170                 175

Gln Tyr Glu Phe Gln Val Arg Val Lys Pro Leu Gln Gly Glu Phe Thr
            180                 185                 190

Thr Trp Ser Pro Trp Ser Gln Pro Leu Ala Phe Arg Thr Lys Pro Ala
        195                 200                 205

Ala Leu Gly Lys Asp Thr
210

<210> SEQ ID NO 60
<211> LENGTH: 214
<212> TYPE: PRT
<213> ORGANISM: Homo sapiens

<400> SEQUENCE: 60

Ala Val Asn Gly Thr Ser Gln Phe Thr Cys Phe Tyr Asn Ser Arg Ala
1               5                   10                  15

Asn Ile Ser Cys Val Trp Ser Gln Asp Gly Ala Leu Gln Asp Thr Ser
            20                  25                  30

Cys Gln Val His Ala Trp Pro Asp Arg Ala Arg Trp Asn Gln Thr Cys
        35                  40                  45

Glu Leu Leu Pro Val Ser Gln Ala Ser Trp Ala Cys Asn Leu Ile Leu
50                  55                  60

Gly Ala Pro Asp Ser Gln Lys Leu Thr Thr Val Asp Ile Val Thr Leu
65                  70                  75                  80

Arg Val Leu Cys Arg Glu Gly Val Arg Trp Arg Val Met Ala Ile Gln
                85                  90                  95

Asp Phe Lys Pro Phe Glu Asn Leu Arg Leu Met Ala Pro Ile Ser Leu
            100                 105                 110

Gln Val Val His Val Glu Thr His Arg Cys Asn Ile Ser Trp Glu Ile
        115                 120                 125

Ser Gln Ala Ser His Tyr Phe Glu Arg His Leu Glu Phe Glu Ala Arg
130                 135                 140

Thr Leu Ser Pro Gly His Thr Trp Glu Glu Ala Pro Leu Leu Thr Leu
```

```
145                 150                 155                 160
Lys Gln Lys Gln Glu Trp Ile Cys Leu Glu Thr Leu Thr Pro Asp Thr
                165                 170                 175
Gln Tyr Glu Phe Gln Val Arg Val Lys Pro Leu Gln Gly Glu Phe Thr
            180                 185                 190
Thr Trp Ser Pro Trp Ser Gln Pro Leu Ala Phe Arg Thr Lys Pro Ala
        195                 200                 205
Ala Leu Gly Lys Asp Thr
    210

<210> SEQ ID NO 61
<211> LENGTH: 214
<212> TYPE: PRT
<213> ORGANISM: Homo sapiens

<400> SEQUENCE: 61

Ala Val Asn Gly Thr Ser Gln Phe Thr Cys Phe Tyr Asn Ser Arg Ala
1               5                   10                  15
Asn Ile Ser Cys Val Trp Ser Gln Asp Gly Ala Leu Gln Asp Thr Ser
                20                  25                  30
Cys Gln Val His Ala Trp Pro Asp Arg Arg Ala Asn Gln Thr Cys
        35                  40                  45
Glu Leu Leu Pro Val Ser Gln Ala Ser Trp Ala Cys Asn Leu Ile Leu
    50                  55                  60
Gly Ala Pro Asp Ser Gln Lys Leu Thr Thr Val Asp Ile Val Thr Leu
65                  70                  75                  80
Arg Val Leu Cys Arg Glu Gly Val Arg Trp Arg Val Met Ala Ile Gln
                85                  90                  95
Asp Phe Lys Pro Phe Glu Asn Leu Arg Leu Met Ala Pro Ile Ser Leu
            100                 105                 110
Gln Val Val His Val Glu Thr His Arg Cys Asn Ile Ser Trp Glu Ile
        115                 120                 125
Ser Gln Ala Ser His Tyr Phe Glu Arg His Leu Glu Phe Glu Ala Arg
    130                 135                 140
Thr Leu Ser Pro Gly His Thr Trp Glu Glu Ala Pro Leu Leu Thr Leu
145                 150                 155                 160
Lys Gln Lys Gln Glu Trp Ile Cys Leu Glu Thr Leu Thr Pro Asp Thr
                165                 170                 175
Gln Tyr Glu Phe Gln Val Arg Val Lys Pro Leu Gln Gly Glu Phe Thr
            180                 185                 190
Thr Trp Ser Pro Trp Ser Gln Pro Leu Ala Phe Arg Thr Lys Pro Ala
        195                 200                 205
Ala Leu Gly Lys Asp Thr
    210

<210> SEQ ID NO 62
<211> LENGTH: 214
<212> TYPE: PRT
<213> ORGANISM: Homo sapiens

<400> SEQUENCE: 62

Ala Val Asn Gly Thr Ser Gln Phe Thr Cys Phe Tyr Asn Ser Arg Ala
1               5                   10                  15
Asn Ile Ser Cys Val Trp Ser Gln Asp Gly Ala Leu Gln Asp Thr Ser
                20                  25                  30
Cys Gln Val His Ala Trp Pro Asp Arg Arg Arg Trp Asn Gln Thr Cys
```

```
                    35                  40                  45
Glu Leu Leu Pro Val Ser Gln Ala Ser Trp Ala Cys Asn Leu Ile Ala
 50                  55                  60
Gly Ala Pro Asp Ser Gln Lys Leu Thr Thr Val Asp Ile Val Thr Leu
 65                  70                  75                  80
Arg Val Leu Cys Arg Glu Gly Val Arg Trp Arg Val Met Ala Ile Gln
                    85                  90                  95
Asp Phe Lys Pro Phe Glu Asn Leu Arg Leu Met Ala Pro Ile Ser Leu
                100                 105                 110
Gln Val Val His Val Glu Thr His Arg Cys Asn Ile Ser Trp Glu Ile
                115                 120                 125
Ser Gln Ala Ser His Tyr Phe Glu Arg His Leu Glu Phe Glu Ala Arg
    130                 135                 140
Thr Leu Ser Pro Gly His Thr Trp Glu Glu Ala Pro Leu Leu Thr Leu
145                 150                 155                 160
Lys Gln Lys Gln Glu Trp Ile Cys Leu Glu Thr Leu Thr Pro Asp Thr
                165                 170                 175
Gln Tyr Glu Phe Gln Val Arg Val Lys Pro Leu Gln Gly Glu Phe Thr
                180                 185                 190
Thr Trp Ser Pro Trp Ser Gln Pro Leu Ala Phe Arg Thr Lys Pro Ala
                195                 200                 205
Ala Leu Gly Lys Asp Thr
                210

<210> SEQ ID NO 63
<211> LENGTH: 214
<212> TYPE: PRT
<213> ORGANISM: Homo sapiens

<400> SEQUENCE: 63

Ala Val Asn Gly Thr Ser Gln Phe Thr Cys Phe Tyr Asn Ser Arg Ala
 1               5                  10                  15
Asn Ile Ser Cys Val Trp Ser Gln Asp Gly Ala Leu Gln Asp Thr Ser
                20                  25                  30
Cys Gln Val His Ala Trp Pro Asp Arg Arg Arg Trp Asn Gln Thr Cys
                35                  40                  45
Glu Leu Leu Pro Val Ser Gln Ala Ser Trp Ala Cys Asn Leu Ile Leu
 50                  55                  60
Ala Ala Pro Asp Ser Gln Lys Leu Thr Thr Val Asp Ile Val Thr Leu
 65                  70                  75                  80
Arg Val Leu Cys Arg Glu Gly Val Arg Trp Arg Val Met Ala Ile Gln
                    85                  90                  95
Asp Phe Lys Pro Phe Glu Asn Leu Arg Leu Met Ala Pro Ile Ser Leu
                100                 105                 110
Gln Val Val His Val Glu Thr His Arg Cys Asn Ile Ser Trp Glu Ile
                115                 120                 125
Ser Gln Ala Ser His Tyr Phe Glu Arg His Leu Glu Phe Glu Ala Arg
    130                 135                 140
Thr Leu Ser Pro Gly His Thr Trp Glu Glu Ala Pro Leu Leu Thr Leu
145                 150                 155                 160
Lys Gln Lys Gln Glu Trp Ile Cys Leu Glu Thr Leu Thr Pro Asp Thr
                165                 170                 175
Gln Tyr Glu Phe Gln Val Arg Val Lys Pro Leu Gln Gly Glu Phe Thr
                180                 185                 190
```

Thr Trp Ser Pro Trp Ser Gln Pro Leu Ala Phe Arg Thr Lys Pro Ala
            195                 200                 205

Ala Leu Gly Lys Asp Thr
            210

<210> SEQ ID NO 64
<211> LENGTH: 214
<212> TYPE: PRT
<213> ORGANISM: Homo sapiens

<400> SEQUENCE: 64

Ala Val Asn Gly Thr Ser Gln Phe Thr Cys Phe Tyr Asn Ser Arg Ala
1               5                   10                  15

Asn Ile Ser Cys Val Trp Ser Gln Asp Gly Ala Leu Gln Asp Thr Ser
            20                  25                  30

Cys Gln Val His Ala Trp Pro Asp Arg Arg Arg Trp Asn Gln Thr Cys
        35                  40                  45

Glu Leu Leu Pro Val Ser Gln Ala Ser Trp Ala Cys Asn Leu Ile Leu
    50                  55                  60

Thr Ala Pro Asp Ser Gln Lys Leu Thr Thr Val Asp Ile Val Thr Leu
65                  70                  75                  80

Arg Val Leu Cys Arg Glu Gly Val Arg Trp Arg Val Met Ala Ile Gln
                85                  90                  95

Asp Phe Lys Pro Phe Glu Asn Leu Arg Leu Met Ala Pro Ile Ser Leu
            100                 105                 110

Gln Val Val His Val Glu Thr His Arg Cys Asn Ile Ser Trp Glu Ile
        115                 120                 125

Ser Gln Ala Ser His Tyr Phe Glu Arg His Leu Glu Phe Glu Ala Arg
    130                 135                 140

Thr Leu Ser Pro Gly His Thr Trp Glu Glu Ala Pro Leu Leu Thr Leu
145                 150                 155                 160

Lys Gln Lys Gln Glu Trp Ile Cys Leu Glu Thr Leu Thr Pro Asp Thr
                165                 170                 175

Gln Tyr Glu Phe Gln Val Arg Val Lys Pro Leu Gln Gly Glu Phe Thr
            180                 185                 190

Thr Trp Ser Pro Trp Ser Gln Pro Leu Ala Phe Arg Thr Lys Pro Ala
        195                 200                 205

Ala Leu Gly Lys Asp Thr
    210

<210> SEQ ID NO 65
<211> LENGTH: 214
<212> TYPE: PRT
<213> ORGANISM: Homo sapiens

<400> SEQUENCE: 65

Ala Val Asn Gly Thr Ser Gln Phe Thr Cys Phe Tyr Asn Ser Arg Ala
1               5                   10                  15

Asn Ile Ser Cys Val Trp Ser Gln Asp Gly Ala Leu Gln Asp Thr Ser
            20                  25                  30

Cys Gln Val His Ala Trp Pro Asp Arg Arg Arg Trp Asn Gln Thr Cys
        35                  40                  45

Glu Leu Leu Pro Val Ser Gln Ala Ser Trp Ala Cys Asn Leu Ile Leu
    50                  55                  60

Gly Ser Pro Asp Ser Gln Lys Leu Thr Thr Val Asp Ile Val Thr Leu
65                  70                  75                  80

Arg Val Leu Cys Arg Glu Gly Val Arg Trp Arg Val Met Ala Ile Gln
            85                  90                  95

Asp Phe Lys Pro Phe Glu Asn Leu Arg Leu Met Ala Pro Ile Ser Leu
            100                 105                 110

Gln Val Val His Val Glu Thr His Arg Cys Asn Ile Ser Trp Glu Ile
            115                 120                 125

Ser Gln Ala Ser His Tyr Phe Glu Arg His Leu Glu Phe Glu Ala Arg
            130                 135                 140

Thr Leu Ser Pro Gly His Thr Trp Glu Glu Ala Pro Leu Leu Thr Leu
145                 150                 155                 160

Lys Gln Lys Gln Glu Trp Ile Cys Leu Glu Thr Leu Thr Pro Asp Thr
                165                 170                 175

Gln Tyr Glu Phe Gln Val Arg Val Lys Pro Leu Gln Gly Glu Phe Thr
            180                 185                 190

Thr Trp Ser Pro Trp Ser Gln Pro Leu Ala Phe Arg Thr Lys Pro Ala
            195                 200                 205

Ala Leu Gly Lys Asp Thr
    210

<210> SEQ ID NO 66
<211> LENGTH: 214
<212> TYPE: PRT
<213> ORGANISM: Homo sapiens

<400> SEQUENCE: 66

Ala Val Asn Gly Thr Ser Gln Phe Thr Cys Phe Tyr Asn Ser Arg Ala
1               5                   10                  15

Asn Ile Ser Cys Val Trp Ser Gln Asp Gly Ala Leu Gln Asp Thr Ser
            20                  25                  30

Cys Gln Val His Ala Trp Pro Asp Arg Arg Trp Asn Gln Thr Cys
            35                  40                  45

Glu Leu Leu Pro Val Ser Gln Ala Ser Trp Ala Cys Asn Leu Ile Leu
            50                  55                  60

Gly Ala Pro Asp Ala Gln Lys Leu Thr Thr Val Asp Ile Val Thr Leu
65                  70                  75                  80

Arg Val Leu Cys Arg Glu Gly Val Arg Trp Arg Val Met Ala Ile Gln
            85                  90                  95

Asp Phe Lys Pro Phe Glu Asn Leu Arg Leu Met Ala Pro Ile Ser Leu
            100                 105                 110

Gln Val Val His Val Glu Thr His Arg Cys Asn Ile Ser Trp Glu Ile
            115                 120                 125

Ser Gln Ala Ser His Tyr Phe Glu Arg His Leu Glu Phe Glu Ala Arg
            130                 135                 140

Thr Leu Ser Pro Gly His Thr Trp Glu Glu Ala Pro Leu Leu Thr Leu
145                 150                 155                 160

Lys Gln Lys Gln Glu Trp Ile Cys Leu Glu Thr Leu Thr Pro Asp Thr
                165                 170                 175

Gln Tyr Glu Phe Gln Val Arg Val Lys Pro Leu Gln Gly Glu Phe Thr
            180                 185                 190

Thr Trp Ser Pro Trp Ser Gln Pro Leu Ala Phe Arg Thr Lys Pro Ala
            195                 200                 205

Ala Leu Gly Lys Asp Thr
    210

<210> SEQ ID NO 67

```
<211> LENGTH: 214
<212> TYPE: PRT
<213> ORGANISM: Homo sapiens

<400> SEQUENCE: 67

Ala Val Asn Gly Thr Ser Gln Phe Thr Cys Phe Tyr Asn Ser Arg Ala
1               5                   10                  15

Asn Ile Ser Cys Val Trp Ser Gln Asp Gly Ala Leu Gln Asp Thr Ser
            20                  25                  30

Cys Gln Val His Ala Trp Pro Asp Arg Arg Trp Asn Gln Thr Cys
        35                  40                  45

Glu Leu Leu Pro Val Ser Gln Ala Ser Trp Ala Cys Asn Leu Ile Leu
50                  55                  60

Gly Ala Pro Asp Ser Ala Lys Leu Thr Thr Val Asp Ile Val Thr Leu
65                  70                  75                  80

Arg Val Leu Cys Arg Glu Gly Val Arg Trp Arg Val Met Ala Ile Gln
                85                  90                  95

Asp Phe Lys Pro Phe Glu Asn Leu Arg Leu Met Ala Pro Ile Ser Leu
            100                 105                 110

Gln Val Val His Val Glu Thr His Arg Cys Asn Ile Ser Trp Glu Ile
        115                 120                 125

Ser Gln Ala Ser His Tyr Phe Glu Arg His Leu Glu Phe Glu Ala Arg
    130                 135                 140

Thr Leu Ser Pro Gly His Thr Trp Glu Glu Ala Pro Leu Leu Thr Leu
145                 150                 155                 160

Lys Gln Lys Gln Glu Trp Ile Cys Leu Glu Thr Leu Thr Pro Asp Thr
                165                 170                 175

Gln Tyr Glu Phe Gln Val Arg Val Lys Pro Leu Gln Gly Glu Phe Thr
            180                 185                 190

Thr Trp Ser Pro Trp Ser Gln Pro Leu Ala Phe Arg Thr Lys Pro Ala
        195                 200                 205

Ala Leu Gly Lys Asp Thr
    210

<210> SEQ ID NO 68
<211> LENGTH: 214
<212> TYPE: PRT
<213> ORGANISM: Homo sapiens

<400> SEQUENCE: 68

Ala Val Asn Gly Thr Ser Gln Phe Thr Cys Phe Tyr Asn Ser Arg Ala
1               5                   10                  15

Asn Ile Ser Cys Val Trp Ser Gln Asp Gly Ala Leu Gln Asp Thr Ser
            20                  25                  30

Cys Gln Val His Ala Trp Pro Asp Arg Arg Trp Asn Gln Thr Cys
        35                  40                  45

Glu Leu Leu Pro Val Ser Gln Ala Ser Trp Ala Cys Asn Leu Ile Leu
50                  55                  60

Gly Ala Pro Asp Ser Lys Lys Leu Thr Thr Val Asp Ile Val Thr Leu
65                  70                  75                  80

Arg Val Leu Cys Arg Glu Gly Val Arg Trp Arg Val Met Ala Ile Gln
                85                  90                  95

Asp Phe Lys Pro Phe Glu Asn Leu Arg Leu Met Ala Pro Ile Ser Leu
            100                 105                 110

Gln Val Val His Val Glu Thr His Arg Cys Asn Ile Ser Trp Glu Ile
        115                 120                 125
```

```
Ser Gln Ala Ser His Tyr Phe Glu Arg His Leu Glu Phe Glu Ala Arg
        130                 135                 140

Thr Leu Ser Pro Gly His Thr Trp Glu Glu Ala Pro Leu Leu Thr Leu
145                 150                 155                 160

Lys Gln Lys Gln Glu Trp Ile Cys Leu Glu Thr Leu Thr Pro Asp Thr
                165                 170                 175

Gln Tyr Glu Phe Gln Val Arg Val Lys Pro Leu Gln Gly Glu Phe Thr
            180                 185                 190

Thr Trp Ser Pro Trp Ser Gln Pro Leu Ala Phe Arg Thr Lys Pro Ala
        195                 200                 205

Ala Leu Gly Lys Asp Thr
        210

<210> SEQ ID NO 69
<211> LENGTH: 214
<212> TYPE: PRT
<213> ORGANISM: Homo sapiens

<400> SEQUENCE: 69

Ala Val Asn Gly Thr Ser Gln Phe Thr Cys Phe Tyr Asn Ser Arg Ala
1               5                   10                  15

Asn Ile Ser Cys Val Trp Ser Gln Asp Gly Ala Leu Gln Asp Thr Ser
                20                  25                  30

Cys Gln Val His Ala Trp Pro Asp Arg Arg Arg Trp Asn Gln Thr Cys
            35                  40                  45

Glu Leu Leu Pro Val Ser Gln Ala Ser Trp Ala Cys Asn Leu Ile Leu
        50                  55                  60

Gly Ala Pro Asp Ser Gln Ala Leu Thr Thr Val Asp Ile Val Thr Leu
65                  70                  75                  80

Arg Val Leu Cys Arg Glu Gly Val Arg Trp Arg Val Met Ala Ile Gln
                85                  90                  95

Asp Phe Lys Pro Phe Glu Asn Leu Arg Leu Met Ala Pro Ile Ser Leu
            100                 105                 110

Gln Val Val His Val Glu Thr His Arg Cys Asn Ile Ser Trp Glu Ile
        115                 120                 125

Ser Gln Ala Ser His Tyr Phe Glu Arg His Leu Glu Phe Glu Ala Arg
        130                 135                 140

Thr Leu Ser Pro Gly His Thr Trp Glu Glu Ala Pro Leu Leu Thr Leu
145                 150                 155                 160

Lys Gln Lys Gln Glu Trp Ile Cys Leu Glu Thr Leu Thr Pro Asp Thr
                165                 170                 175

Gln Tyr Glu Phe Gln Val Arg Val Lys Pro Leu Gln Gly Glu Phe Thr
            180                 185                 190

Thr Trp Ser Pro Trp Ser Gln Pro Leu Ala Phe Arg Thr Lys Pro Ala
        195                 200                 205

Ala Leu Gly Lys Asp Thr
        210

<210> SEQ ID NO 70
<211> LENGTH: 214
<212> TYPE: PRT
<213> ORGANISM: Homo sapiens

<400> SEQUENCE: 70

Ala Val Asn Gly Thr Ser Gln Phe Thr Cys Phe Tyr Asn Ser Arg Ala
1               5                   10                  15
```

Asn Ile Ser Cys Val Trp Ser Gln Asp Gly Ala Leu Gln Asp Thr Ser
            20                  25                  30

Cys Gln Val His Ala Trp Pro Asp Arg Arg Trp Asn Gln Thr Cys
        35                  40                  45

Glu Leu Leu Pro Val Ser Gln Ala Ser Trp Ala Cys Asn Leu Ile Leu
    50                  55                  60

Gly Ala Pro Asp Ser Gln Lys Leu Thr Thr Val Asp Ile Val Thr Leu
65                  70                  75                  80

Arg Val Leu Cys Arg Glu Gly Val Arg Trp Arg Val Met Ala Ile Gln
                85                  90                  95

Asp Phe Lys Pro Phe Glu Asn Leu Arg Leu Met Ala Pro Ile Ser Leu
                100                 105                 110

Gln Val Val His Val Glu Thr His Arg Cys Asn Ile Ser Trp Glu Ile
            115                 120                 125

Ser Gln Ala Ala His Tyr Phe Glu Arg His Leu Glu Phe Glu Ala Arg
    130                 135                 140

Thr Leu Ser Pro Gly His Thr Trp Glu Glu Ala Pro Leu Leu Thr Leu
145                 150                 155                 160

Lys Gln Lys Gln Glu Trp Ile Cys Leu Glu Thr Leu Thr Pro Asp Thr
                165                 170                 175

Gln Tyr Glu Phe Gln Val Arg Val Lys Pro Leu Gln Gly Glu Phe Thr
                180                 185                 190

Thr Trp Ser Pro Trp Ser Gln Pro Leu Ala Phe Arg Thr Lys Pro Ala
            195                 200                 205

Ala Leu Gly Lys Asp Thr
        210

<210> SEQ ID NO 71
<211> LENGTH: 214
<212> TYPE: PRT
<213> ORGANISM: Homo sapiens

<400> SEQUENCE: 71

Ala Val Asn Gly Thr Ser Gln Phe Thr Cys Phe Tyr Asn Ser Arg Ala
1               5                   10                  15

Asn Ile Ser Cys Val Trp Ser Gln Asp Gly Ala Leu Gln Asp Thr Ser
            20                  25                  30

Cys Gln Val His Ala Trp Pro Asp Arg Arg Trp Asn Gln Thr Cys
        35                  40                  45

Glu Leu Leu Pro Val Ser Gln Ala Ser Trp Ala Cys Asn Leu Ile Leu
    50                  55                  60

Gly Ala Pro Asp Ser Gln Lys Leu Thr Thr Val Asp Ile Val Thr Leu
65                  70                  75                  80

Arg Val Leu Cys Arg Glu Gly Val Arg Trp Arg Val Met Ala Ile Gln
                85                  90                  95

Asp Phe Lys Pro Phe Glu Asn Leu Arg Leu Met Ala Pro Ile Ser Leu
                100                 105                 110

Gln Val Val His Val Glu Thr His Arg Cys Asn Ile Ser Trp Glu Ile
            115                 120                 125

Ser Gln Ala Ser Ala Tyr Phe Glu Arg His Leu Glu Phe Glu Ala Arg
    130                 135                 140

Thr Leu Ser Pro Gly His Thr Trp Glu Glu Ala Pro Leu Leu Thr Leu
145                 150                 155                 160

Lys Gln Lys Gln Glu Trp Ile Cys Leu Glu Thr Leu Thr Pro Asp Thr

-continued

```
                165                 170                 175
Gln Tyr Glu Phe Gln Val Arg Val Lys Pro Leu Gln Gly Glu Phe Thr
            180                 185                 190

Thr Trp Ser Pro Trp Ser Gln Pro Leu Ala Phe Arg Thr Lys Pro Ala
        195                 200                 205

Ala Leu Gly Lys Asp Thr
    210

<210> SEQ ID NO 72
<211> LENGTH: 214
<212> TYPE: PRT
<213> ORGANISM: Homo sapiens

<400> SEQUENCE: 72

Ala Val Asn Gly Thr Ser Gln Phe Thr Cys Phe Tyr Asn Ser Arg Ala
1               5                   10                  15

Asn Ile Ser Cys Val Trp Ser Gln Asp Gly Ala Leu Gln Asp Thr Ser
            20                  25                  30

Cys Gln Val His Ala Trp Pro Asp Arg Arg Arg Trp Asn Gln Thr Cys
        35                  40                  45

Glu Leu Leu Pro Val Ser Gln Ala Ser Trp Ala Cys Asn Leu Ile Leu
    50                  55                  60

Gly Ala Pro Asp Ser Gln Lys Leu Thr Thr Val Asp Ile Val Thr Leu
65                  70                  75                  80

Arg Val Leu Cys Arg Glu Gly Val Arg Trp Arg Val Met Ala Ile Gln
                85                  90                  95

Asp Phe Lys Pro Phe Glu Asn Leu Arg Leu Met Ala Pro Ile Ser Leu
            100                 105                 110

Gln Val Val His Val Glu Thr His Arg Cys Asn Ile Ser Trp Glu Ile
        115                 120                 125

Ser Gln Ala Ser His Ala Phe Glu Arg His Leu Glu Phe Glu Ala Arg
    130                 135                 140

Thr Leu Ser Pro Gly His Thr Trp Glu Glu Ala Pro Leu Leu Thr Leu
145                 150                 155                 160

Lys Gln Lys Gln Glu Trp Ile Cys Leu Glu Thr Leu Thr Pro Asp Thr
                165                 170                 175

Gln Tyr Glu Phe Gln Val Arg Val Lys Pro Leu Gln Gly Glu Phe Thr
            180                 185                 190

Thr Trp Ser Pro Trp Ser Gln Pro Leu Ala Phe Arg Thr Lys Pro Ala
        195                 200                 205

Ala Leu Gly Lys Asp Thr
    210

<210> SEQ ID NO 73
<211> LENGTH: 525
<212> TYPE: PRT
<213> ORGANISM: Homo sapiens

<400> SEQUENCE: 73

Ala Val Asn Gly Thr Ser Gln Phe Thr Cys Phe Tyr Asn Ser Arg Ala
1               5                   10                  15

Asn Ile Ser Cys Val Trp Ser Gln Asp Gly Ala Leu Gln Asp Thr Ser
            20                  25                  30

Cys Gln Val His Ala Trp Pro Asp Arg Arg Arg Trp Asn Gln Thr Cys
        35                  40                  45

Glu Leu Leu Pro Val Ser Gln Ala Ser Trp Ala Cys Asn Leu Ile Leu
```

```
            50                  55                  60
Gly Ala Pro Asp Ser Gln Lys Leu Thr Thr Val Asp Ile Val Thr Leu
 65                  70                  75                  80

Arg Val Leu Cys Arg Glu Gly Val Arg Trp Arg Val Met Ala Ile Gln
                 85                  90                  95

Asp Phe Lys Pro Phe Glu Asn Leu Arg Leu Met Ala Pro Ile Ser Leu
            100                 105                 110

Gln Val Val His Val Glu Thr His Arg Cys Asn Ile Ser Trp Glu Ile
            115                 120                 125

Ser Gln Ala Ser His Tyr Phe Glu Arg His Leu Glu Phe Glu Ala Arg
    130                 135                 140

Thr Leu Ser Pro Gly His Thr Trp Glu Glu Ala Pro Leu Leu Thr Leu
145                 150                 155                 160

Lys Gln Lys Gln Glu Trp Ile Cys Leu Glu Thr Leu Thr Pro Asp Thr
                165                 170                 175

Gln Tyr Glu Phe Gln Val Arg Val Lys Pro Leu Gln Gly Glu Phe Thr
            180                 185                 190

Thr Trp Ser Pro Trp Ser Gln Pro Leu Ala Phe Arg Thr Lys Pro Ala
            195                 200                 205

Ala Leu Gly Lys Asp Thr Ile Pro Trp Leu Gly His Leu Leu Val Gly
210                 215                 220

Leu Ser Gly Ala Phe Gly Phe Ile Ile Leu Val Tyr Leu Leu Ile Asn
225                 230                 235                 240

Cys Arg Asn Thr Gly Pro Trp Leu Lys Lys Val Leu Lys Cys Asn Thr
                245                 250                 255

Pro Asp Pro Ser Lys Phe Phe Ser Gln Leu Ser Ser Glu His Gly Gly
            260                 265                 270

Asp Val Gln Lys Trp Leu Ser Ser Pro Phe Pro Ser Ser Ser Phe Ser
            275                 280                 285

Pro Gly Gly Leu Ala Pro Glu Ile Ser Pro Leu Glu Val Leu Glu Arg
            290                 295                 300

Asp Lys Val Thr Gln Leu Leu Leu Gln Asp Lys Val Pro Glu Pro
305                 310                 315                 320

Ala Ser Leu Ser Ser Asn His Ser Leu Thr Ser Cys Phe Thr Asn Gln
                325                 330                 335

Gly Tyr Phe Phe Phe His Leu Pro Asp Ala Leu Glu Ile Glu Ala Cys
            340                 345                 350

Gln Val Tyr Phe Thr Tyr Asp Pro Tyr Ser Glu Glu Asp Pro Asp Glu
            355                 360                 365

Gly Val Ala Gly Ala Pro Thr Gly Ser Ser Pro Gln Pro Leu Gln Pro
            370                 375                 380

Leu Ser Gly Glu Asp Asp Ala Tyr Cys Thr Phe Pro Ser Arg Asp Asp
385                 390                 395                 400

Leu Leu Leu Phe Ser Pro Ser Leu Leu Gly Gly Pro Ser Pro Pro Ser
                405                 410                 415

Thr Ala Pro Gly Gly Ser Gly Ala Gly Glu Glu Arg Met Pro Pro Ser
            420                 425                 430

Leu Gln Glu Arg Val Pro Arg Asp Trp Asp Pro Gln Pro Leu Gly Pro
            435                 440                 445

Pro Thr Pro Gly Val Pro Asp Leu Val Asp Phe Gln Pro Pro Pro Glu
            450                 455                 460

Leu Val Leu Arg Glu Ala Gly Glu Glu Val Pro Asp Ala Gly Pro Arg
465                 470                 475                 480
```

```
Glu Gly Val Ser Phe Pro Trp Ser Arg Pro Gly Gln Gly Glu Phe
            485                 490                 495

Arg Ala Leu Asn Ala Arg Leu Pro Leu Asn Thr Asp Ala Tyr Leu Ser
        500                 505                 510

Leu Gln Glu Leu Gln Gly Gln Asp Pro Thr His Leu Val
        515                 520                 525

<210> SEQ ID NO 74
<211> LENGTH: 525
<212> TYPE: PRT
<213> ORGANISM: Homo sapiens

<400> SEQUENCE: 74

Ala Val Asn Gly Thr Ser Gln Phe Thr Cys Phe Tyr Asn Ser Arg Ala
1               5                   10                  15

Asn Ile Ser Cys Val Trp Ser Gln Asp Gly Ala Leu Gln Asp Thr Ser
            20                  25                  30

Cys Gln Val His Ala Trp Pro Asp Arg Ala Arg Trp Asn Gln Thr Cys
        35                  40                  45

Glu Leu Leu Pro Val Ser Gln Ala Ser Trp Ala Cys Asn Leu Ile Leu
    50                  55                  60

Gly Ala Pro Asp Ser Gln Lys Leu Thr Thr Val Asp Ile Val Thr Leu
65                  70                  75                  80

Arg Val Leu Cys Arg Glu Gly Val Arg Trp Arg Val Met Ala Ile Gln
                85                  90                  95

Asp Phe Lys Pro Phe Glu Asn Leu Arg Leu Met Ala Pro Ile Ser Leu
            100                 105                 110

Gln Val Val His Val Glu Thr His Arg Cys Asn Ile Ser Trp Glu Ile
        115                 120                 125

Ser Gln Ala Ser His Tyr Phe Glu Arg His Leu Glu Phe Glu Ala Arg
    130                 135                 140

Thr Leu Ser Pro Gly His Thr Trp Glu Glu Ala Pro Leu Leu Thr Leu
145                 150                 155                 160

Lys Gln Lys Gln Glu Trp Ile Cys Leu Glu Thr Leu Thr Pro Asp Thr
                165                 170                 175

Gln Tyr Glu Phe Gln Val Arg Val Lys Pro Leu Gln Gly Glu Phe Thr
            180                 185                 190

Thr Trp Ser Pro Trp Ser Gln Pro Leu Ala Phe Arg Thr Lys Pro Ala
        195                 200                 205

Ala Leu Gly Lys Asp Thr Ile Pro Trp Leu Gly His Leu Leu Val Gly
    210                 215                 220

Leu Ser Gly Ala Phe Gly Phe Ile Ile Leu Val Tyr Leu Leu Ile Asn
225                 230                 235                 240

Cys Arg Asn Thr Gly Pro Trp Leu Lys Lys Val Leu Lys Cys Asn Thr
                245                 250                 255

Pro Asp Pro Ser Lys Phe Phe Ser Gln Leu Ser Ser Glu His Gly Gly
            260                 265                 270

Asp Val Gln Lys Trp Leu Ser Ser Pro Phe Pro Ser Ser Ser Phe Ser
        275                 280                 285

Pro Gly Gly Leu Ala Pro Glu Ile Ser Pro Leu Glu Val Leu Glu Arg
    290                 295                 300

Asp Lys Val Thr Gln Leu Leu Leu Gln Asp Lys Val Pro Glu Pro
305                 310                 315                 320

Ala Ser Leu Ser Ser Asn His Ser Leu Thr Ser Cys Phe Thr Asn Gln
```

-continued

```
                325                 330                 335
Gly Tyr Phe Phe Phe His Leu Pro Asp Ala Leu Glu Ile Glu Ala Cys
            340                 345                 350
Gln Val Tyr Phe Thr Tyr Asp Pro Tyr Ser Glu Glu Asp Pro Asp Glu
            355                 360                 365
Gly Val Ala Gly Ala Pro Thr Gly Ser Ser Pro Gln Pro Leu Gln Pro
        370                 375                 380
Leu Ser Gly Glu Asp Asp Ala Tyr Cys Thr Phe Pro Ser Arg Asp Asp
385                 390                 395                 400
Leu Leu Leu Phe Ser Pro Ser Leu Leu Gly Gly Pro Ser Pro Pro Ser
                405                 410                 415
Thr Ala Pro Gly Gly Ser Gly Ala Gly Glu Glu Arg Met Pro Pro Ser
            420                 425                 430
Leu Gln Glu Arg Val Pro Arg Asp Trp Asp Pro Gln Pro Leu Gly Pro
            435                 440                 445
Pro Thr Pro Gly Val Pro Asp Leu Val Asp Phe Gln Pro Pro Pro Glu
        450                 455                 460
Leu Val Leu Arg Glu Ala Gly Glu Glu Val Pro Asp Ala Gly Pro Arg
465                 470                 475                 480
Glu Gly Val Ser Phe Pro Trp Ser Arg Pro Pro Gly Gln Gly Glu Phe
                485                 490                 495
Arg Ala Leu Asn Ala Arg Leu Pro Leu Asn Thr Asp Ala Tyr Leu Ser
            500                 505                 510
Leu Gln Glu Leu Gln Gly Gln Asp Pro Thr His Leu Val
            515                 520                 525

<210> SEQ ID NO 75
<211> LENGTH: 525
<212> TYPE: PRT
<213> ORGANISM: Homo sapiens

<400> SEQUENCE: 75

Ala Val Asn Gly Thr Ser Gln Phe Thr Cys Phe Tyr Asn Ser Arg Ala
1               5                   10                  15
Asn Ile Ser Cys Val Trp Ser Gln Asp Gly Ala Leu Gln Asp Thr Ser
            20                  25                  30
Cys Gln Val His Ala Trp Pro Asp Arg Arg Ala Trp Asn Gln Thr Cys
        35                  40                  45
Glu Leu Leu Pro Val Ser Gln Ala Ser Trp Ala Cys Asn Leu Ile Leu
    50                  55                  60
Gly Ala Pro Asp Ser Gln Lys Leu Thr Thr Val Asp Ile Val Thr Leu
65                  70                  75                  80
Arg Val Leu Cys Arg Glu Gly Val Arg Trp Arg Val Met Ala Ile Gln
                85                  90                  95
Asp Phe Lys Pro Phe Glu Asn Leu Arg Leu Met Ala Pro Ile Ser Leu
            100                 105                 110
Gln Val Val His Val Glu Thr His Arg Cys Asn Ile Ser Trp Glu Ile
        115                 120                 125
Ser Gln Ala Ser His Tyr Phe Glu Arg His Leu Glu Phe Glu Ala Arg
    130                 135                 140
Thr Leu Ser Pro Gly His Thr Trp Glu Glu Ala Pro Leu Leu Thr Leu
145                 150                 155                 160
Lys Gln Lys Gln Glu Trp Ile Cys Leu Glu Thr Leu Thr Pro Asp Thr
                165                 170                 175
```

Gln Tyr Glu Phe Gln Val Arg Val Lys Pro Leu Gln Gly Glu Phe Thr
                180                 185                 190

Thr Trp Ser Pro Trp Ser Gln Pro Leu Ala Phe Arg Thr Lys Pro Ala
            195                 200                 205

Ala Leu Gly Lys Asp Thr Ile Pro Trp Leu Gly His Leu Leu Val Gly
        210                 215                 220

Leu Ser Gly Ala Phe Gly Phe Ile Ile Leu Val Tyr Leu Leu Ile Asn
225                 230                 235                 240

Cys Arg Asn Thr Gly Pro Trp Leu Lys Lys Val Leu Lys Cys Asn Thr
                245                 250                 255

Pro Asp Pro Ser Lys Phe Phe Ser Gln Leu Ser Ser Glu His Gly Gly
            260                 265                 270

Asp Val Gln Lys Trp Leu Ser Ser Pro Phe Pro Ser Ser Ser Phe Ser
        275                 280                 285

Pro Gly Gly Leu Ala Pro Glu Ile Ser Pro Leu Glu Val Leu Glu Arg
        290                 295                 300

Asp Lys Val Thr Gln Leu Leu Leu Gln Gln Asp Lys Val Pro Glu Pro
305                 310                 315                 320

Ala Ser Leu Ser Ser Asn His Ser Leu Thr Ser Cys Phe Thr Asn Gln
                325                 330                 335

Gly Tyr Phe Phe Phe His Leu Pro Asp Ala Leu Glu Ile Glu Ala Cys
            340                 345                 350

Gln Val Tyr Phe Thr Tyr Asp Pro Tyr Ser Glu Glu Asp Pro Asp Glu
        355                 360                 365

Gly Val Ala Gly Ala Pro Thr Gly Ser Ser Pro Gln Pro Leu Gln Pro
        370                 375                 380

Leu Ser Gly Glu Asp Asp Ala Tyr Cys Thr Phe Pro Ser Arg Asp Asp
385                 390                 395                 400

Leu Leu Leu Phe Ser Pro Ser Leu Leu Gly Gly Pro Ser Pro Pro Ser
                405                 410                 415

Thr Ala Pro Gly Gly Ser Gly Ala Gly Glu Glu Arg Met Pro Pro Ser
            420                 425                 430

Leu Gln Glu Arg Val Pro Arg Asp Trp Asp Pro Gln Pro Leu Gly Pro
        435                 440                 445

Pro Thr Pro Gly Val Pro Asp Leu Val Asp Phe Gln Pro Pro Pro Glu
        450                 455                 460

Leu Val Leu Arg Glu Ala Gly Glu Glu Val Pro Asp Ala Gly Pro Arg
465                 470                 475                 480

Glu Gly Val Ser Phe Pro Trp Ser Arg Pro Pro Gly Gln Gly Glu Phe
                485                 490                 495

Arg Ala Leu Asn Ala Arg Leu Pro Leu Asn Thr Asp Ala Tyr Leu Ser
            500                 505                 510

Leu Gln Glu Leu Gln Gly Gln Asp Pro Thr His Leu Val
        515                 520                 525

<210> SEQ ID NO 76
<211> LENGTH: 525
<212> TYPE: PRT
<213> ORGANISM: Homo sapiens

<400> SEQUENCE: 76

Ala Val Asn Gly Thr Ser Gln Phe Thr Cys Phe Tyr Asn Ser Arg Ala
1               5                   10                  15

Asn Ile Ser Cys Val Trp Ser Gln Asp Gly Ala Leu Gln Asp Thr Ser
            20                  25                  30

-continued

```
Cys Gln Val His Ala Trp Pro Asp Arg Arg Trp Asn Gln Thr Cys
        35                  40                  45
Glu Leu Leu Pro Val Ser Gln Ala Ser Trp Ala Cys Asn Leu Ile Leu
 50                  55                  60
Thr Ala Pro Asp Ser Gln Lys Leu Thr Thr Val Asp Ile Val Thr Leu
 65                  70                  75                  80
Arg Val Leu Cys Arg Glu Gly Val Arg Trp Arg Val Met Ala Ile Gln
                 85                  90                  95
Asp Phe Lys Pro Phe Glu Asn Leu Arg Leu Met Ala Pro Ile Ser Leu
                100                 105                 110
Gln Val Val His Val Glu Thr His Arg Cys Asn Ile Ser Trp Glu Ile
                115                 120                 125
Ser Gln Ala Ser His Tyr Phe Glu Arg His Leu Glu Phe Glu Ala Arg
        130                 135                 140
Thr Leu Ser Pro Gly His Thr Trp Glu Glu Ala Pro Leu Leu Thr Leu
145                 150                 155                 160
Lys Gln Lys Gln Glu Trp Ile Cys Leu Glu Thr Leu Thr Pro Asp Thr
                165                 170                 175
Gln Tyr Glu Phe Gln Val Arg Val Lys Pro Leu Gln Gly Glu Phe Thr
                180                 185                 190
Thr Trp Ser Pro Trp Ser Gln Pro Leu Ala Phe Arg Thr Lys Pro Ala
        195                 200                 205
Ala Leu Gly Lys Asp Thr Ile Pro Trp Leu Gly His Leu Leu Val Gly
        210                 215                 220
Leu Ser Gly Ala Phe Gly Phe Ile Ile Leu Val Tyr Leu Leu Ile Asn
225                 230                 235                 240
Cys Arg Asn Thr Gly Pro Trp Leu Lys Lys Val Leu Lys Cys Asn Thr
                245                 250                 255
Pro Asp Pro Ser Lys Phe Phe Ser Gln Leu Ser Ser Glu His Gly Gly
                260                 265                 270
Asp Val Gln Lys Trp Leu Ser Ser Pro Phe Pro Ser Ser Ser Phe Ser
        275                 280                 285
Pro Gly Gly Leu Ala Pro Glu Ile Ser Pro Leu Glu Val Leu Glu Arg
        290                 295                 300
Asp Lys Val Thr Gln Leu Leu Leu Gln Gln Asp Lys Val Pro Glu Pro
305                 310                 315                 320
Ala Ser Leu Ser Ser Asn His Ser Leu Thr Ser Cys Phe Thr Asn Gln
                325                 330                 335
Gly Tyr Phe Phe Phe His Leu Pro Asp Ala Leu Glu Ile Glu Ala Cys
                340                 345                 350
Gln Val Tyr Phe Thr Tyr Asp Pro Tyr Ser Glu Glu Asp Pro Asp Glu
        355                 360                 365
Gly Val Ala Gly Ala Pro Thr Gly Ser Ser Pro Gln Pro Leu Gln Pro
        370                 375                 380
Leu Ser Gly Glu Asp Asp Ala Tyr Cys Thr Phe Pro Ser Arg Asp Asp
385                 390                 395                 400
Leu Leu Leu Phe Ser Pro Ser Leu Leu Gly Gly Pro Ser Pro Pro Ser
                405                 410                 415
Thr Ala Pro Gly Gly Ser Gly Ala Gly Glu Glu Arg Met Pro Pro Ser
                420                 425                 430
Leu Gln Glu Arg Val Pro Arg Asp Trp Asp Pro Gln Pro Leu Gly Pro
        435                 440                 445
```

```
Pro Thr Pro Gly Val Pro Asp Leu Val Asp Phe Gln Pro Pro Glu
    450                 455                 460
Leu Val Leu Arg Glu Ala Gly Glu Val Pro Asp Ala Gly Pro Arg
465                 470                 475                 480
Glu Gly Val Ser Phe Pro Trp Ser Arg Pro Gly Gln Gly Glu Phe
                485                 490                 495
Arg Ala Leu Asn Ala Arg Leu Pro Leu Asn Thr Asp Ala Tyr Leu Ser
                500                 505                 510
Leu Gln Glu Leu Gln Gly Gln Asp Pro Thr His Leu Val
            515                 520                 525

<210> SEQ ID NO 77
<211> LENGTH: 525
<212> TYPE: PRT
<213> ORGANISM: Homo sapiens

<400> SEQUENCE: 77

Ala Val Asn Gly Thr Ser Gln Phe Thr Cys Phe Tyr Asn Ser Arg Ala
1               5                   10                  15
Asn Ile Ser Cys Val Trp Ser Gln Asp Gly Ala Leu Gln Asp Thr Ser
                20                  25                  30
Cys Gln Val His Ala Trp Pro Asp Arg Arg Arg Trp Asn Gln Thr Cys
            35                  40                  45
Glu Leu Leu Pro Val Ser Gln Ala Ser Trp Ala Cys Asn Leu Ile Leu
    50                  55                  60
Gly Ala Pro Asp Ser Gln Lys Leu Thr Thr Val Asp Ile Val Thr Leu
65                  70                  75                  80
Arg Val Leu Cys Arg Glu Gly Val Arg Trp Arg Val Met Ala Ile Gln
                85                  90                  95
Asp Phe Lys Pro Phe Glu Asn Leu Arg Leu Met Ala Pro Ile Ser Leu
            100                 105                 110
Gln Val Val His Val Glu Thr His Arg Cys Asn Ile Ser Trp Glu Ile
        115                 120                 125
Ser Gln Ala Ser Ala Tyr Phe Glu Arg His Leu Glu Phe Glu Ala Arg
    130                 135                 140
Thr Leu Ser Pro Gly His Thr Trp Glu Glu Ala Pro Leu Leu Thr Leu
145                 150                 155                 160
Lys Gln Lys Gln Glu Trp Ile Cys Leu Glu Thr Leu Thr Pro Asp Thr
                165                 170                 175
Gln Tyr Glu Phe Gln Val Arg Val Lys Pro Leu Gln Gly Glu Phe Thr
            180                 185                 190
Thr Trp Ser Pro Trp Ser Gln Pro Leu Ala Phe Arg Thr Lys Pro Ala
        195                 200                 205
Ala Leu Gly Lys Asp Thr Ile Pro Trp Leu Gly His Leu Leu Val Gly
    210                 215                 220
Leu Ser Gly Ala Phe Gly Phe Ile Ile Leu Val Tyr Leu Leu Ile Asn
225                 230                 235                 240
Cys Arg Asn Thr Gly Pro Trp Leu Lys Lys Val Leu Lys Cys Asn Thr
                245                 250                 255
Pro Asp Pro Ser Lys Phe Phe Ser Gln Leu Ser Ser Glu His Gly Gly
            260                 265                 270
Asp Val Gln Lys Trp Leu Ser Ser Pro Phe Pro Ser Ser Ser Phe Ser
        275                 280                 285
Pro Gly Gly Leu Ala Pro Glu Ile Ser Pro Leu Glu Val Leu Glu Arg
    290                 295                 300
```

```
Asp Lys Val Thr Gln Leu Leu Leu Gln Gln Asp Lys Val Pro Glu Pro
305                 310                 315                 320

Ala Ser Leu Ser Ser Asn His Ser Leu Thr Ser Cys Phe Thr Asn Gln
            325                 330                 335

Gly Tyr Phe Phe Phe His Leu Pro Asp Ala Leu Glu Ile Glu Ala Cys
                340                 345                 350

Gln Val Tyr Phe Thr Tyr Asp Pro Tyr Ser Glu Glu Asp Pro Asp Glu
            355                 360                 365

Gly Val Ala Gly Ala Pro Thr Gly Ser Ser Pro Gln Pro Leu Gln Pro
        370                 375                 380

Leu Ser Gly Glu Asp Asp Ala Tyr Cys Thr Phe Pro Ser Arg Asp Asp
385                 390                 395                 400

Leu Leu Leu Phe Ser Pro Ser Leu Leu Gly Gly Pro Ser Pro Pro Ser
                405                 410                 415

Thr Ala Pro Gly Gly Ser Gly Ala Gly Glu Glu Arg Met Pro Pro Ser
            420                 425                 430

Leu Gln Glu Arg Val Pro Arg Asp Trp Asp Pro Gln Pro Leu Gly Pro
        435                 440                 445

Pro Thr Pro Gly Val Pro Asp Leu Val Asp Phe Gln Pro Pro Pro Glu
    450                 455                 460

Leu Val Leu Arg Glu Ala Gly Glu Glu Val Pro Asp Ala Gly Pro Arg
465                 470                 475                 480

Glu Gly Val Ser Phe Pro Trp Ser Arg Pro Pro Gly Gln Gly Glu Phe
            485                 490                 495

Arg Ala Leu Asn Ala Arg Leu Pro Leu Asn Thr Asp Ala Tyr Leu Ser
            500                 505                 510

Leu Gln Glu Leu Gln Gly Gln Asp Pro Thr His Leu Val
        515                 520                 525
```